United States Patent
Diwu et al.

(10) Patent No.: US 12,297,383 B2
(45) Date of Patent: *May 13, 2025

(54) CONDENSED POLYCYCLIC CONJUGATED POLYMERS AND THEIR USE FOR BIOLOGICAL DETECTION

(71) Applicant: AAT Bioquest, Inc., Sunnyvale, CA (US)

(72) Inventors: Zhenjun Diwu, Sunnyvale, CA (US); Haitao Guo, Sunnyvale, CA (US); Jixiang Liu, Santa Clara, CA (US); Qin Zhao, Sunnyvale, CA (US); Ruogu Peng, San Jose, CA (US)

(73) Assignee: AAT Bioquest, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,393

(22) Filed: Oct. 16, 2023

(65) Prior Publication Data

US 2024/0052238 A1 Feb. 15, 2024

Related U.S. Application Data

(63) Continuation of application No. 17/542,223, filed on Dec. 3, 2021, now Pat. No. 11,827,824, which is a (Continued)

(51) Int. Cl.
C09K 11/06 (2006.01)
C08G 61/12 (2006.01)
(Continued)

(52) U.S. Cl.
CPC ............ C09K 11/06 (2013.01); C08G 61/124 (2013.01); G01N 21/6428 (2013.01);
(Continued)

(58) Field of Classification Search
None
See application file for complete search history.

(56) References Cited

U.S. PATENT DOCUMENTS

| 4,711,955 A | 12/1987 | Ward et al. |
| 5,047,519 A | 9/1991 | Hobbs et al. |

(Continued)

FOREIGN PATENT DOCUMENTS

| EP | 1491568 | 12/2004 |
| WO | WO 2008/009343 A1 | 1/2008 |

(Continued)

OTHER PUBLICATIONS

Feng et al., "An A-D-A Type Small-Molecule Electron Acceptor with End-Extended Conjugation for High Performance Organic Solar Cells," Chemistry of Materials, Aug. 29, 2017 vol. 29, pp. 7908-7917.

(Continued)

*Primary Examiner* — Xiaoyun R Xu
(74) *Attorney, Agent, or Firm* — Fenwick & West LLP

(57) ABSTRACT

Fluorescent water soluble conjugated polymers including polycyclic aromatic comonomers are provided. The conjugated polymers can be linked to an acceptor fluorescent dye. The conjugated polymers find use in conjugates with biological substrates having applications in a variety of applications including methods of analyte detection.

27 Claims, 10 Drawing Sheets

Related U.S. Application Data continuation of application No. 16/592,464, filed on Oct. 3, 2019, now Pat. No. 11,220,628.

(60) Provisional application No. 62/808,211, filed on Feb. 20, 2019.

(51) Int. Cl.
*G01N 21/64* (2006.01)
*G01N 33/533* (2006.01)

(52) U.S. Cl.
CPC ... *G01N 33/533* (2013.01); *C08G 2261/3241* (2013.01); *C09K 2211/1466* (2013.01); *G01N 2021/6439* (2013.01)

(56) References Cited

U.S. PATENT DOCUMENTS

| | | | |
|---|---|---|---|
| 5,659,025 A | 8/1997 | Engels et al. | |
| 5,668,268 A | 9/1997 | Tang et al. | |
| 5,679,785 A | 10/1997 | Engels et al. | |
| 5,684,142 A | 11/1997 | Mishra et al. | |
| 7,144,950 B2 | 12/2006 | Bazan et al. | |
| 7,241,512 B2 | 7/2007 | Li et al. | |
| 7,348,072 B2 | 3/2008 | Park et al. | |
| 7,897,684 B2 | 3/2011 | Bazan et al. | |
| 8,110,673 B2 | 2/2012 | Bazan et al. | |
| 8,158,444 B2 | 4/2012 | Gaylord et al. | |
| 8,354,239 B2 | 1/2013 | Gaylord et al. | |
| 8,362,193 B2 | 1/2013 | Gaylord et al. | |
| 8,455,613 B2 | 6/2013 | Gaylord et al. | |
| 8,557,953 B2 | 10/2013 | Heun et al. | |
| 8,575,303 B2 | 11/2013 | Gaylord et al. | |
| 8,835,113 B2 | 9/2014 | Bazan et al. | |
| 8,969,509 B2 | 3/2015 | Liu et al. | |
| 9,085,799 B2 | 7/2015 | Bazan et al. | |
| 9,139,869 B2 | 9/2015 | Gaylord et al. | |
| 9,159,465 B2 | 10/2015 | Bazan et al. | |
| 9,547,008 B2 | 1/2017 | Gaylord et al. | |
| 9,719,998 B2 | 8/2017 | Liang et al. | |
| 9,758,625 B2 | 9/2017 | Bartholomew et al. | |
| 9,896,538 B2 | 2/2018 | Diwu et al. | |
| 10,094,838 B2 | 10/2018 | Gaylord et al. | |
| 10,302,648 B2 | 5/2019 | Gaylord et al. | |
| 11,584,883 B2 | 2/2023 | Xu et al. | |
| 2005/0123802 A1 | 6/2005 | Park et al. | |
| 2019/0346450 A1 | 11/2019 | Gaylord et al. | |
| 2020/0239766 A1 | 7/2020 | Xu et al. | |
| 2023/0109663 A1 | 4/2023 | Xu et al. | |

FOREIGN PATENT DOCUMENTS

| | | |
|---|---|---|
| WO | WO 2010/136112 A1 | 12/2010 |
| WO | WO 2012/002911 A1 | 1/2012 |
| WO | WO 2012/163464 A1 | 12/2012 |
| WO | WO 2013/101902 A2 | 7/2013 |
| WO | WO 2019/023463 A1 | 1/2019 |

OTHER PUBLICATIONS

Hsiao et al., "Synthesis of Methylene-Bridge Polyarenes through Palladium-Catalyzed Activation of Benzylic Carbon-Hydrogen Bond," *Advanced Synthesis and Catalysis*, Dec. 17, 2010, vol. 352, Issue 18, pp. 3267-3274.

Lee, J., et al., "Donor-acceptor conjugated ladder polymer via aromatization-driven thermodynamic annulation," *Polymer Chemistry*, 9, pp. 1603-1609 (Year: 2018).

Thomas et al. "Chemical Sensors Based on Amplifying Fluorescent Conjugated Polymers," *Chemical Reviews*, Mar. 27, 2007, vol. 107, pp. 1339-1386.

Wang et al., "Broadband spectra with fluorescence and phosphorescence dual emission from bichromophoric platinum metallomesogens containing a 6,12-dihydro-indeno[1,2-b]fluorenelinkage," *RSC Advances*, May 4, 2016, vol. 6, pp. 45864-45872.

Zhu et al., "Water-Soluble Conjugated Polymers for Imaging, Diagnosis, and Therapy," *Chemical Reviews*, Jun. 6, 2012, vol. 112, pp. 4687-4735.

CONDENSED POLYCYCLIC CONJUGATED POLYMERS AND THEIR USE FOR BIOLOGICAL DETECTION

CROSS REFERENCE TO RELATED APPLICATIONS

This application is a continuation of co-pending U.S. application Ser. No. 17/542,223, filed Dec. 3, 2021, which is a continuation of U.S. application Ser. No. 16/592,464, filed Oct. 3, 2019, now U.S. Pat. No. 11,220,628, issued Jan. 11, 2022, which claims priority to U.S. Provisional Application No. 62/808,211, filed Feb. 20, 2019, the disclosures of which are herein incorporated by reference.

FIELD

The invention relates in general to fluorescent conjugated polymers, biological conjugates and their methods of analyte detection.

BACKGROUND

Fluorescent probes are valuable reagents for the analysis and separation of molecules and cells and for the detection and quantification of other materials. A very small number of fluorescent molecules can be detected under optimal circumstances. Barak and Webb visualized fewer than 50 fluorescent lipid analogs associated with the LDL reception of cells using a SIT camera, J. CELL BIOL., 90, 595-604 (1981). Flow cytometry can be used to detect fewer than 10,000 fluorescein molecules associated with particles or certain cells (Muirhead, Horan and Poste, BIOTECHNOLOGY, 3, 337-356 (1985)). Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining.

When employing fluorescent polymers for the above purposes, there are many constraints on the choice of the fluorescent polymer. One constraint is the absorption and emission characteristics of the fluorescent polymer, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescent polymer to ligands and receptors and other biological and non-biological materials and the effect of such conjugation on the fluorescent polymer. In many situations, conjugation to another molecule may result in a substantial change in the fluorescent characteristics of the fluorescent polymer and, in some cases, substantially destroy or reduce the quantum efficiency of the fluorescent polymer. It is also possible that conjugation with the fluorescent polymer will inactivate the function of the molecule that is labeled. A third consideration is the quantum efficiency of the fluorescent polymers which should be high for sensitive detection. A fourth consideration is the light absorbing capability, or extinction coefficient, of the fluorescent polymers, which should also be as large as possible. Also of concern is whether the fluorescent molecules will interact with each other when in close proximity, resulting in self-quenching. An additional concern is whether there is non-specific binding of the fluorescent polymers to other compounds or container walls, either by themselves or in conjunction with the compound to which the fluorescent polymer is conjugated.

The applicability and value of the methods indicated above are closely tied to the availability of suitable fluorescent compounds. In recent years, the rapid advances in lasers and LED technology have provided a variety of laser and LED excitation sources installed in new fluorescence instruments. In particular, there is a need for fluorescent substances that have strong absorption and emit fluorescence with a large Stokes shift, since excitation of these fluorophores produces less autofluorescence and also multiple chromophores fluorescing at different wavelengths can be analyzed simultaneously if the full visible and near infrared regions of the spectrum can be utilized.

Phycobiliproteins have made an important contribution because of their high extinction coefficient and high fluorescence quantum yield. These fluorophore-containing proteins can be covalently linked to many proteins and are used in fluorescence antibody assays in microscopy and flow cytometry. However, the phycobiliproteins have a few disadvantages that limit their biological applications, e.g., (1) the phycobiliproteins are relatively complex and tend to dissociate in highly diluted solutions; (2) They are extremely unstable and fade quickly upon illumination; (3) the phycobiliproteins have very weak absorption at 355 nm and 405 nm. Brightly fluorescent conjugated polymers permit detection or location of the attached materials with great sensitivity. Certain polyconjugated polymers have demonstrated utility as labeling reagents for immunological applications, e.g. U.S. Pat. Nos. 8,110,673; 8,835,113; 9,085,799 to Bazan et al; U.S. Pat. Nos. 9,719,998; 9,758,625; 9,547,008; 9,139,869; 8,158,444; 8,455,613; 8,354,239; 8,362,193; and 8,575,303 to Gaylord, et al.; U.S. Pat. No. 9,896,538 to Diwu et al.; WO2019023463 to Xu et al; WO 2013/101902 to Chiu et al. The other biological applications of polyconjugated polymers have been well documented by Thomas III et al. (Chem. Rev. 2007, 107, 1339); Zhu et al (Chem. Rev. 2012, 112, 4687) and Zhu et al. (Chem. Soc. Rev., 2011, 40, 3509). However, there are still greatly unmet needs for bright fluorescent probes with strong absorption at the important laser and LED lines with large Stokes shift for the diverse and complicated biological applications.

SUMMARY

Fluorescent water soluble conjugated polymers including polycyclic aromatic comonomers are provided. The conjugated polymers can be linked to an acceptor fluorescent dye. The conjugated polymers find use in conjugates with biological substrates having applications in a variety of applications including methods of analyte detection.

BRIEF DESCRIPTION OF THE DRAWINGS

The foregoing and other features and advantages of the present embodiments will be more fully understood from the following detailed description of illustrative embodiments taken in conjunction with the accompanying drawings in which:

(FIG. 7A). Control without mouse anti-tubulin added; (FIG. 7B). With mouse anti-tubulin added.

DEFINITIONS

Figure 1:
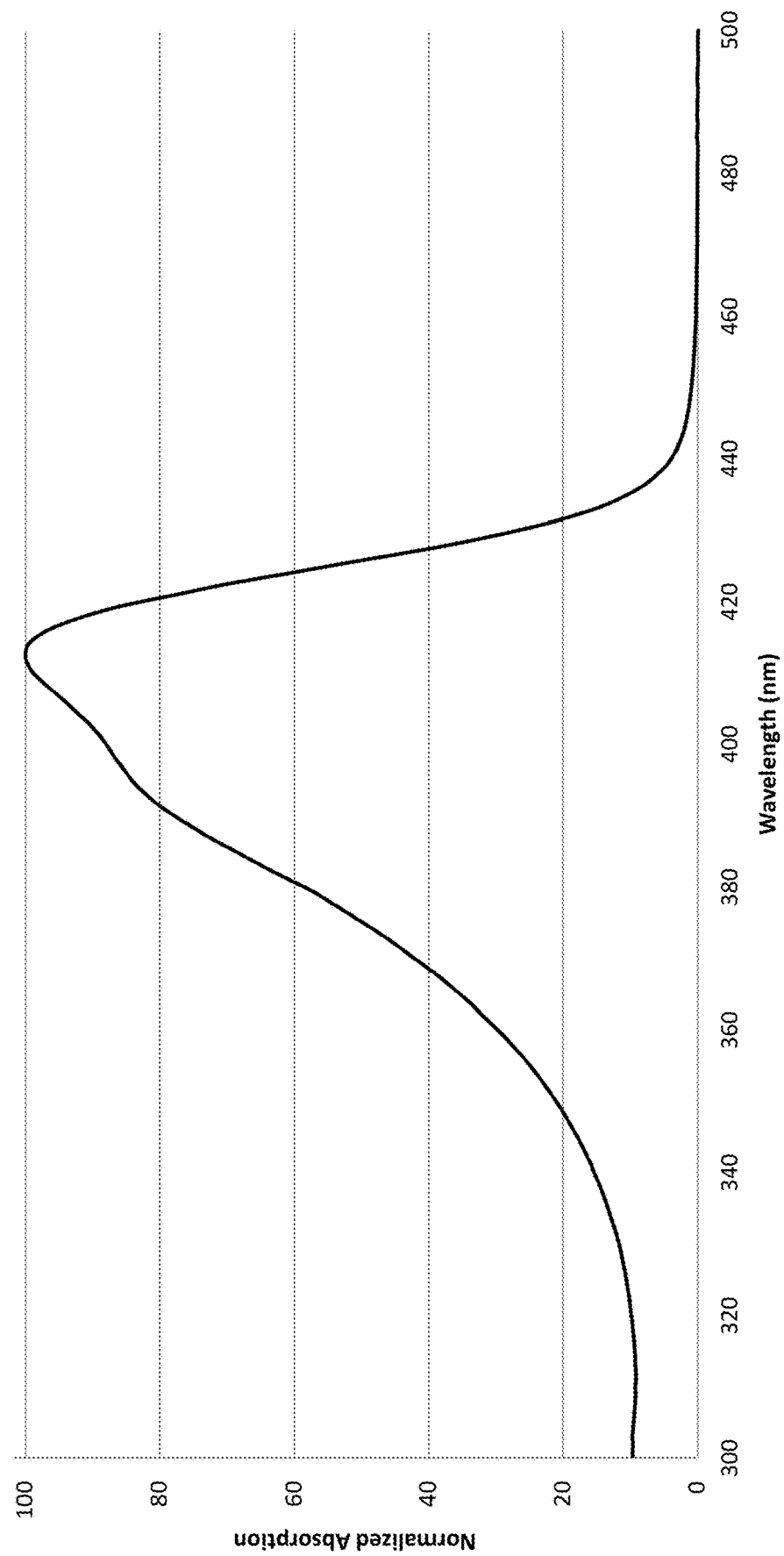
FIG. 1. The normalized absorption spectra of CPCP 11 in PBS buffer (pH=7.4).
Figure 2:
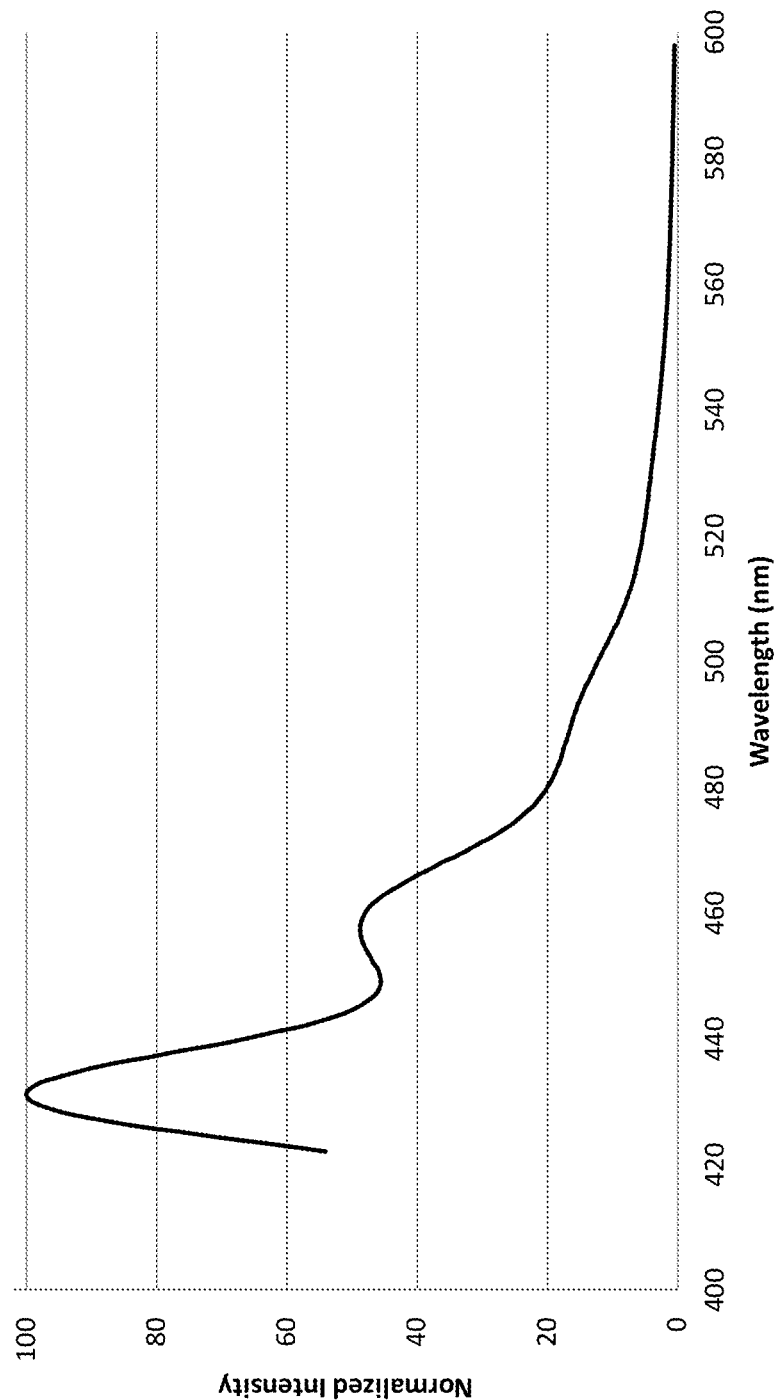
FIG. 2. The normalized fluorescence spectra of CPCP 11 in PBS buffer (pH=7.4).

Before the present invention is described in further detail, it is to be understood that this invention is not limited to the particular molecules, methodologies, devices, solutions or apparatuses described, as such methods, devices, solutions or apparatuses can, of course, vary. It is also to be understood that the terminology used herein is for the purpose of describing particular embodiments only, and is not intended to limit the scope of the present invention. The following definitions are set forth to illustrate and define the meaning and scope of the various terms used to describe the invention herein.

Use of the singular forms "a" "an" and "the" include plural references unless the context clearly dictates otherwise. Thus, for example, reference to "a probe" includes a plurality of probes, and the like. Additionally, use of specific plural references, such as "two" "three" etc., read on larger numbers of the same subject unless the context clearly dictates otherwise.

Terms such as "connected" "attached" "conjugated" and "linked" are used interchangeably herein and encompass direct as well as indirect connection, attachment, linkage or conjugation unless the context clearly dictates otherwise; in one example, the phrase "conjugated polymer" is used in accordance with its ordinary meaning in the art and refers to a polymer containing an extended series of unsaturated bonds, and that context dictates that the term "conjugated" should be interpreted as something more than simply a direct or indirect connection, attachment or linkage.

The term "alkyl" as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkylene" as employed herein, by itself or as part of another group, refers to straight, branched chain or cyclic divalent radicals having up to 50 carbons, unless the chain length or ring size is limited thereto. Typical examples include methylene (—CH$_2$—), ethylene (—CH$_2$CH$_2$—), propylene, butylene, pentylene, hexylene, heptylene, octylene, nonylene, and decylene, among others.

The term "alkenyl" as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene" as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH=CH—), propenylene (—CH=CHCH$_2$— and —CH$_2$CH=CH—), n-butenylene, and 3-methyl-2-pentenylene, hexenylene, heptenylene, octenylene, nonenylene, and decenylene, among others.

The term "alkynyl" as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡CH$_2$— and —CH$_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—OCH$_2$CH$_2$O—) or alkyl moieties that contain more than one oxygen atom.

The term "aryl" as employed herein, by itself or as part of another group, refers to an aryl or aromatic ring system containing 1 to 10 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of fluorenyl, phenyl, biphenyl, o-, m-, or p-terphenyl, 1-naphthyl, 2-naphthyl, 1-, 2-, or 9-anthryl, 1-, 2-, 3-, 4-, or 9-phenanthrenyl, 1-perylenyl, 1-ovalenyl, 1-benzoperyenyl, 1- or 2-chrysenyl, 1- or 2-hexahelicenyl, 1-corannulenyl, 1-coronenyl, 1-, 2- or 4-pyrenyl. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

The term "heteroaryl" as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups.

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

"Substituted" refers to a group in which one or more hydrogen atoms are independently replaced with the same or different substituent(s). Substituents of interest include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —O$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O) O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. When the group being substituted is an aryl or heteroaryl group, the substituent(s) (e.g., as described herein) may be referred to as "aryl substituent(s)".

The term "fluorescent dye or FD" as employed herein, by itself or as part of another group, refers to an aromatic or heteroaromatic moiety that emits fluorescence longer than 500 nm. The examples of fluorescent dyes include, but not limited to coumarins, fluoresceins, rhodamines, cyanines, bodipys, phthalocyanines, porphyrins, acridines, acridones, DDAO, carbazines, anthrancences, anthraquinones, DRAQ-5, azulenes, benzoxazinones, azacoumarins, benzoimidazoles, benzoxazoles, benzothiazoles, tetrapyrroles, diketopyrrolopyrrole, pyrazolines, hypericins, hypocrellins, perylenequinones, IR-140, luciferin, naphthamides, naphthalenes, naphthoquinones, NBD, SBD, oxazines, oxazoles, dapoxyls, osmium complexes, ruthenium complexes, platinum complexes, polycyclic dyes, pyrilium salts, nanocrystals, rhodoles, Schiff bases, squaraines, styryls, polythiophenes, tetrazolium salts or upconversion oxides.

The terms "halogen" or "halo" as employed herein, by itself or as part of another group, refers to chlorine, bromine, fluorine or iodine.

The terms "amino" or "amine" include $NH_2$, "monoalkylamine" or "monoalkylamino" and "dialkylamine" or "dialkylamino". The terms "monoalkylamine" and "monoalkylamino" "dialkylamine" and "dialkylamino as employed herein, by itself or as part of another group, refers to the group $NH_2$ where one hydrogen has been replaced by an alkyl group, as defined above.

The terms "dialkylamine" and "dialkylamino" as employed herein, by itself or as part of another group, refers to the group $NH_2$ where both hydrogens have been replaced by alkyl groups, as defined above.

The term "hydroxyalkyl" as employed herein, by itself or as part of another group, refers to an alkyl group where one or more hydrogens thereof are substituted by one or more hydroxyl moieties.

The term "haloalkyl" as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl" as employed herein, by itself or as part of another group, refers to an alkenyl group where one or more hydrogens thereof are substituted by one or more halo moieties.

The term "haloalkynyl" as employed herein, by itself or as part of another group, refers to an alkynyl group where one or more hydrogens thereof are substituted by one or more halo moieties.

The term "carboxyalkyl" as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The term "carboxy" as used herein, by itself or as part of another group, is represented by —COOW wherein W is a hydrogen, an alkali metal ion, an ammonium or other biologically compatible counter ion.

The term "sulfonate" as used herein, by itself or as part of another group, is represented by —S(=O)$_2$OW wherein W is a hydrogen, an alkali metal ion, an ammonium or other biologically compatible counter ion.

The term "phosphonate" as used herein, by itself or as part of another group, is represented by —P(=O)$O_2W_2$ wherein W is a hydrogen, an alkali metal ion, an ammonium or other biologically compatible counter ion.

The term "boronate" as used herein, by itself or as part of another group, is represented by —B(OW)$_2$ wherein W is a hydrogen, an alkali metal ion, an ammonium or other biologically compatible counter ion.

The term "ammonium" as used herein, by itself or as part of another group, is represented —N(R$_3$)X wherein n is 1-20, R is a short alkyl (e.g. $C_1$-$C_{12}$ alkyl); X is a biologically compatible anion such as F$^-$, Cl$^-$, Br$^-$ or I$^-$. Ammonium may include a nitrogen ring structure such as pyridinium, acridinium or quinlonium etc.

The term "sulfonium" as used herein, by itself or as part of another group, is represented —S(R$_2$)X wherein n is 1-20, R is a short alkyl (e.g. $C_1$-$C_{12}$ alkyl);
X is a biologically compatible anion such as F$^-$, Cl$^-$, Br$^-$ or I$^-$;

The term "phosphonium" as used herein, by itself or as part of another group, is represented —P(R$_3$)X wherein n is 1-20, R is a short alkyl (e.g. $C_1$-$C_{12}$ alkyl);
X is a biologically compatible anion such as F$^-$, Cl$^-$, Br$^-$ or I$^-$.

The term "polyethyleneglycol or PEG" as used herein, by itself or as part of another group, refers to a polymeric group including a chain described by the formula —(CH$_2$CH$_2$O—)$_n$— or a derivative thereof, where "n" is 5000 or less, such as 1000 or less, 500 or less, 200 or less, 100 or less, 50 or less, 40 or less, 30 or less, 20 or less, 15 or less, such as 2 to 30, 3 to 15, or 10 to 15. In some cases, n is 2-30. It is understood that the PEG polymeric group may be of any convenient length and may include a variety of terminal groups and/or further substituent groups, including but not limited to, alkyl (e.g., methyl), aryl, hydroxyl, amino, acyl, acyloxy, and amido terminal and/or substituent groups.

The term "water soluble group", "water solubilizing group" or "WSG" as used herein, by itself or as part of another group, refers to the moiety capable of increasing the water solubility of a polymer. The term WSG refers to a group that is well solvated in aqueous environments e.g., under physiological conditions, and that imparts improved water solubility upon the molecules to which it is attached. WSG include, but are not limited to PEG groups, carboxy, sulfonate, phosphonate, boronate, amine, ammonium, sulfonium, phosphonium, alcohol, or sugar. In general, one or more WSGs are attached as substituent or sidechain groups of comonomers of the conjugated polymer.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

The term "functional group or FG" as used herein, by itself or as part of another group, is a reactive moiety that can be used to covalently link polymers of the invention to a biological target. They include, but not limited to activated esters, acrylamides, acyl azides, acyl halides, acyl nitriles, aldehydes, ketones, alkyl halides. alkyl sulfonates, anhydrides, aryl halides, aziridines, boronates, carbodiimides, diazoalkanes, epoxides, haloacetamides, haloplatinate, halotriazines, imido esters, isocyanates, isothiocyanates, maleimides, phosphoramidites, silyl halides, sulfonate esters, sulfonyl halides, azides, 1,2,4,5-tetrazines, hydroxylamines, hydrazines, cysteines, azides, nitrile-N-oxides, anthracenes, amines, anilines, thiols, alcohols, phenols, carboxylic acids, glycols, heterocycles, alkynes, cyclooctynes, methyl 2-diphenylphosphinobenzonate, cycloalkynes, or DBCO. A FG can sometimes be referred to as a reactive FG or chemoselective functional group. Any convenient compatible functional groups can be used to conjugate molecules of interest to a conjugated polymer of this disclosure.

The term "end groups" as used herein, by itself or as part of another group, is the two moieties located on the two terminals of a polymer. They include, but not limited to hydrogen, bromo, iodo, boronyl or a FG.

The term "linker or L" as used herein, by itself or as part of another group, refers to a linking moiety that connects two groups and has a backbone of 100 atoms or less in length. A linker can be a spacer that links the polymer of this invention to a reactive moiety or a biological target. A linker may be a covalent bond or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), nbutyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. They include, but not limited to alkyl, alkylaryl, alkylheteroaryl, aryl, heteroaryl or a PEG. The term "conjugated polymer" as used herein, by itself or as part of another compound, is a polymer containing an extended series of randomly interconnected unsaturated bonds, aryls and/or heteroaryls.

The term "biological substrate or BS" as used herein, by itself or as part of another group, is a biological target molecule or biomolecule. They include, but not limited to antibodies, antigens, proteins, peptides, oligonucleotides, DNA, RNA, PNA, aptamers, sugars, antibiotics, metabolites, cAMP, cGMP, polysaccharides, viruses, cells and tissues.

The term "sample" refers to a material or mixture of materials, in some cases in liquid form, containing one or more analytes of interest. The term can refer to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample".

The terms "determining," "measuring," and "assessing," and "assaying" are used interchangeably and include both quantitative and qualitative determinations.

It is noted that in this disclosure and particularly in the claims and/or paragraphs, terms such as "comprises" "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

DETAILED DESCRIPTION

The present invention discloses a new type of fluorescent conjugated polymer that finds use in preparing biological conjugates, and that has desirable properties, such as: (1) high fluorescence quantum yield; (2) red-shifted emission; (3) high water solubility; (4) high linearity; (5) high planarity; (6) high fluorescence resonance energy transfer (FRET) efficiency when a second dye coupled to the polymer; and (7) high photostability.

The present disclosure provides a water-soluble conjugated polymer containing a conjugated segment having the structure of Formula 1:

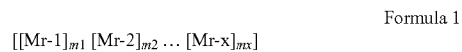

Formula 1 wherein the polymer comprises x different comonomer units (Mr-1 to Mr-x) that are distributed (e.g., randomly) along the polymer main chain or backbone; wherein Mr-1 is a condensed polycyclic aromatic or heteroaromatic comonomer containing four or more 5-membered and/or 6-membered rings (e.g., as described herein); wherein Mr-2 to Mr-x are different and distinct comonomers that are independently a double bond, a triple bond, an aryl, or a heteroaryl; m1 is an integer larger than 5, m2 to mx are integers from 0 to 200, provided that (1). the sum of m1 to mx is ≥10; and
(2). at least one of Mr1 to Mr-X has a WSG; and
(3). optionally at least one of Mr1 to Mr-X has a FG or a L-BS.

It is understood the conjugated polymers described herein can include end groups that cap the terminal co-monomer units. The polymers of this invention may be capped on the two terminals by H, a phenyl, a substituted phenyl, an aryl, a substituted aryl, a substituted heteroaryl, or a heteroaryl. The end group can be optionally substituted by bromo, iodo, boronyl, a -L-FG or a L-BS. They are preferably capped with a phenyl, substituted phenyl, a fluorene or a substituted analog.

The polycyclic aromatic comonomers of the conjugated polymers of this disclosure contain four or more condensed or interconnected 5-membered and/or 6-membered rings. These polycyclic aromatic ring systems can have at least 3 or 4 aromatic rings condensed or interconnected (e.g., fused) with a configuration that provides a conjugated system. In some cases, two or three 6 membered aryl or heteroaryl rings are linked via intervening fused 5-membered carbocyclic or heterocyclic rings. The polycyclic aromatic ring system includes a conjugated backbone suitable for incorporation into a conjugated polymer.

The conjugated polymers of this disclosure include polycyclic aromatic comonomers that provide structures capable of harvesting light with particular absorption maximum wavelengths and converting it to emitted light at longer emission maximum wavelengths. The conjugated polymers are fluorescent. Conjugated polymers (CPs) are characterized by a delocalized electronic structure where the backbone contains conjugated comonomer units. The conjugated polymers can be efficient light harvesting molecules and provide for optical amplification via Forster resonance energy transfer (FRET) to an acceptor fluorescent dye in close proximity. Such energy transfer mechanisms from donor conjugated polymer to acceptor dye are relatively short range. The polycyclic aromatic comonomers can provide conjugated polymers with spectral properties that have absorption maximum peak longer than 260 nm, and emission maximum peak longer than 300 nm. These polycyclic aromatic monomers can have fluorescence quantum yield larger than 10%. Some of them are selectively listed in Table 1 as examples without limiting the scope of this invention.

Table 1. Exemplary Mr-1 co-monomers that can be utilized in the conjugated polymers of this disclosure. Each R substituent represents a sidechain group which can be incorporated into the comonomer to impart desirable properties on the co-monomer and resulting conjugated polymers, e.g., increased water solubility, or conjugation site, e.g., to a fluorescent dye or biomolecule. In some embodiments, each R is independently selected from H, alkyl, substituted alkyl, linker, WSG, -L-WSG, -L-FG, and -L-BS. It is understood that any of the comonomer structures described in Table 1 may further include one or more aryl substituents in addition to the depicted R substituent side groups:

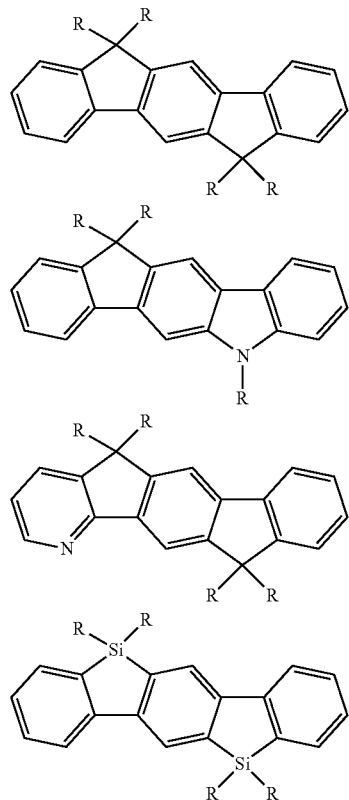

-continued

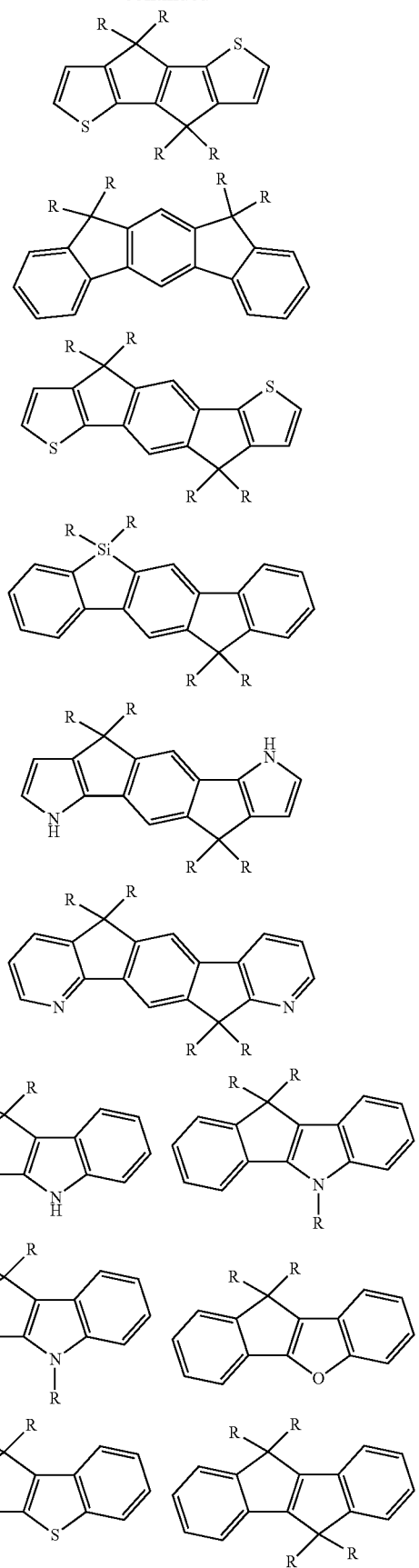

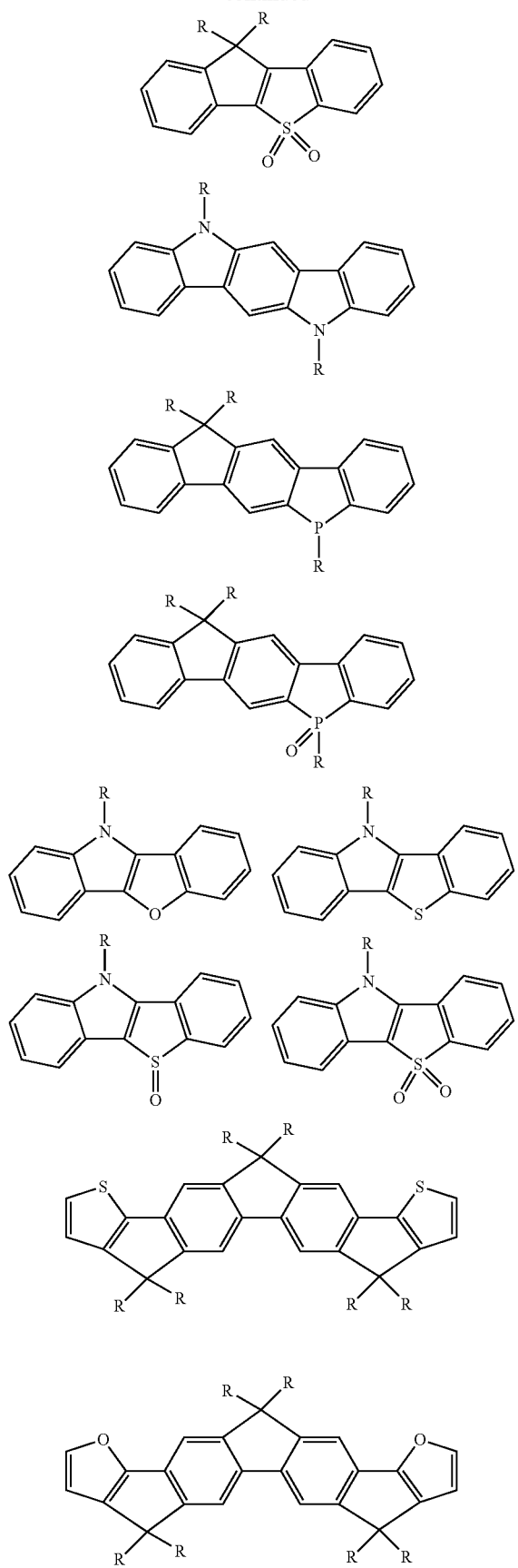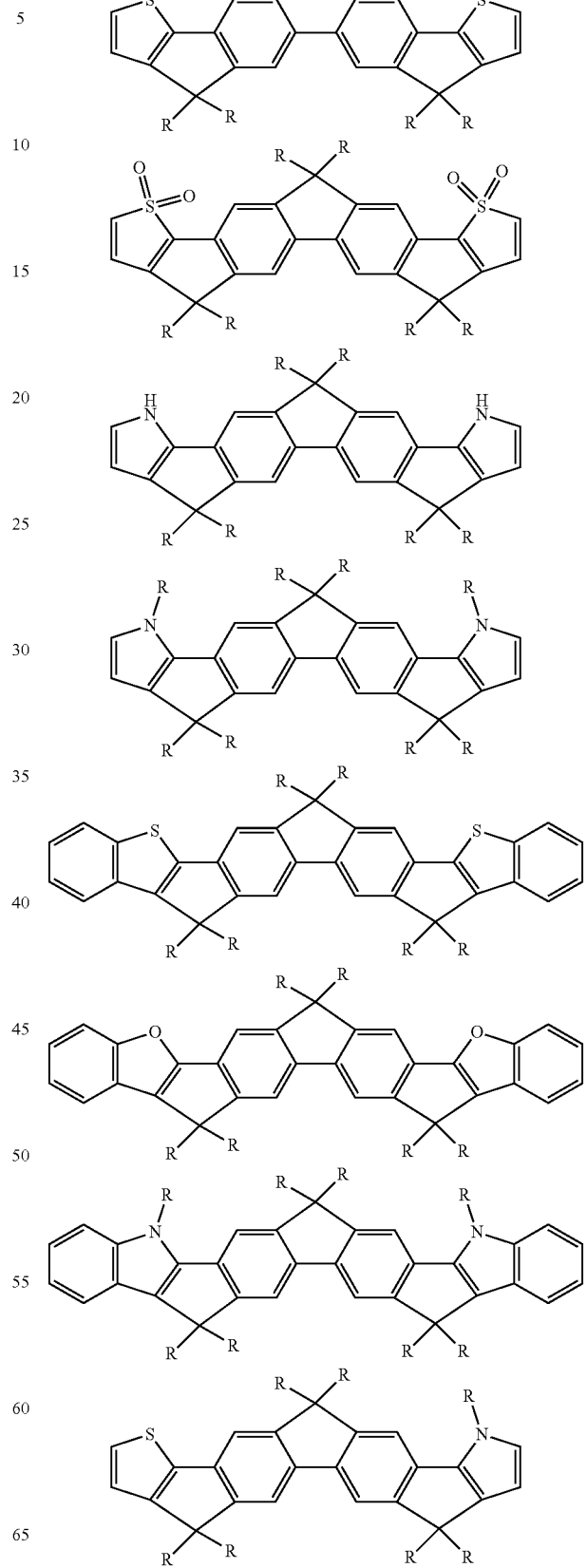

-continued

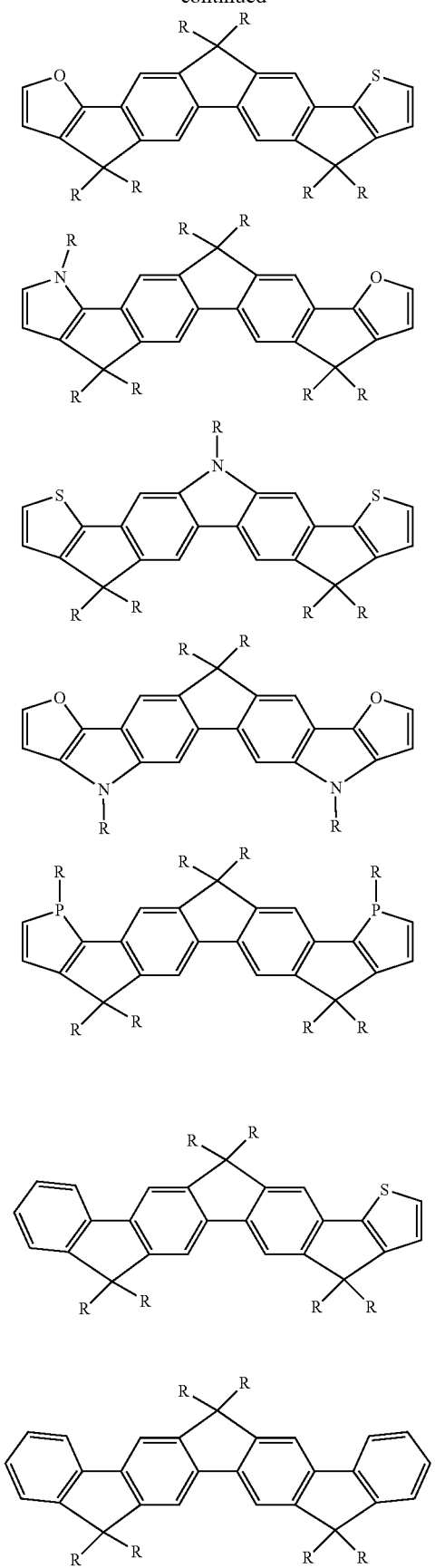

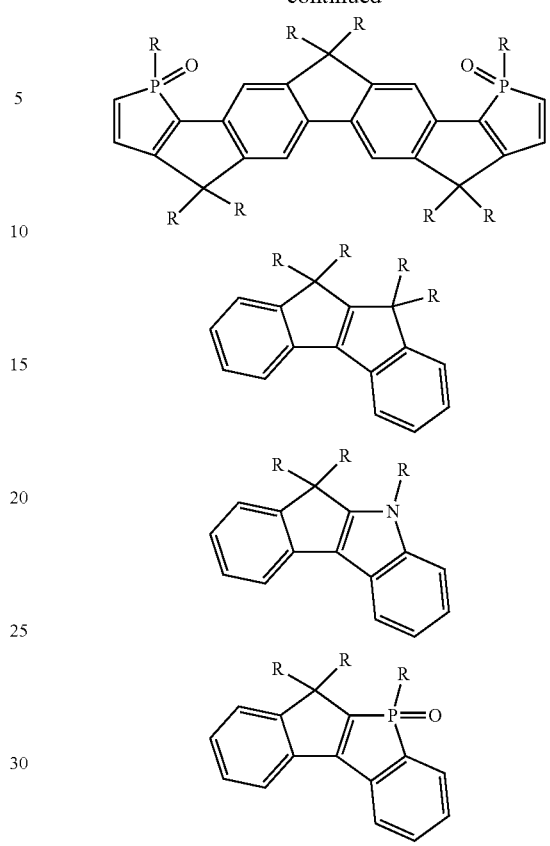

The conjugated polymers include x distinct types of co-monomer units arranged along the polymer backbone, where multiple units of each distinct co-monomer type may be present. In some cases, x is 10 or less, such as 9, 8, 7, 6, 5, 4, 3, or 2. In certain embodiments, x is 1 such that the conjugated polymer includes only Mr-1 comonomers. It is understood that depending on the method of preparation, a variety of arrangements of co-monomers are possible in the conjugated polymer, e.g., random or coblock configurations. In some embodiments, the comonomers are arranged randomly along the backbone. In such cases, the resulting conjugated polymers can be represented by a formula showing the numbers or mol % of each comonomer unit.

In some embodiments, the conjugated polymer is composed of 5 mol % or greater of Mr-1 comonomers, such as 10 mol % or greater, 15 mol % or greater, 20 mol % or greater, 25 mol % or greater, or even more.

In some embodiments of formula 1, Mr-1 is of Formula 2a or Formula 2b:

Formula 2a

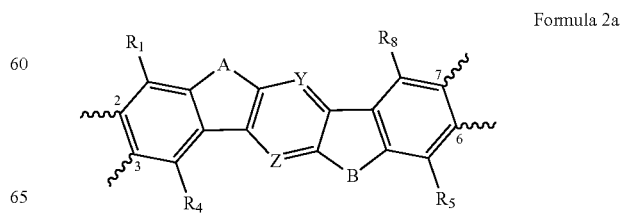

-continued

Formula 2b

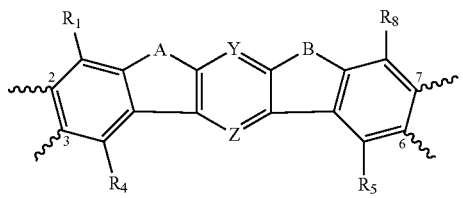

wherein:
the Mr-1 comonomer units are connected to adjacent comonomers of the conjugated polymer backbone through any two positions of C2, C3, C6 and C7 of the Mr-1 comonomer;

$R_1$ to $R_8$ are independently selected from hydrogen, halogen, an alkyl, a WSG, an aryl, a heteroaryl group, a FD, a FG, and L-BS;

A and B are independently selected from O, S, N—$R_{11}$, P—$R_{11}$, O═P—$R_{11}$, O═P—$OR_{11}$, $R_{11}$—C—$R_{12}$, $R_{11}$—Si—$R_{12}$, O═S—$R_{11}$, and O═S(O)—$R_{11}$, wherein $R_{11}$ and $R_{12}$ are independently selected from hydrogen, an alkyl, a WSG, an aryl, a heteroaryl group, a FD, a FG, and L-BS; and Y and Z are independently selected from none, C, O, S, N, N—$R_{13}$, P, P—$R_{13}$, O═P—$R_{13}$, O═P—$OR_{13}$, O═S—$R_{13}$, and O═S(O)—$R_{13}$ wherein $R_{13}$ and $R_{14}$ independently represent hydrogen, an alkyl, a WSG, an aryl, a heteroaryl group, a FD, a FG, or a L-BS;

with the proviso that at least one of A, B, Y and Z is a heteroatom.

In some embodiments of formula 2a, the Mr-1 comonomer units are connected to adjacent comonomers of the conjugated polymer backbone through positions C2 and C7 of the Mr-1 comonomer. It is understood that in Formula 2a-11a, at the numbered positions 1-3 and 6-7, an R substituent (i.e., $R_1$, $R_2$, $R_3$, $R_6$ or $R_7$) may be present at those positions which are no conjugated to an adjacent comonomer or terminal end group. For example, in some embodiments of Formula 2a and 2b, Mr-1 has one of the structures Formula 3a and 3b:

Formula 3a

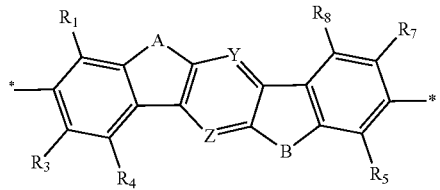

Formula 3b

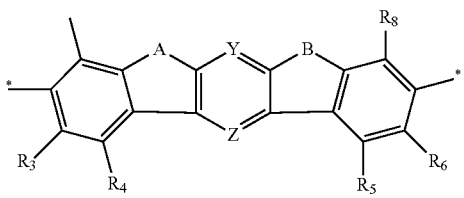

where * indicates point of attachment to adjacent co-monomers or a terminal end group and $R_3$ and $R_6$ are as defined above. In some embodiments of formula 3a, the Mr-1 comonomer units are connected to adjacent comonomers of the conjugated polymer backbone through positions C3 and C6 of the Mr-1 comonomer, and formula 3a includes groups $R_2$ and $R_6$ are positions C2 and C6.

In some embodiments of formula 1 Mr-1 is of Formula 4a or Formula 4b:

Formula 4a

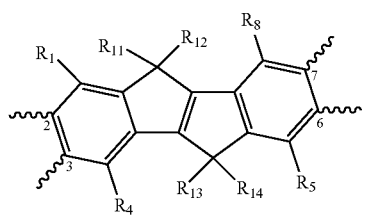

Formula 4b

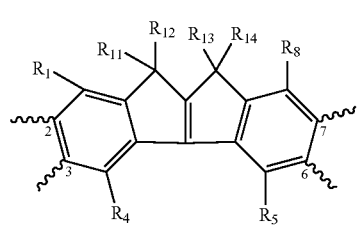

wherein:
the Mr-1 comonomer units are connected to adjacent comonomers of the conjugated polymer backbone through position C2/C3 and position C6/C7 of the Mr-1 comonomer;

$R_1$ to $R_8$ are independently selected from hydrogen, halogen, an alkyl, a WSG, an aryl, a heteroaryl group, a FD, a FG, and L-BS;

$R_{11}$ to $R_{14}$ are independently selected from hydrogen, an alkyl, a WSG, an aryl, a heteroaryl group, a FD, a FG, and L-BS; and Mr-2 to Mr-x are independently, optionally substituted with a FG or L-BS; wherein at least one of $R_{11}$ to $R_{14}$ is a WSG.

In some embodiments of formula 4a and 4b, the Mr-1 comonomer units are connected to adjacent comonomers of the conjugated polymer backbone through positions C2 and C6 or C7 of the Mr-1 comonomer:

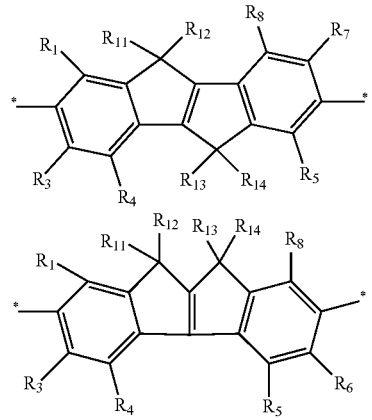

In some embodiments of formula 4a and 4b, the Mr-1 comonomer units are connected to adjacent comonomers of the conjugated polymer backbone through positions C3 and C6 or C7 of the Mr-1 comonomer.

In some embodiments of formula 1, Mr-1 is of Formula 6a or Formula 6b:

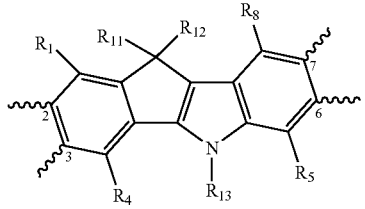

Formula 6a

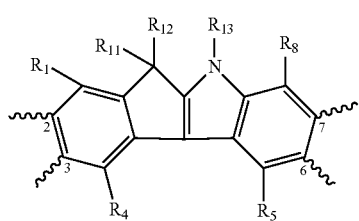

Formula 6b wherein:
the Mr-1 comonomer units are connected to adjacent monomers of the conjugated polymer backbone through position C2/C3 and position C6/C7 of the Mr-1 comonomer;
$R_1$ to $R_8$ are independently selected from hydrogen, a halogen, an alkyl, a WSG, an aryl, a heteroaryl group, a FD, a FG, and L-BS;
$R_{11}$ to $R_{13}$ are independently selected from hydrogen, an alkyl, a WSG, an aryl, a heteroaryl group, a FD, a FG, and L-BS;
Mr-2 to Mr-x are independently, optionally substituted by a FG or L-BS;
wherein at least one of $R_{11}$ to $R_{13}$ is a WSG.

In some embodiments of formula 6a and 6b, the Mr-1 comonomer units are connected to adjacent comonomers of the conjugated polymer backbone through positions C2 and C7 of the Mr-1 comonomer. In some embodiments of formula 6a and 6b, the Mr-1 comonomer units are connected to adjacent comonomers of the conjugated polymer backbone through positions C2 and C6 of the Mr-1 comonomer. In some embodiments of formula 6a and 6b, the Mr-1 comonomer units are connected to adjacent comonomers of the conjugated polymer backbone through positions C3 and C6 of the Mr-1 comonomer. In some embodiments of formula 6a and 6b, the Mr-1 comonomer units are connected to adjacent comonomers of the conjugated polymer backbone through positions C3 and C7 of the Mr-1 comonomer.

In some embodiments of formula 1, Mr-1 is of Formula 7a:

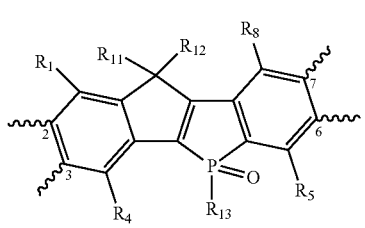

Formula 7a wherein:
the Mr-1 comonomer units are connected to adjacent monomers of the conjugated polymer backbone through position C2/C3 and position C6/C7 of the Mr-1 comonomer;
$R_1$ to $R_8$ are independently selected from hydrogen, a halogen, an alkyl, a WSG, an aryl, a heteroaryl group, a FD, a FG, and L-BS;
$R_{11}$ to $R_{13}$ are independently selected from hydrogen, an alkyl, a WSG, an aryl, a heteroaryl group, a FD, a FG, and L-BS; and
Mr-2 to Mr-x are independently, optionally substituted with a FG, or a L-BS;
wherein at least one of $R_{11}$ to $R_{13}$ is a WSG.

In some embodiments of formula 7a, the Mr-1 comonomer units are connected to adjacent comonomers of the conjugated polymer backbone through positions C2 and C7 of the Mr-1 comonomer. In some embodiments of formula 7a, the Mr-1 comonomer units are connected to adjacent comonomers of the conjugated polymer backbone through positions C3 and C6 of the Mr-1 comonomer.

In some embodiments of formula 1, Mr-1 is of Formula 8a:

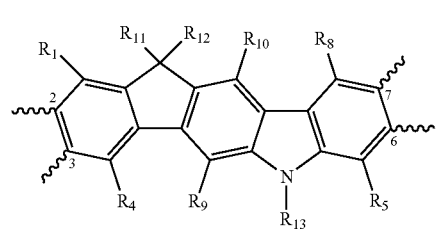

Formula 8a wherein:
the Mr-1 comonomer units are connected to adjacent monomers of the conjugated polymer backbone through position C2/C3 and position C6/C7 of the Mr-1 comonomer;
$R_1$ to $R_8$ are independently selected from hydrogen, a halogen, an alkyl, a WSG, an aryl, a heteroaryl group, a FD, a FG, and L-BS;
$R_{11}$ to $R_{13}$ are independently selected from hydrogen, an alkyl, a WSG, an aryl, a heteroaryl group, a FD, a FG, and L-BS; and
Mr-2 to Mr-x are independently, optionally substituted by a FG, or a L-BS;
wherein at least one of $R_{11}$ to $R_{13}$ is a WSG.

In some embodiments of formula 8a, the Mr-1 comonomer units are connected to adjacent comonomers of the conjugated polymer backbone through positions C2 and C7 of the Mr-1 comonomer. In some embodiments of formula 8a, the Mr-1 comonomer units are connected to adjacent comonomers of the conjugated polymer backbone through positions C3 and C6 of the Mr-1 comonomer.

In some embodiments of formula 1, Mr-1 is of Formula 9a:

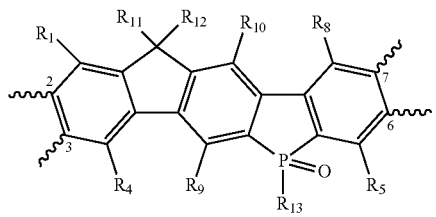

Formula 9a wherein:
the Mr-1 comonomer units are connected to adjacent monomers of the conjugated polymer backbone through position C2/C3 and position C6/C7 of the Mr-1 comonomer;
$R_1$ to $R_8$ are independently selected from hydrogen, a halogen, an alkyl, a WSG, an aryl, a heteroaryl group, a FD, a FG, and L-BS;
$R_{11}$ to $R_{13}$ are independently selected from hydrogen, an alkyl, a WSG, an aryl, a heteroaryl group, a FD, a FG, and L-BS; and
Mr-2 to Mr-x are independently, optionally substituted with a FG, or a L-BS;
wherein at least one of $R_{11}$ to $R_{13}$ is a WSG.

In some embodiments of formula 9a, the Mr-1 comonomer units are connected to adjacent comonomers of the conjugated polymer backbone through positions C2 and C7 of the Mr-1 comonomer. In some embodiments of formula 9a, the Mr-1 comonomer units are connected to adjacent comonomers of the conjugated polymer backbone through positions C3 and C6 of the Mr-1 comonomer.

In some embodiments of formula 1, Mr-1 is of Formula 10a:

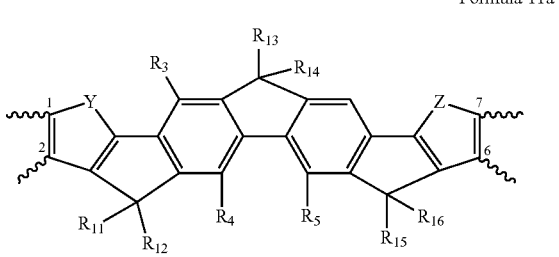

Formula 10a wherein:
the Mr-1 comonomer units are connected to adjacent monomers of the conjugated polymer backbone through position C1/C2 and C6/C7 of the Mr-1 comonomer;
$R_2$ to $R_6$ are independently selected from hydrogen, a halogen, an alkyl, a WSG, an aryl, a heteroaryl group, a FD, a FG, and L-BS;
A', B' and C' are independently selected from O, S, N—$R_{11}$, P—$R_{11}$, O=P—$R_{11}$, O=P—O$R_{11}$, $R_{11}$—C—$R_{12}$, $R_{11}$—Si—$R_{12}$, O=S—$R_{11}$, and O=S(O)—$R_{11}$ wherein $R_{11}$ and $R_{12}$ are independently selected from hydrogen, an alkyl, a WSG, an aryl, a heteroaryl group, a FD, a FG, and L-BS;
Y and Z are independently selected from O, S, N—$R_{13}$, P—$R_{13}$, O=P—$R_{13}$, O=P—O$R_{13}$, O=S—$R_{13}$, and O=S(O)—$R_{13}$ wherein $R_{13}$ is hydrogen, an alkyl, a WSG, an aryl, a heteroaryl group, a FD, a FG, or L-BS;
Mr-2 to Mr-x are independently, optionally substituted with a FG, or L-BS
wherein at least one of A', B' and C' comprises a WSG.

In some embodiments of formula 10a, the Mr-1 comonomer units are connected to adjacent comonomers of the conjugated polymer backbone through positions C1 and C7 of the Mr-1 comonomer. In some embodiments of formula 10a, the Mr-1 comonomer units are connected to adjacent comonomers of the conjugated polymer backbone through positions C2 and C6 of the Mr-1 comonomer.

In some embodiments of formula 1, Mr-1 is of Formula 11a:

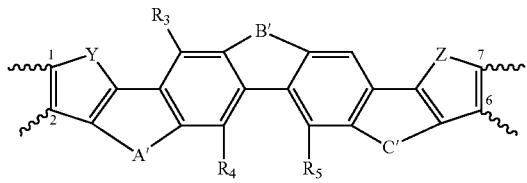

Formula 11a wherein: the Mr-1 comonomer units are connected to adjacent monomers of the conjugated polymer backbone through positions C1/C2 and C7/C6 of the Mr-1 comonomer; and at least two of $R_{11}$ to $R_{16}$ is a WSG.

In some embodiments of formula 11a, the Mr-1 comonomer units are connected to adjacent comonomers of the conjugated polymer backbone through positions C1 and C7 of the Mr-1 comonomer. In some embodiments of formula 11a, the Mr-1 comonomer units are connected to adjacent comonomers of the conjugated polymer backbone through positions C2 and C6 of the Mr-1 comonomer.

The Mr-2 to Mr-x comonomers of the invention typically contains at least one double bond or one triple bond that provides for pi-conjugation to adjacent co-monomers in the conjugated polymer backbone. In some embodiments, one of the comonomers is ethenylene (—CH=CH—) or substituted ethenylene. In some embodiments, one of the comonomers is acetylene (—CC—). In some embodiments, the co-monomer is an optionally substituted aryl or heteroaryl co-monomer. The Mr-2 to Mr-x comonomers may be selected to impart a desirable absorption wavelength upon the resulting conjugated polymer. Exemplary comonomer groups include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl, perylenyl, thienyl, benzo[b]thienyl, naphtho[2,3-b]thienyl, thianthrenyl, furyl, pyranyl, isobenzofuranyl, benzoxazolyl, chromenyl, xanthenyl, phenoxathinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl. In some embodiments, an optionally substituted aryl or heteroaryl co-monomer is selected from substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl.

The conjugated polymer may have any convenient length. In some cases, the total number of monomeric repeating units of the conjugated polymer may fall within the range of 5 to 10,000, 10 to 10,000, 100 to 10,000 units or segments. In some embodiments, the total number of monomeric repeating units of the conjugated polymer may fall within the range of 5 to 1,000, such as 5 to 500, 5 to 400, 5 to 300, 5 to 200, or 5 to 100 units. The length of the conjugated polymer can be determined by the total numbers (mx) of each type of co-monomer (Mr-x) present in the polymer backbone. In some embodiments of formula 1, the sum of m1 to mx is 10 or more, such as 20 or more, 30 or more, 40 or more, 50 or more, 100 or more, up to 10,000 or less, such as up to 5000, up to 2000 or up to 1000.

The subject conjugated polymer may be water soluble, or comprise a plurality of WSGs. Any convenient water solubilizing groups (WSGs) may be included in the to provide for increased water-solubility. While the increase in solubility may vary, in some cases the increase is 2 fold or more, e.g., 5 fold, 10 fold, 25 fold, 50 fold, 100 fold or more as compared to the polymer without the WSGs. The WSGs may be charged, e.g., positively or negatively charged. In certain cases, the WSG is a neutral hydrophilic group. In some embodiments, the WSG is a hydrophilic polymer, e.g., a polyethylene glycol, a cellulose, a chitosan, or a derivative thereof. The WSG may be attached via a linker. WSGs of interest include, but are not limited to, carboxylate, phosphonate, phosphate, sulfonate, sulfate, sulfinate, sulfonium, ester, polyethylene glycols (PEG) and modified PEGs, hydroxyl, amine, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{zz}$, and R$^{zz}$ and R$^{YY}$ are independently selected from H and C$_{1-3}$ alkyl.

Multiple WSGs may be included at a single location via a branching linker. In some embodiments, the conjugated polymer includes substituent(s) selected from an alkyl, an aralkyl and a heterocyclic group, each group further substituted with a include water solubilizing groups hydrophilic polymer group, such as a polyethylglycol (PEG) (e.g., a PEG of 2-20 units).

In some embodiments, the conjugated polymer itself is used as a fluorescent molecule for detecting target analytes. In some embodiments, the conjugated polymer is linked to a fluorescent dye, e.g., a conventional small molecule dye, such that FRET can occur from the donor polymer to the acceptor dye. The dye can be linked or configured in energy receiving proximity to the conjugated polymer. The acceptor fluorescent dye can be selected to provide for a desirable emission wavelength from the resulting donor polymer-acceptor dye conjugate.

The fluorescent dyes (FDs) linked to the conjugated polymers of the invention is typically a FD that has absorption maximum longer than 400 nm, and emission maximum longer than 450 nm with fluorescence quantum yield larger than 10%. They are typically selected from coumarins, styryls, fluoresceins, rhodamines, cyanines, BODIPYs or other polycyclic aromatics. Many of them are commercially available as selectively listed in Table 2 as examples.

TABLE 2

Exemplary acceptor fluorescent dyes (FDs) that can be linked to the conjugated polymers

| Fluorophore | Absorption (nm) | Emission (nm) |
|---|---|---|
| ATTO 465 | 453 | 508 |
| ATTO 488 | 501 | 523 |
| ATTO 495 | 495 | 527 |
| ATTO 514 | 511 | 533 |
| ATTO 532 | 532 | 553 |
| ATTO 550 | 554 | 576 |
| ATTO 565 | 563 | 592 |
| ATTO 590 | 594 | 624 |
| ATTO 594 | 601 | 627 |
| ATTO 610 | 615 | 634 |
| ATTO 620 | 619 | 643 |
| ATTO 633 | 629 | 657 |
| ATTO 647 | 645 | 669 |
| ATTO 647N | 644 | 669 |
| ATTO 655 | 663 | 684 |
| ATTO 665 | 663 | 684 |
| ATTO 680 | 680 | 700 |
| ATTO 700 | 700 | 719 |
| ATTO 725 | 729 | 752 |
| ATTO 740 | 740 | 764 |
| 5-carboxy-2,7-dichlorofluorescein | 504 | 529 |
| 5-Carboxyfluorescein (5-FAM) | 492 | 518 |
| 5-Carboxynapthofluorescein | 598 | 668 |
| 5-Carboxytetramethylrhodamine (5-TAMRA) | 542 | 568 |
| 5-FAM (5-Carboxyfluorescein) | 492 | 518 |
| 5-ROX | 578 | 604 |
| 6-TAMRA | 548 | 568 |
| 6-Carboxyrhodamine 6G | 518 | 543 |
| 6-CR6G | 518 | 543 |
| 6-JOE | 520 | 548 |
| 6-FAM | 494 | 517 |
| 6-ROX | 570 | 591 |
| Alexa Fluor 488 | 492 | 520 |
| Alexa Fluor 532 | 532 | 554 |
| Alexa Fluor 546 | 557 | 573 |
| Alexa Fluor 568 | 578 | 603 |
| Alexa Fluor 594 | 594 | 618 |
| Alexa Fluor 633 | 632 | 650 |
| Alexa Fluor 647 | 647 | 666 |
| Alexa Fluor 660 | 668 | 698 |
| Alexa Fluor 680 | 679 | 702 |
| Bodipy 492/515 | 490 | 515 |
| Bodipy 493/503 | 533 | 549 |
| Bodipy 500/510 | 509 | 515 |
| Bodipy 505/515 | 502 | 510 |
| Bodipy 530/550 | 528 | 547 |
| Bodipy 542/563 | 543 | 563 |
| Bodipy 558/568 | 558 | 569 |
| Bodipy 564/570 | 564 | 570 |
| Bodipy 576/589 | 579 | 590 |
| Bodipy 581/591 | 584 | 592 |
| Bodipy 630/650-X | 625 | 642 |
| Bodipy 650/665-X | 647 | 665 |
| Bodipy 665/676 | 605 | 676 |
| Bodipy Fl | 505 | 513 |
| Bodipy R6G SE | 528 | 547 |
| Bodipy TMR | 542 | 574 |
| Bodipy TR | 589 | 617 |
| CF 488A | 490 | 515 |
| CF 555 | 555 | 565 |
| CF 568 | 562 | 583 |
| CF 594ST | 593 | 614 |
| CF 633 | 630 | 650 |
| CF 640R | 642 | 662 |
| CF 647 | 650 | 665 |
| CF 660C | 667 | 685 |
| CF 680 | 681 | 698 |
| CF680R | 680 | 701 |
| CF 750 | 755 | 777 |
| CF 770 | 770 | 797 |
| CF 790 | 784 | 806 |
| CL-NERF | 504 | 540 |
| CMFDA | 494 | 520 |
| Cy2 | 489 | 506 |

TABLE 2-continued

Exemplary acceptor fluorescent dyes (FDs) that can be linked to the conjugated polymers

| Fluorophore | Absorption (nm) | Emission (nm) |
|---|---|---|
| Cy3 | 554 | 568 |
| Cy3.5 | 581 | 598 |
| Cy5 | 649 | 666 |
| Cy5.5 | 675 | 695 |
| Cy7 | 743 | 767 |
| DDAO | 646 | 659 |
| DiA | 456 | 591 |
| DiD | 644 | 665 |
| DiI | 549 | 565 |
| DyLight 488 | 493 | 518 |
| DyLight 550 | 562 | 576 |
| DyLight 594 | 593 | 618 |
| DyLight 633 | 638 | 568 |
| DyLight 650 | 652 | 672 |
| DyLight 680 | 692 | 712 |
| DyLight 755 | 754 | 776 |
| DyLight 800 | 777 | 794 |
| DiO | 487 | 502 |
| DiR | 748 | 780 |
| DM-NERF | 497 | 540 |
| DsRed | 558 | 583 |
| DTAF | 494 | 520 |
| DY-490 | 491 | 515 |
| DY-495 | 494 | 521 |
| DY-505 | 507 | 528 |
| DY-530 | 533 | 554 |
| DY-547 | 558 | 573 |
| DY-548 | 558 | 572 |
| DY-549 | 562 | 577 |
| DY-549P1 | 563 | 578 |
| DY-550 | 562 | 577 |
| DY-554 | 544 | 570 |
| DY-555 | 547 | 573 |
| DY-556 | 548 | 574 |
| DY-560 | 560 | 578 |
| DY-590 | 581 | 600 |
| DY-591 | 581 | 598 |
| DY-594 | 594 | 615 |
| DY-605 | 600 | 624 |
| DY-610 | 610 | 632 |
| DY-615 | 623 | 643 |
| DY-630 | 638 | 658 |
| DY-631 | 637 | 657 |
| DY-632 | 636 | 658 |
| DY-633 | 638 | 658 |
| DY-634 | 636 | 657 |
| DY-635 | 648 | 670 |
| DY-636 | 647 | 670 |
| DY-647 | 653 | 673 |
| DY-648 | 655 | 676 |
| DY-649 | 656 | 670 |
| DY-649P1 | 654 | 672 |
| DY-650 | 656 | 676 |
| DY-651 | 655 | 677 |
| DY-652 | 653 | 676 |
| DY-654 | 653 | 677 |
| DY-675 | 675 | 699 |
| DY-676 | 675 | 699 |
| DY-677 | 674 | 698 |
| DY-678 | 674 | 694 |
| DY-679 | 679 | 698 |
| DY-679P1 | 679 | 697 |
| DY-680 | 691 | 709 |
| DY-681 | 692 | 709 |
| DY-682 | 692 | 709 |
| DY-700 | 707 | 728 |
| DY-701 | 709 | 730 |
| DY-703 | 705 | 721 |
| DY-704 | 706 | 721 |
| DY-730 | 734 | 755 |
| DY-731 | 736 | 755 |
| DY-732 | 735 | 756 |
| DY-734 | 733 | 755 |
| DY-749 | 759 | 780 |
| DY-750 | 751 | 774 |
| DY-751 | 752 | 772 |
| DY-752 | 750 | 771 |
| DY-754 | 748 | 771 |
| DY-776 | 772 | 787 |
| DY-777 | 770 | 788 |
| DY-778 | 767 | 787 |
| DY-780 | 783 | 799 |
| DY-781 | 784 | 796 |
| DY-782 | 785 | 794 |
| DY-800 | 777 | 791 |
| DY-831 | 844 | 875 |
| Eosin | 524 | 545 |
| Erythrosin | 529 | 555 |
| FITC | 490 | 520 |
| Fluo-3 | 506 | 520 |
| Fluo-4 | 494 | 516 |
| Fluor-Ruby | 555 | 582 |
| FluorX | 494 | 520 |
| FM 1-43 | 479 | 598 |
| FM 4-46 | 515 | 640 |
| iFluor 488 | 498 | 520 |
| iFluor 555 | 558 | 578 |
| iFluor 594 | 588 | 610 |
| iFluor 647 | 649 | 670 |
| iFluor 680 | 686 | 702 |
| iFluor 700 | 696 | 720 |
| iFluor 750 | 755 | 785 |
| iFluor 780 | 787 | 808 |
| Lyso Tracker Green | 504 | 511 |
| Lyso Tracker Yellow | 551 | 576 |
| Mitotracker Green | 490 | 599 |
| Mitotracker Orange | 551 | 576 |
| Mitotracker Red | 578 | 516 |
| NBD | 466 | 539 |
| Oregon Green 488 | 494 | 517 |
| Oregon Green 514 | 506 | 526 |
| PKH26 | 551 | 567 |
| PKH67 | 496 | 520 |
| Resorufin | 571 | 584 |
| RH 414 | 532 | 716 |
| Rhod-2 | 552 | 576 |
| Rhodamine | 550 | 573 |
| Rhodamine 110 | 496 | 520 |
| Rhodamine 123 | 507 | 529 |
| Rhodamine 6G | 525 | 555 |
| Rhodamine B | 540 | 625 |
| Rhodamine Green | 502 | 527 |
| Rhodamine Red | 570 | 590 |
| Rose Bengal | 525 | 550 |
| Spectrum Green | 497 | 538 |
| Spectrum Orange | 559 | 588 |
| Spectrum Red | 587 | 612 |
| SYTO 11 | 508 | 527 |
| SYTO 12 | 499 | 522 |
| SYTO 13 | 488 | 509 |
| SYTO 14 | 517 | 549 |
| SYTO 15 | 516 | 546 |
| SYTO 16 | 488 | 518 |
| SYTO 17 | 621 | 634 |
| SYTO 18 | 490 | 507 |
| SYTO 20 | 512 | 530 |
| SYTO 21 | 494 | 517 |
| SYTO 22 | 515 | 535 |
| SYTO 23 | 499 | 520 |
| SYTO 24 | 490 | 515 |
| SYTO 25 | 521 | 556 |
| SYTO 40 | 420 | 441 |
| SYTO 41 | 430 | 454 |
| SYTO 42 | 433 | 460 |
| SYTO 43 | 436 | 467 |
| SYTO 44 | 446 | 471 |
| SYTO 45 | 452 | 484 |
| SYTO 59 | 622 | 645 |

TABLE 2-continued

Exemplary acceptor fluorescent dyes (FDs) that
can be linked to the conjugated polymers

| Fluorophore | Absorption (nm) | Emission (nm) |
|---|---|---|
| SYTO 60 | 652 | 678 |
| SYTO 61 | 628 | 645 |
| SYTO 62 | 652 | 676 |
| SYTO 63 | 657 | 673 |
| SYTO 64 | 599 | 619 |
| SYTO 80 | 531 | 545 |
| SYTO 81 | 530 | 544 |
| SYTO 82 | 541 | 560 |
| SYTO 83 | 543 | 559 |
| SYTO 84 | 567 | 582 |
| SYTO 85 | 567 | 583 |
| SYTOX Blue | 445 | 470 |
| SYTOX Green | 504 | 523 |
| SYTOX Orange | 547 | 570 |
| Texas Red | 595 | 620 |
| Tide Fluor 2 (TF2) | 500 | 527 |
| Tide Fluor 2WS (TF2WS) | 502 | 525 |
| Tide Fluor 3 (TF3) | 555 | 584 |
| Tide Fluor 3WS(TF3WS) | 555 | 565 |
| Tide Fluor 4 (TF4) | 590 | 618 |
| Tide Fluor 5WS (TF5WS) | 649 | 664 |
| Tide Fluor 6WS (TF6WS) | 676 | 695 |
| Tide Fluor 7WS (TF7WS) | 749 | 775 |
| Tide Fluor 8WS (TF8WS) | 775 | 807 |
| TRITC | 550 | 573 |
| XTRITC | 582 | 601 |

Many embodiments of the compounds of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the polymer conjugates of the invention have been drawn in one or another particular electronic resonance structure. Every aspect of the instant invention applies equally to polymer conjugates that are formally drawn with other permitted resonance structures, as the electronic charge on the subject polymer conjugates is delocalized throughout the polymer conjugate itself.

Also provided are conjugates between the subject conjugated polymers and a biological substrate (BS). The BS can be linked to the conjugated polymer by any convenient means at a variety of sites, such as via conjugation to a terminal linker (-L-FG) or via conjugation to a sidechain group of a comonomer (-L-FG). In another preferred embodiment of the invention, the polymer conjugate contains at least one L-BS or L-FD-BS, where BS is attached to the polymer by a well-known reaction as listed in Table 3 as examples. In certain embodiments, the covalent linkage attaching the polymer to BS contains multiple intervening atoms that serve as a Linker (L). The polymers can be used to label a wide variety of biological, organic or inorganic substances that contain or are modified to contain functional groups with suitable reactivity, resulting in chemical attachment of the conjugated substances.

TABLE 3

Examples of compatible reactive functional groups (e.g., chemoselective functional groups) for preparing the biological conjugates of the subject polymers.

| Functional Group (FG) | Matching Functional Group | Resulting covalent linkages |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thioethers |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |
| azides | alkynes | 1,2,3-triazoles |
| 1,2,4,5-tetrazines | cyclooctynes | pyradazines |
| hydroxylamines | aldehydes/ketones | oxamines |
| hydrazines | aldehydes/ketones | hydrazones |
| cysteines | aldehydes/ketones | thiazolidines |
| aryl azides | methyl 2-diphenyl-phosphinobenzonate | 2-diphenylphosphonyl-benzoamides |
| Nitrile-N-oxides | cycloalkynes | isoxazoles |
| anthracenes | maleimides | succinimides |

Choice of the linkage used to attach the polymer to a biological substrate to be conjugated typically depends on the functional group on the biological substrate to be conjugated and the type or length of covalent linkage desired. The types of functional groups typically present on the organic or inorganic biological substrates include, but are not limited to, amines, amides, thiols, alcohols, phenols, aldehydes, ketones, phosphonates, imidazoles, hydrazines, hydroxylamines, disubstituted amines, halides, epoxides, carboxylate esters, sulfonate esters, purines, pyrimidines, carboxylic acids, olefinic bonds, azide, alkyne, tetrazine or a combination of these groups. A single type of reactive site may be available on the biological substrate (typical for polysaccharides), or a variety of sites may occur (e.g. amines, thiols, alcohols, phenols), as is typical for proteins. A conjugated biological substrate may be conjugated to more than one polymer conjugate, which may be the same or different, or to a biological substrate that is additionally modified by a hapten, such as biotin. Alternatively multiple substrates might be conjugated to a single polymer, Although some selectivity can be obtained by careful control of the reaction conditions, selectivity of labeling is best obtained by selection of an appropriate reactive polymer conjugate.

Typically, a conjugated polymer including a suitable reactive functional group will react with an amine, a thiol, an alcohol, an aldehyde or a ketone. Preferably, the conjugated polymer reactive functional group reacts with an amine, a thiol functional or a clickable group. In one embodiment, polymer includes, or is modified to include an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, tetrazine, azide, alkyne or a thiol group. By "reactive platinum complex" is particularly meant chemically reactive platinum complexes such as described in U.S. Pat. Nos. 5,580,990; 5,714,327 and 5,985,566.

Where the conjugated polymer includes a photoactivatable functional group, such as an azide, diazirinyl, azidoaryl, or psoralen derivative, the polymer becomes chemically reactive only after illumination with light of an appropriate wavelength. Where the conjugated polymer includes an activated ester of a carboxylic acid, the reactive polymer is particularly useful for preparing polymer conjugates of proteins, nucleotides, oligonucleotides, or haptens. Where the conjugated polymer includes a maleimide or haloacetamide the reactive polymer is particularly useful for conjugation to thiol-containing biological substrates. Where the conjugated polymer includes a hydrazide, the reactive polymer is particularly useful for conjugation to periodate-oxidized carbohydrates and glycoproteins, and in addition is an aldehyde-fixable polar tracer for cell microinjection. Where the conjugated polymer includes a clickable functional group, the reactive polymer is particularly useful for conjugation to the complimentary clickable substrate. Preferably, the conjugated polymer includes a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, polymer is a succinimidyl ester of a carboxylic acid, a maleimide, an iodoacetamide, or a reactive platinum complex.

Based on the above-mentioned attributes, the appropriate reactive polymers of the invention are selected for the preparation of the desired polymer conjugates (e.g., FD conjugate and/or BS conjugates of the subject conjugated polymers), whose advantageous properties make them useful for a wide variety of applications. Particularly useful polymer conjugates include, among others, conjugates where substrate is a peptide, a nucleotide, an antigen, a steroid, a vitamin, a drug, a hapten, a metabolite, a toxin, an environmental pollutant, an amino acid, a protein, a nucleic acid, a nucleic acid polymer, a carbohydrate, a lipid, an ion-complexing moiety, a glass or a non-biological polymer. Alternatively, substrate is a cell, a cellular system, a cellular fragment, or a subcellular particle (e.g. inter alia), a virus particle, a bacterial particle, a virus component, a biological cell (such as animal cell, plant cell, bacteria, yeast, or protist), or a cellular component. Reactive polymers typically label functional groups at the cell surface, in cell membranes, organelles, or cytoplasm.

Typically, the substrate (e.g., BS) is an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. More typically, substrate is a peptide, a protein, a nucleotide, an oligonucleotide, or a nucleic acid. When conjugating polymer conjugates of the invention to such biopolymers, it is possible to incorporate more polymers per molecule to increase the fluorescent signal. For polymer-antibody conjugates, one polymer/antibody is preferred.

In one embodiment, the substrate is an amino acid (including those that are protected or are substituted by phosphonates, carbohydrates, or $C_1$ to $C_{25}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one preferred aspect, the conjugated protein is a polymer antibody conjugate.

In one aspect of the invention, the substrate is a conjugated biological substrate that is an antibody (including intact antibodies, antibody fragments, and antibody sera, etc.), an amino acid, an angiostatin or endostatin, an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), or a tyramide.

In another preferred embodiment, substrate is a nucleic acid base, nucleoside, nucleotide or a nucleic acid polymer, including those that are modified to possess an additional linker or spacer for attachment of the polymer conjugates of the invention, such as an alkynyl linkage (U.S. Pat. No. 5,047,519), an aminoallyl linkage (U.S. Pat. No. 4,711,955), or a heteroatom-substituted linker (U.S. Pat. No. 5,684,142) or other linkage. In another preferred embodiment, the conjugated biological substrate is a nucleoside or nucleotide analog that links a purine or pyrimidine base to a phosphate or polyphosphate moiety through a noncyclic spacer. In another preferred embodiment, the polymer conjugate is conjugated to the carbohydrate portion of a nucleotide or nucleoside, typically through a hydroxyl group but additionally through a thiol or an amino group (U.S. Pat. Nos. 5,659,025; 5,668,268; 5,679,785). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510) and nucleic acids containing such bases can also be coupled to polymer conjugates of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna H, Cheung I, Ames B N. PROC. NATL. ACAD. SCI. U.S.A. 97, 686-691 (2000).

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen, et al. U.S. Pat. No. 5,539,082,) may be preferred for some applications because of their generally faster hybridization rates.

In one embodiment, the conjugated oligonucleotides of the invention are aptamers for a particular target molecule, such as a metabolite, polymer conjugate, hapten, or protein. That is, the oligonucleotides have been selected to bind preferentially to the target molecule. Methods of preparing and screening aptamers for a given target molecule have been previously described and are known in the art [for example, U.S. Pat. No. 5,567,588 to Gold (1996)].

In another preferred embodiment, substrate is a carbohydrate that is typically a polysaccharide, such as a dextran, heparin, glycogen, amylopectin, mannan, inulin, starch, agarose and cellulose. Alternatively, the carbohydrate is a polysaccharide that is a lipopolysaccharide. Preferred polysaccharide conjugates are dextran, or lipopolysaccharide conjugates.

Conjugates having an ion-complexing moiety serve as indicators for calcium, sodium, magnesium, zinc, potassium, or other biologically important metal ions. Preferred ion-complexing moieties are crown ethers (U.S. Pat. No. 5,405,975); derivatives of 1,2-bis-(2-aminophenoxyethane)-N,N,N',N'-tetraacetic acid (BAPTA chelators; U.S. Pat. Nos. 5,453,517; 5,516,911 and 5,049,673); derivatives of 2-carboxymethoxyaniline-N,N-di-acetic acid (APTRA chelators; AM. J. PHYSIOL., 256, C540 (1989)); or pyridine- and phenanthroline-based metal ion chelators (U.S. Pat. No. 5,648,270); or derivatives of nitrilotriacetic acid, see e.g. "Single-step synthesis and characterization of biotinylated nitrilotriacetic acid, a unique reagent for the detection of histidine-tagged proteins immobilized on nitrocellulose", McMahan S A and Burgess R R, ANAL. BIOCHEM., 236, 101-106 (1996). Preferably, the ion-complexing moiety is a crown ether chelator, a BAPTA chelator, an APTRA chelator or a derivative of nitrilotriacetic acid.

Other conjugates of non-biological materials include polymer conjugate-conjugates of organic or inorganic polymers, polymeric films, polymeric wafers, polymeric membranes, polymeric particles, or polymeric microparticles (magnetic and non-magnetic microspheres); iron, gold or silver particles; conducting and non-conducting metals and non-metals; and glass and plastic surfaces and particles. Conjugates are optionally prepared by copolymerization of a polymer conjugate that contains an appropriate functionality while preparing the polymer, or by chemical modification of a polymer that contains functional groups with suitable chemical reactivity. Other types of reactions that are useful for preparing polymer conjugate-conjugates of polymers include catalyzed polymerizations or copolymerizations of alkenes and reactions of dienes with dienophiles, transesterifications or transaminations. In another preferred embodiment, the conjugated biological substrate is a glass or silica, which may be formed into an optical fiber or other structure.

In one embodiment, conjugates of biological polymers such as peptides, proteins, oligonucleotides, nucleic acid polymers are also labeled with at least a second fluorescent dye conjugate, which is optionally an additional polymer conjugate of the present invention, to form an energy-transfer pair. In some aspects of the invention, the labeled conjugate functions as an enzyme substrate, and enzymatic hydrolysis disrupts the energy transfer. In another preferred embodiment of the invention, the energy-transfer pair that incorporates a polymer conjugate of the invention is conjugated to an oligonucleotide that displays efficient fluorescence quenching in its hairpin conformation [the so-called "molecular beacons" of Tyagi, et al., NATURE BIOTECHNOLOGY, 16, 49 (1998)] or fluorescence energy transfer.

The preparation of polymer conjugates using reactive polymer conjugates is well documented, e.g. e.g. U.S. Pat. Nos. 8,158,444; 8,455,613; 8,354,239; 8,362,193; and 8,575,303 to Gaylord, et al.; also WO 2013/101902 to Chiu et al. The other biological applications of polyconjugated polymers have been well documented by Thomas III et al. (Chem. Rev. 2007, 107, 1339); Zhu et al (Chem. Rev. 2012, 112, 4687) and Zhu et al. (Chem. Soc. Rev., 2011, 40, 3509). Conjugates typically result from mixing appropriate reactive polymers and biological substrate to be conjugated in a suitable solvent in which both are soluble. The polymer conjugates of the invention are readily soluble in aqueous solutions, facilitating conjugation reactions with most biological materials. For those reactive polymer conjugates that are photoactivated, conjugation requires illumination of the reaction mixture to activate the reactive polymer conjugates.

The present disclosure provides a conjugated polymer containing the structure of Formula 2:

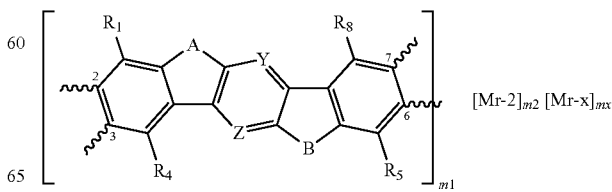

Formula 2 wherein the polymer comprises monomer units that are randomly distributed along the polymer main chain with the first monomer connected to other monomers (Mr-2 to Mr-x) through the two positions of C2, C3, C6 or C7 of the first monomer; wherein $R_1$ to $R_8$ independently represent hydrogen, a halogen, an alkyl, a WSG, an aryl, a heteroaryl group, a FD, a FG, or a L-BS; A and B are independently O, S, N—$R_{11}$, P—$R_{11}$, O=P—$R_{11}$, O=P—$OR_{11}$, $R_{11}$—C—$R_{12}$, $R_{11}$—Si—$R_{12}$, O=S—$R_{11}$, O=S(O)—$R_{11}$ wherein $R_{11}$ and $R_{12}$ independently represent hydrogen, an alkyl, a WSG, an aryl, a heteroaryl group, a FD, a FG, or a L-BS; Y and Z are independently none, C, O, S, N, N—$R_{13}$, P, P—$R_{13}$, O=P—$R_{13}$, O=P—$OR_{13}$, O=S—$R_{13}$, O=S(O)—$R_{13}$ wherein $R_{13}$ and $R_{14}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(2). at least one of Mr1 to Mr-X has a WSG;
(3). at least one of Mr1 to Mr-X has a FG or a L-BS;
(4). at least one of A, B Y or Z is a heteroatom The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

In another embodiment, the disclosure provides the conjugated polymer containing Formula 2, wherein $R_1$ to $R_8$ independently represent hydrogen or fluoro; A and B are independently N—$R_{11}$, P—$R_{11}$, O=P—$R_{11}$, O=P—$OR_{11}$, $R_{11}$—C—$R_{12}$, $R_{11}$—Si—$R_{12}$, $R_{11}$—S—$R_{12}$, O=S—$R_{11}$, O=S(O)—$R_{11}$; $R_{11}$ and $R_{12}$ independently represent hydrogen, an alkyl, a PEG, a FD, a FG, or a L-BS wherein L is an alkyl or a PEG; Y and Z are independently none or carbon; Mr-2 to Mr-x are independently a double bond, a triple bond, an aryl, a heteroaryl or, a FD that is optionally substituted by a FG, or a L-BS wherein L is an alkyl or a PEG; m1 is an integer larger than 5, m2 to mx are integers from 0 to 200, provided that m1 is ≥10, and the sum of Mr1 to Mr-X are 10-200.

In another embodiment, the disclosure provides the conjugated polymer containing Formula 2, wherein $R_1$ to $R_8$ independently represent hydrogen; A and B are independently N—$R_{11}$, $R_{11}$—C—$R_{12}$, $R_{11}$—Si—$R_{12}$, $R_{11}$—S—$R_{12}$; $R_{11}$ and $R_{12}$ are independently a hydrogen, an alkyl, a PEG, a fluorescent dye, a FG, or a L-BS wherein linker (L) is an alkyl or a PEG; Y and Z are independently none or carbon wherein m and n are independently 0 or 1; m1 to mx are integers from 1 to 200; provided that the sum of Mr1 to Mr-X are 10-200.

In another embodiment, the disclosure provides the conjugated polymer containing Formula 2, wherein $R_1$ to $R_8$ independently represent hydrogen; A and B are independently N—$R_{11}$, $R_{11}$—C—$R_{12}$, $R_{11}$—Si—$R_{12}$, $R_{11}$—S—$R_{12}$; $R_{11}$ and $R_{12}$ are a PEG; Y and Z are independently none or carbon wherein m and n are independently 0 or 1; Mr-2 is a fluorene that is optionally substituted with a FD, a FG, or a L-BS wherein L is an alkyl or a PEG; m1 and m2 are integers from 1 to 200; provided that m1 is ≥30, and the sum of Mr1 to Mr-X are 10-200.

In another embodiment, the disclosure provides the conjugated polymer containing Formula 2, wherein $R_1$ to $R_8$ independently represent hydrogen; A and B are independently N—$R_{11}$, $R_{11}$—C—$R_{12}$, $R_{11}$—Si—$R_{12}$, $R_{11}$—S—$R_{12}$; $R_{11}$ and $R_{12}$ are a PEG; Y and Z are independently none or carbon wherein m and n are independently 0 or 1; Mr-2 is a phenyl that is optionally substituted with a FD, a FG, or a L-BS wherein L is an alkyl or a PEG; m1 and m2 are integers from 1 to 200; provided that m1 is ≥30, and the sum of Mr1 to Mr-X are 10-200.

In another embodiment, the disclosure provides the conjugated polymer containing Formula 2, wherein $R_1$ to $R_8$ independently represent hydrogen; A and B are independently N—$R_{11}$, $R_{11}$—C—$R_{12}$, $R_{11}$—Si—$R_{12}$, $R_{11}$—S—$R_{12}$; $R_{11}$ and $R_{12}$ are a PEG; Y and Z are independently none or carbon wherein m and n are independently 0 or 1; Mr-2 is a FD that is optionally substituted with a FG, or a L-BS wherein L is an alkyl or a PEG; Mr-3 is a phenyl that is optionally substituted with a FG, or a L-BS wherein L is an alkyl or a PEG; m1, m2 and m3 are integers from 1 to 200; provided that m1 is ≥30, and the sum of Mr1 to Mr-X are 10-200.

In another embodiment, the disclosure provides the conjugated polymer containing Formula 2, wherein $R_1$ to $R_8$ independently represent hydrogen; A and B are independently N—$R_{11}$, $R_{11}$—C—$R_{12}$, $R_{11}$—Si—$R_{12}$, $R_{11}$—S—$R_{12}$; $R_{11}$ and $R_{12}$ are a PEG; Y and Z are independently none or carbon wherein m and n are independently 0 or 1; Mr-2 is a FD that is optionally substituted with a FG, or a L-BS wherein L is an alkyl or a PEG; m1 and m3 are integers from 1 to 200; provided that m1 is ≥30, and the sum of Mr1 to Mr-X are 10-200.

In another embodiment, the disclosure provides the conjugated polymers containing Formula 2, wherein PEGs are PEG6 to PEG18.

In another embodiment, the disclosure provides the conjugated polymers containing Formula 2, wherein VSGs are a PEG, a carboxyalkyl, a sulfonylalkyl, a phosphonylalkyl, a hydroxyalkyl, an aminoalkyl or an ammoniumylalkyl.

In another embodiment, the disclosure provides the conjugated polymers containing Formula 2, wherein FG is an activated ester, an aldehyde, an maleimide, a 1,2,4,5-tetrazine, a hydroxylamine, a hydrazine, an azide, an alkyne, a cyclooctyne, or a DBCO.

In another embodiment, the disclosure provides the conjugated polymers containing Formula 2, wherein end group is a hydrogen, bromo, iodo, boronyl or a FG.

In another embodiment, the disclosure provides the conjugated polymers containing Formula 2, wherein BS is an antibody, an antigen, a protein, a peptide, an oligonucleotide, a DNA, an RNA, a PNA, an aptamer or a cell.

In another embodiment, the disclosure provides the conjugated polymers containing Formula 2, wherein FD is a bodipy, a polythiophene, a polypyrrole, a porphyrin, a phthalocyanine, or a carbocyanine.

The present disclosure provides a conjugated polymer containing the structure of Formula 4:

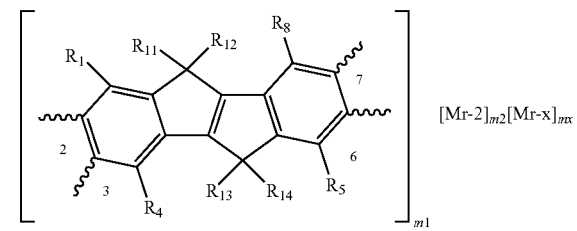

Formula 4 wherein the polymer comprises monomer units that are randomly distributed along the polymer main chain with the first monomer connected to other monomers (Mr-2 to Mr-x) through C2/C3 and C6/C7 of the first monomer; wherein $R_1$ to $R_8$ independently represent hydrogen, a halogen, an alkyl, a WSG, an aryl, a heteroaryl group, a FD, a FG, or a L-BS; $R_{11}$ to $R_{14}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(2). at least one of $R_{11}$ to $R_{14}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

In another embodiment, the disclosure provides the conjugated polymer containing Formula 4, wherein $R_1$ to $R_8$ are hydrogen; $R_{11}$ to $R_{14}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that m1 is ≥10, the sum of Mr1 to Mr-X is 50 to 200, and at least one of $R_{11}$ to $R_{14}$ is a WSG.

In another embodiment, the disclosure provides the conjugated polymer containing Formula 4, wherein $R_1$ to $R_8$ are hydrogen; $R_{11}$ to $R_{14}$ independently represent hydrogen, an alkyl, a PEG, a FD, a FG, or a L-BS; Mr-2 is a fluorene that is optionally substituted with a FD, a FG, or a L-BS wherein L is an alkyl or a PEG; m1 and m2 are integers from 1 to 200; provided that m1 is ≥30, the sum of Mr1 to Mr-X are 10-200 and at least one of $R_{11}$ to $R_{14}$ is a PEG.

In another embodiment, the disclosure provides the conjugated polymer containing Formula 4, wherein $R_1$ to $R_8$ are hydrogen; $R_{11}$ to $R_{14}$ are a PEG that is optionally substituted with a FD, a FG, or a L-BS; Mr-2 is a phenyl that is optionally substituted with a FD, a FG, or a L-BS; m1 and m2 are integers from 1 to 200; provided that m1 is ≥30, the sum of Mr1 to Mr-X are 10-200.

In another embodiment, the disclosure provides the conjugated polymer containing Formula 4, wherein $R_1$ to $R_8$ are hydrogen; $R_{11}$ to $R_{14}$ are a PEG that is optionally substituted with a FD, a FG, or a L-BS; Mr-2 is a FD that is optionally substituted with a FG, or a L-BS wherein L is an alkyl or a PEG; Mr-3 is a phenyl that is optionally substituted with a FG, or a L-BS; m1, m2 and m3 are integers from 1 to 200; provided that m1 is ≥30, and the sum of Mr1 to Mr-X are 10-200.

The present disclosure provides a conjugated polymer containing the structure of Formula 5:

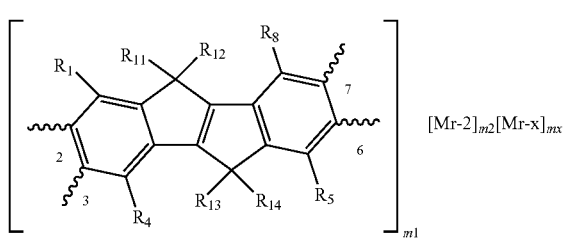

Formula 5

$[Mr-2]_{m2}[Mr-x]_{mx}$ wherein the polymer comprises monomer units that are randomly distributed along the polymer main chain with the first monomer connected to other monomers (Mr-2 to Mr-x) through C2 and C7 of the first monomer; wherein $R_1$ to $R_8$ independently represent hydrogen, a halogen, an alkyl, a WSG, an aryl, a heteroaryl group, a FD, a FG, or a L-BS; $R_{11}$ to $R_{14}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(2). at least one of $R_{11}$ to $R_{14}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

In another embodiment, the disclosure provides the conjugated polymer containing Formula 5, wherein $R_1$ to $R_8$ are hydrogen; $R_{11}$ to $R_{14}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that m1 is ≥10, the sum of Mr1 to Mr-X is 50 to 200, and at least one of $R_{11}$ to $R_{14}$ is a WSG.

In another embodiment, the disclosure provides the conjugated polymer containing Formula 5, wherein $R_1$ to $R_8$ are hydrogen; $R_{11}$ to $R_{14}$ independently represent hydrogen, an alkyl, a PEG, a FD, a FG, or a L-BS; Mr-2 is a fluorene that is optionally substituted with a FD, a FG, or a L-BS wherein L is an alkyl or a PEG; m1 and m2 are integers from 1 to 200; provided that m1 is ≥30, the sum of Mr1 to Mr-X are 10-200 and at least one of $R_{11}$ to $R_{14}$ is a PEG.

In another embodiment, the disclosure provides the conjugated polymer containing Formula 5, wherein $R_1$ to $R_8$ are hydrogen; $R_{11}$ to $R_{14}$ are a PEG that is optionally substituted with a FD, a FG, or a L-BS; Mr-2 is a phenyl that is optionally substituted with a FD, a FG, or a L-BS; m1 and m2 are integers from 1 to 200; provided that m1 is ≥30, the sum of Mr1 to Mr-X are 10-200.

In another embodiment, the disclosure provides the conjugated polymer containing Formula 5, wherein $R_1$ to $R_8$ are hydrogen; $R_{11}$ to $R_{14}$ are a PEG that is optionally substituted with a FD, a FG, or a L-BS; Mr-2 is a FD that is optionally substituted by a FG, or a L-BS wherein L is an alkyl or a PEG; Mr-S is a phenyl that is optionally substituted with a FG, or a L-BS; m1, m2 and m3 are integers from 1 to 200; provided that m1 is ≥30, and the sum of Mr1 to Mr-X are 10-200.

The present disclosure provides a conjugated polymer containing the structure of Formula 6:

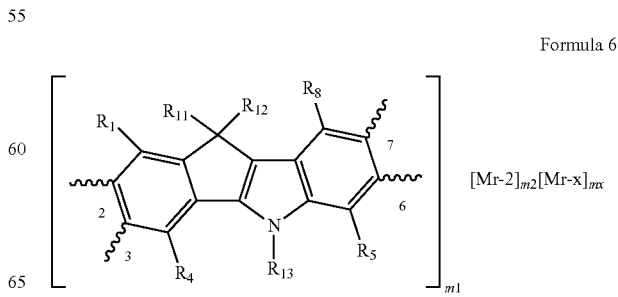

Formula 6

$[Mr-2]_{m2}[Mr-x]_{mx}$ wherein the polymer comprises monomer units that are randomly distributed along the polymer main chain with the first monomer connected to other monomers (Mr-2 to Mr-x) through C2/C3 and C6/C7 of the first monomer; wherein $R_1$ to $R_8$ independently represent hydrogen, a halogen, an alkyl, a WSG, an aryl, a heteroaryl group, a FD, a FG, or a L-BS; $R_{11}$ to $R_{13}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that
(1). the sum of Mr1 to Mr-X is ≥10; and
(2). at least one of $R_{11}$ to $R_{13}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

In another embodiment, the disclosure provides the conjugated polymer containing Formula 6, wherein $R_1$ to $R_8$ are hydrogen; $R_{11}$ to $R_{13}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that m1 is ≥10, the sum of Mr1 to Mr-X is 50 to 200, and at least one of $R_{11}$ to $R_{13}$ is a WSG.

In another embodiment, the disclosure provides the conjugated polymer containing Formula 6, wherein $R_1$ to $R_8$ are hydrogen; $R_{11}$ to $R_{13}$ independently represent hydrogen, an alkyl, a PEG, a FD, a FG, or a L-BS; Mr-2 is a fluorene that is optionally substituted with a FD, a FG, or a L-BS wherein L is an alkyl or a PEG; m1 and m2 are integers from 1 to 200; provided that m1 is ≥30, the sum of Mr1 to Mr-X are 10-200 and at least one of $R_{11}$ to $R_{13}$ is a PEG.

In another embodiment, the disclosure provides the conjugated polymer containing Formula 6, wherein $R_1$ to $R_8$ are hydrogen; $R_{11}$ to $R_{13}$ are a PEG that is optionally substituted with a FD, a FG, or a L-BS; Mr-2 is a phenyl that is optionally substituted with a FD, a FG, or a L-BS; m1 and m2 are integers from 1 to 200; provided that m1 is ≥30, the sum of Mr1 to Mr-X are 10-200.

In another embodiment, the disclosure provides the conjugated polymer containing Formula 6, wherein $R_1$ to $R_8$ are hydrogen; $R_{11}$ to $R_{13}$ are a PEG that is optionally substituted with a FD, a FG, or a L-BS; Mr-2 is a FD that is optionally substituted by a FG, or a L-BS wherein L is an alkyl or a PEG; Mr-3 is a phenyl that is optionally substituted with a FG, or a L-BS; m1, m2 and m3 are integers from 1 to 200; provided that m1 is ≥30, and the sum of Mr1 to Mr-X are 10-200.

The present disclosure provides a conjugated polymer containing the structure of Formula 7:

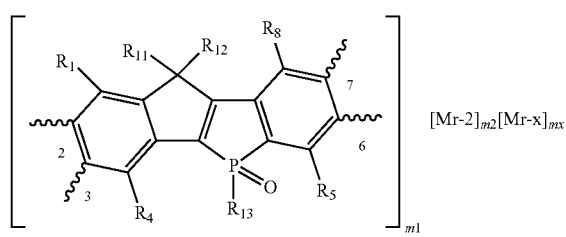

Formula 7 wherein the polymer comprises monomer units that are randomly distributed along the polymer main chain with the first monomer connected to other monomers (Mr-2 to Mr-x) through C2/C3 and C6/C7 of the first monomer; wherein $R_1$ to $R_8$ independently represent hydrogen, a halogen, an alkyl, a WSG, an aryl, a heteroaryl group, a FD, a FG, or a L-BS; $R_{11}$ to $R_{13}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that
(1). the sum of Mr1 to Mr-X is ≥10; and
(2). at least one of $R_{11}$ to $R_{13}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

In another embodiment, the disclosure provides the conjugated polymer containing Formula 7, wherein $R_1$ to $R_8$ are hydrogen; $R_{11}$ to $R_{13}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that m1 is ≥10, the sum of Mr1 to Mr-X is 50 to 200, and at least one of $R_{11}$ to $R_{13}$ is a WSG.

In another embodiment, the disclosure provides the conjugated polymer containing Formula 7, wherein $R_1$ to $R_8$ are hydrogen; $R_{11}$ to $R_{13}$ independently represent hydrogen, an alkyl, a PEG, a FD, a FG, or a L-BS; Mr-2 is a fluorene that is optionally substituted with a FD, a FG, or a L-BS wherein L is an alkyl or a PEG; m1 and m2 are integers from 1 to 200; provided that m1 is ≥30, the sum of Mr1 to Mr-X are 10-200 and at least one of $R_{11}$ to $R_{13}$ is a PEG.

In another embodiment, the disclosure provides the conjugated polymer containing Formula 7, wherein $R_1$ to $R_8$ are hydrogen; $R_{11}$ to $R_{13}$ are a PEG that is optionally substituted with a FD, a FG, or a L-BS; Mr-2 is a phenyl that is optionally substituted with a FD, a FG, or a L-BS; m1 and m2 are integers from 1 to 200; provided that m1 is ≥30, the sum of Mr1 to Mr-X are 10-200.

In another embodiment, the disclosure provides the conjugated polymer containing Formula 7, wherein $R_1$ to $R_8$ are hydrogen; $R_{11}$ to $R_{13}$ are a PEG that is optionally substituted with a FD, a FG, or a L-BS; Mr-2 is a FD that is optionally substituted by a FG, or a L-BS wherein L is an alkyl or a PEG; Mr-3 is a phenyl that is optionally substituted with a FG, or a L-BS; m1, m2 and m3 are integers from 1 to 200; provided that m1 is ≥30, and the sum of Mr1 to Mr-X are 10-200.

The present disclosure provides a conjugated polymer containing the structure of Formula 8:

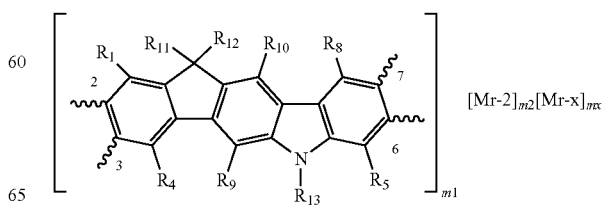

Formula 8 wherein the polymer comprises monomer units that are randomly distributed along the polymer main chain with the first monomer connected to other monomers (Mr-2 to Mr-x) through C2/C3 and C6/C7 of the first monomer; wherein $R_1$ to $R_{10}$ independently represent hydrogen, a halogen, an alkyl, a WSG, an aryl, a heteroaryl group, a FD, a FG, or a L-BS; $R_{11}$ to $R_{13}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(2). at least one of $R_{11}$ to $R_{13}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

The present disclosure provides a conjugated polymer containing the structure of Formula 9:

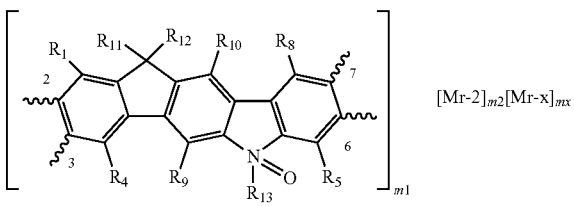

Formula 9 wherein the polymer comprises monomer units that are randomly distributed along the polymer main chain with the first monomer connected to other monomers (Mr-2 to Mr-x) through C2/C3 and C6/C7 of the first monomer; wherein $R_1$ to $R_{10}$ independently represent hydrogen, a halogen, an alkyl, a WSG, an aryl, a heteroaryl group, a FD, a FG, or a L-BS; $R_{11}$ to $R_{13}$ independently represent hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(2). at least one of $R_{11}$ to $R_{13}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

The present disclosure provides a conjugated polymer containing the structure of Formula 10:

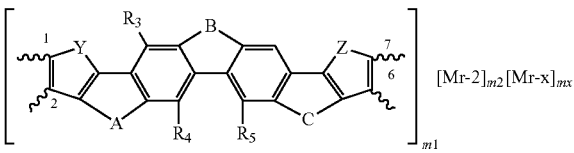

Formula 10 wherein the polymer comprises monomer units that are randomly distributed along the polymer main chain with the first monomer connected to other monomers (Mr-2 to Mr-x) through the two positions of C1/C2 and C6/C7 of the first monomer; wherein $R_2$ to $R_6$ independently represent hydrogen, a halogen, an alkyl, a WSG, an aryl, a heteroaryl group, a FD, a FG, or a L-BS; A, B and C are independently O, S, N—$R_{11}$, P—$R_{11}$, O=P—$R_{11}$, O=P—$OR_{11}$, $R_{11}$—O—$R_{12}$, $R_{11}$—Si—$R_{12}$, O=S—$R_{11}$, O=S(O)—$R_{11}$ wherein $R_{11}$ and $R_{12}$ independently represent hydrogen, an alkyl, a WSG, an aryl, a heteroaryl group, a FD, a FG, or a L-BS; Y and Z are independently O, S, N—$R_{13}$, P—$R_{13}$, O=P—$R_{13}$, O=P—$OR_{13}$, O=S—$R_{13}$, O=S(O)—$R_{13}$ wherein $R_{13}$ represents hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(2). at least one of A, B and C has a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

The present disclosure provides a conjugated polymer containing the structure of Formula 11:

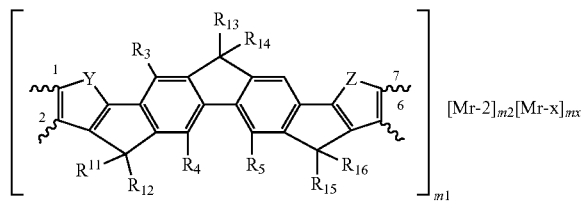

Formula 11 wherein the polymer comprises monomer units that are randomly distributed along the polymer main chain with the first monomer connected to other monomers (Mr-2 to Mr-x) through the two positions of C1 and C7 of the first monomer; wherein $R_3$ to $R_5$ independently represent hydrogen, a halogen, an alkyl, a WSG, an aryl, a heteroaryl group, a FD, a FG, or a L-BS; $R_{11}$ to $R_{16}$ independently represent hydrogen, an alkyl, a WSG, an aryl, a heteroaryl group, a FD, a FG, or a L-BS; Y and Z are independently O, S, N—$R_{17}$, P—$R_{17}$, O=P—$R_{17}$, O=P—$OR_{17}$, O=S—$R_{17}$, O=S(O)—$R_{17}$ wherein $R_{17}$ represents hydrogen, an alkyl, a WSG, an aryl, a heteroaryl group, a FD, a FG, or a L-BS; Mr-2 to Mr-x are independently a double bond, a triple bond, an aryl, a heteroaryl, or a FD that is optionally substituted by a FG, or a L-BS; m1 is an integer larger than 5, m2 to mx are integers from 0 to 200, provided that (1). the sum of Mr1 to Mr-X is ≥10; and
(3). at least two of $R_{11}$ to $R_{16}$ is a WSG; and
(3). at least one of Mr1 to Mr-X has a FG or a L-BS.

The polymers of this invention may be capped on the two terminals by a phenyl, an aryl, or a heteroaryl that is optimally substituted by bromo, iodo, boronyl, a FG or a L-BS. They are preferably capped with a phenyl, or a fluorene or their substituted analogs.

The present disclosure further provides a method of detecting an analyte in a sample, comprising
  a) combining said sample with a detection reagent comprising a polymer conjugate containing the structure of Formula 1, 2, 3, 4, 5, 6, 7, 8, 9, 10 or 11 under conditions under which said detection reagent will bind said analyte; and
  b) detecting the detection reagent bound analyte by fluorescence, In one embodiment, the disclosure provides the polymer conjugate of Formula 1, 2, 3, 4, 5, 6, 7, 8, 9, 10 or 11 wherein BS is an antibody.

In another embodiment, the disclosure provides the polymer conjugate of Formula 1, 2, 3, 4, 5, 6, 7, 8, 9, 10 or 11 wherein BS is an anti-digoxigenin antibody.

In another embodiment, the disclosure provides the polymer conjugate of Formula 1, 2, 3, 4, 5, 6, 7, 8, 9, 10 or 11 wherein BS is a goat anti-mouse IgG antibody, goat anti-rabbit IgG antibody, goat anti-human IgG antibody, donkey anti-mouse IgG antibody, donkey anti-rabbit IgG antibody, donkey anti-human IgG antibody, chicken anti-mouse IgG antibody, chicken anti-rabbit IgG antibody, or chicken anti-human IgG antibody.

In one embodiment, the disclosure provides the polymer conjugate of Formula 1, 2, 3, 4, 5, 6, 7, 8, 9, 10 or 11 wherein BS is an avidin, streptavidin, neutravidin, avidin, or avidin.

In another embodiment, the disclosure provides the polymer conjugate of Formula 1, 2, 3, 4, 5, 6, 7, 8, 9, 10 or 11 wherein the analyte is a target protein expressed on a cell surface.

In another embodiment, the sample is present on or in solid or semi-solid matrix. In one aspect of the invention, the matrix is a membrane.

In another aspect, the matrix is an electrophoretic gel, such as is used for separating and characterizing nucleic acids or proteins, or is a blot prepared by transfer from an electrophoretic gel to a membrane.

In another aspect, the matrix is a silicon chip or glass slide, and the analyte of interest has been immobilized on the chip or slide in an array (e.g. the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The polymer conjugates of the invention are generally utilized by combining a polymer conjugate of the invention as described above with the sample of interest under conditions selected to yield a detectable optical response. The term "polymer conjugate" is used herein to refer to all aspects of the claimed polymer conjugates. The polymer conjugate typically forms a covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

For biological applications, the polymer conjugates of the invention are typically used in an aqueous, mostly aqueous or aqueous-miscible solution prepared according to methods generally known in the art. The exact concentration of polymer conjugate is dependent upon the experimental conditions and the desired results. The optimal concentration is determined by systematic variation until satisfactory results with minimal background fluorescence are accomplished.

The polymer conjugates are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acids, nucleic acids or carbohydrate polymers, or lipid membrane complexes). These polymer conjugates are generally non-toxic to living cells and other biological components, within the concentrations of use.

The polymer conjugate is combined with the sample in any way that facilitates contact between the polymer conjugate and the sample components of interest. Typically, the polymer conjugate or a solution containing the polymer conjugate is simply added to the sample. Certain polymer conjugates of the invention tend to be impermeant to membranes of biological cells, and once inside viable cells are typically well retained. Treatments that permeabilize the plasma membrane, such as electroporation, shock treatments or high extracellular ATP can be used to introduce selected polymer conjugates into cells. Alternatively, selected polymer conjugates can be physically inserted into cells, e.g. by pressure microinjection, scrape loading, patch clamp methods, or phagocytosis.

Polymer conjugates that incorporate an aliphatic amine or a hydrazine residue can be microinjected into cells, where they can be fixed in place by aldehyde fixatives such as formaldehyde or glutaraldehyde. This fixability makes such polymer conjugates useful for intracellular applications such as neuronal tracing.

Polymer conjugates that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic polymer conjugates are useful as fluorescent probes of membrane structure.

Using polymer conjugates to label active sites on the surface of cells, in cell membranes or in intracellular compartments such as organelles, or in the cell's cytoplasm, permits the determination of their presence or quantity, accessibility, or their spatial and temporal distribution in the sample. Photoreactive polymer conjugates can be used similarly to photolabel components of the outer membrane of biological cells or as photo-fixable polar tracers for cells.

Optionally, the sample is washed after staining to remove residual, excess or unbound polymer conjugate. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular biological substrate, or cellular condition, according to methods generally known in the art. Where the additional detection reagent has, or yields a product with, spectral properties that differ from those of the subject polymer conjugates, multicolor applications are possible. This is particularly useful where the additional detection reagent is a polymer conjugate or polymer conjugate-conjugate of the present invention having spectral properties that are detectably distinct from those of the staining polymer conjugate.

The polymer conjugates of the invention are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and WO Appl. 94/05688 to Menchen, et al.). Polymer conjugate-conjugates of multiple independent polymer conjugates of the invention possess utility for multi-color applications.

At any time after or during staining, the sample is illuminated with a wavelength of light selected to give a detectable optical response, and observed with a means for detecting the optical response. Equipment that is useful for illuminating the polymer conjugates of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors, Preferred embodiments of the invention are polymer conjugates that are be excitable at or near the wavelengths 405 nm.

The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

One aspect of the instant invention is the formulation of kits that facilitate the practice of various assays using any of the polymer conjugates of the invention, as described above. The kits of the invention typically comprise a fluorescent polymer conjugate of the invention where the conjugated biological substrate is a specific binding pair member, or a nucleoside, a nucleotide, an oligonucleotide, a nucleic acid polymer, a peptide, or a protein. The kit optionally further comprises one or more buffering agents, typically present as an aqueous solution. The kits of the invention optionally further comprise additional detection reagents, a purification medium for purifying the resulting labeled biological substrate, luminescence standards, enzymes, enzyme inhibitors, organic solvent, or instructions for carrying out an assay of the invention.

EXAMPLES

Examples of some synthetic strategies for selected polymer conjugates of the invention, as well as their characterization, synthetic precursors, conjugates and methods of use are provided in the examples below. Further modifications and permutations will be obvious to one skilled in the art. The examples below are given so as to illustrate the practice of this invention. They are not intended to limit or define the entire scope of this invention. It is to be understood that this invention is not limited to particular aspects described, as such may vary. It is also to be understood that the terminology used herein is for the purpose of describing particular aspects only, and is not intended to be limiting since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Figure 3:
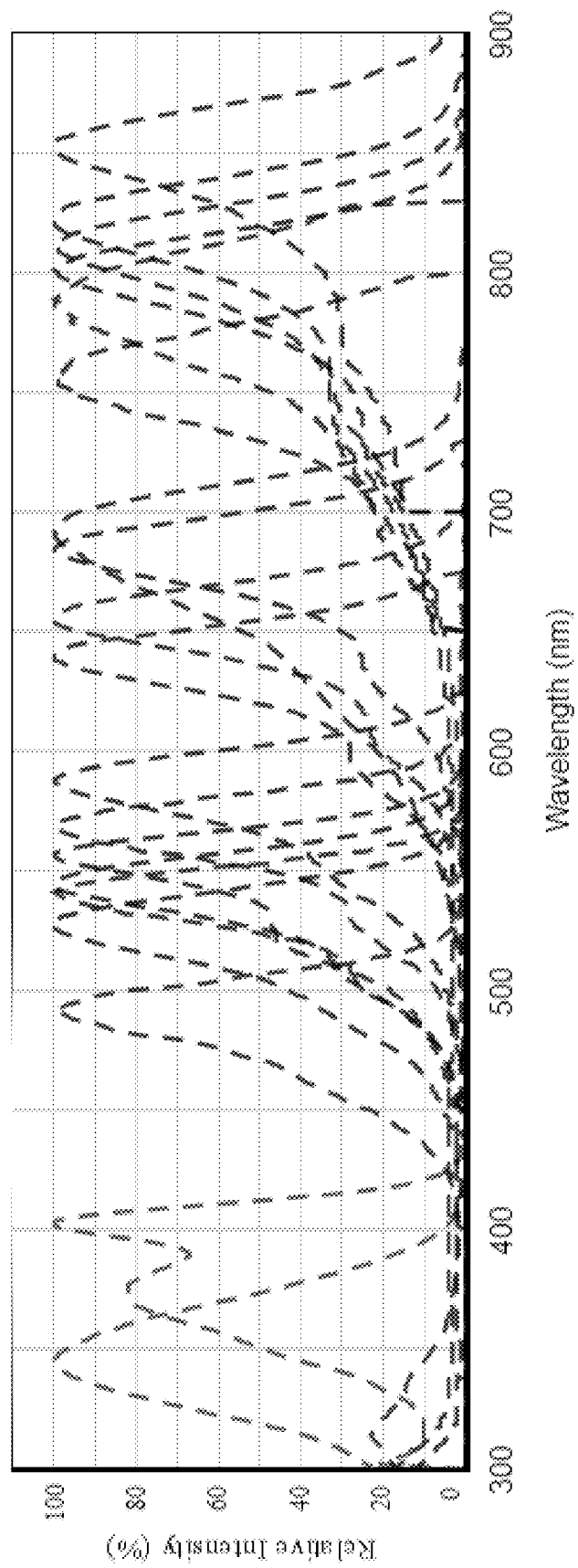
FIG. 3. The normalized absorption spectra of iFluor acceptor dyes (FD) linked to the conjugated polymers in PBS buffer (pH=7.4). The spectra displayed from left to right are iFluor 350, iFluor 405, iFluor 488, iFluor 514, iFluor 532, iFluor 546, iFluor 568, iFluor 594, iFluor 633, iFluor 647, iFluor 680, iFluor 700, iFluor 750, iFluor 790, iFluor 800, iFluor 810, iFluor 820 and iFluor 860.
Figure 4:
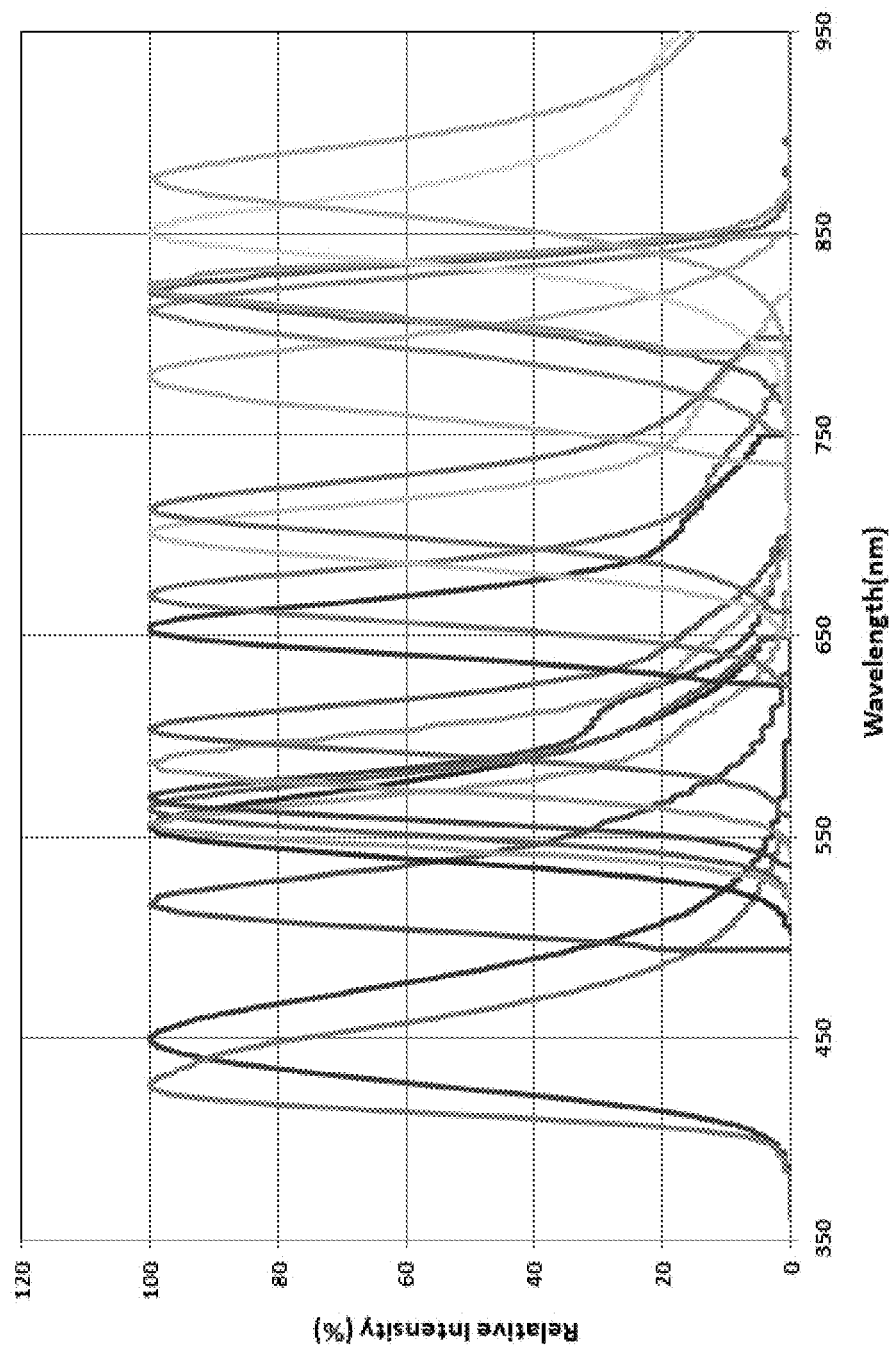
FIG. 4. The normalized fluorescence spectra of iFluor acceptor dyes (FD) linked to the conjugated polymers in PBS buffer (pH=7.4). The spectra displayed from left to right are iFluor 350, iFluor 405, iFluor 488, iFluor 514, iFluor 532, iFluor 546, iFluor 568, iFluor 594, iFluor 633, iFluor 647, iFluor 680, iFluor 700, iFluor 750, iFluor 790, iFluor 800, iFluor 810, iFluor 820 and iFluor 860.
Figure 5:
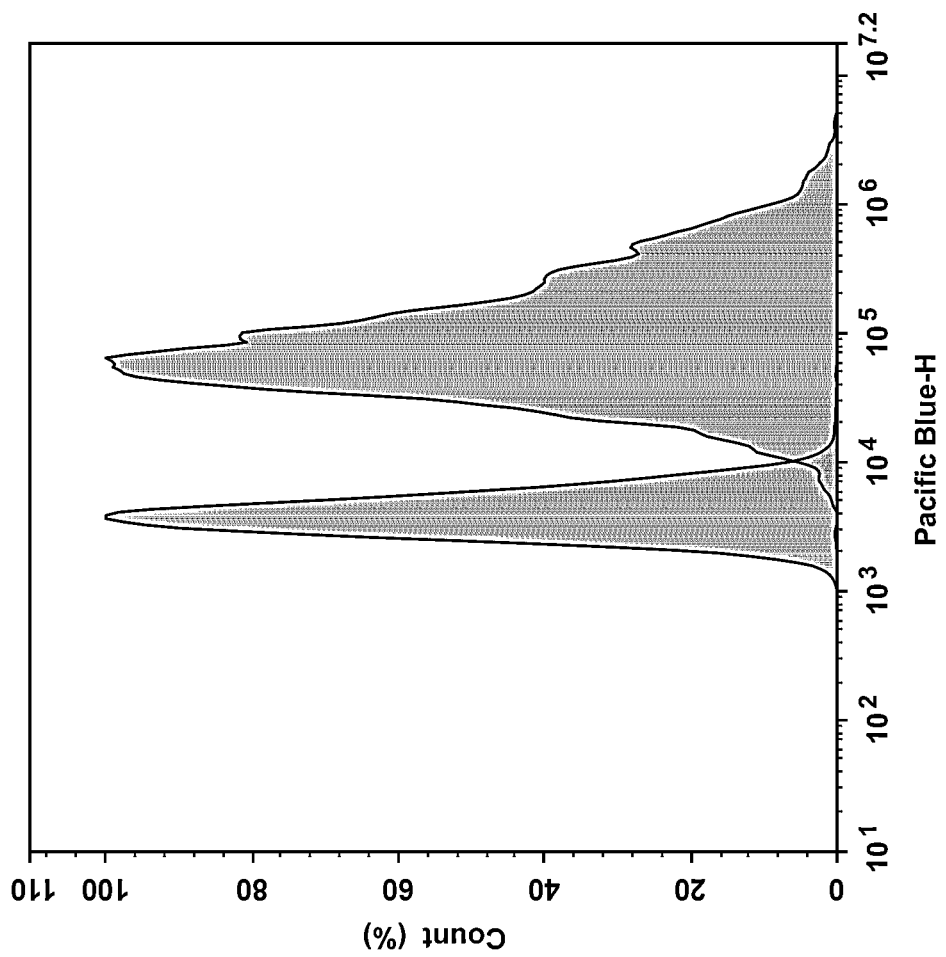
FIG. 5. Jurkat cells are centrifuged to remove medium, and blocked with the solution of HH buffer containing 1% BSA, 100 ug/ml Goat IgG for 30 min. The cells are stained with 0.4 ug/ml mouse IgG (A, control) or CPCP55 (B) for 30-60 min. The cells are washed once to remove staining solution, and analyzed with flow cytometer (Pacific Blue channel). (A). Control: mouse IgG (0.4 ug/ml); B. CPCP55 (0.4 ug/ml).
Figure 6:
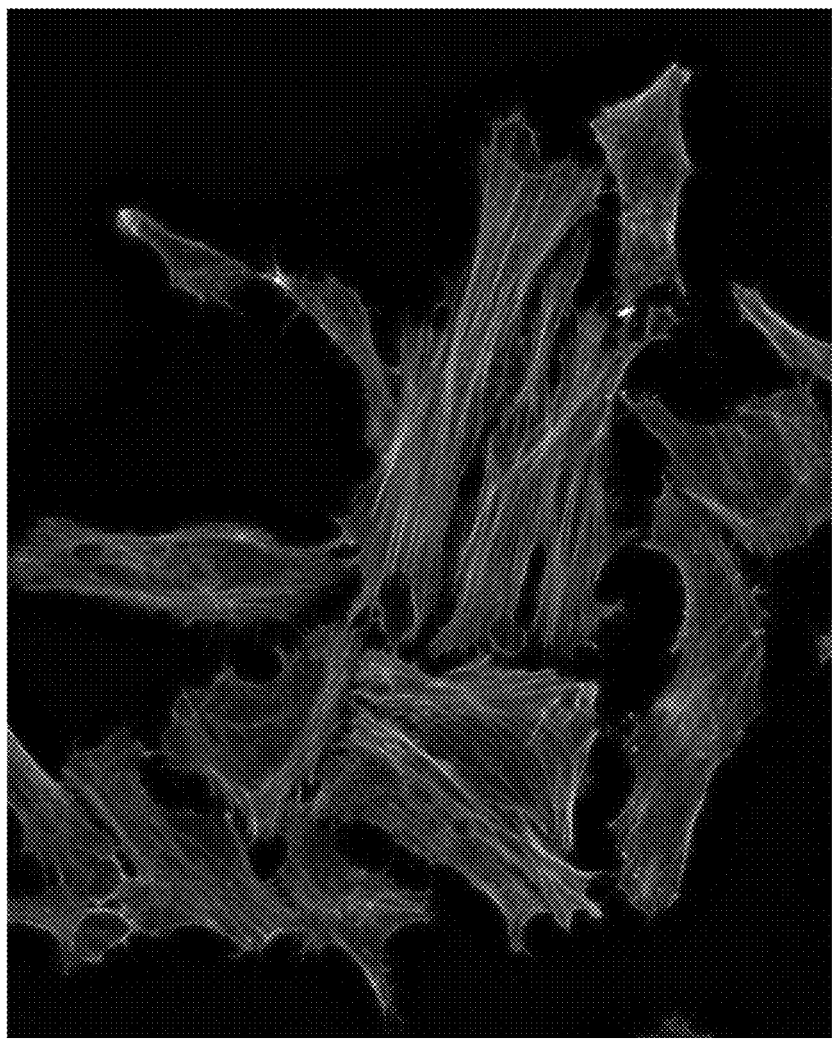
FIG. 6. The cellular F-actin staining with CPCP 60. Hela cells are fixed with 3-4% formaldehyde in PBS at room temperature for 10-30 minutes. The fixed cells are washed with PBS buffer for 3 times. 0.1% Triton is added to the fixed cells to increase conjugate permeability for 10 minutes. The cells are rinsed for 3 times with PBS. 5 μl of CPCP 60 solution (1-100 μg/ml) is added into the fixed cells (100 μL/well, 96-well plate). The cells are incubated at room temperature for 20 to 90 minutes, and rinsed gently with PBS for 3 times to remove excess phalloidin conjugate before imaging Linder a fluorescence microscope.
Figure 7A:
FIG. 7A-7B. The fluorescence imaging of tubulin in Hela cells with CPCP 51. The Hela cells are fixed with 4% formaldehyde. Mouse anti-tubulin is incubated with the fixed cells. Following the primary incubation, cells are rinsed with 5 volumes of staining buffer and spun down for 3-5 minutes. The cells are then incubated with CPCP 51 at concentrations within the range 10 ng/mL-100 ug/mL for 30-60 minutes. Following the secondary incubation, cells are rinsed with 3-5 volumes of staining buffer. The cells are imaged with an Keyence fluorescence microscope.
Figure 7B:
Figure 8:
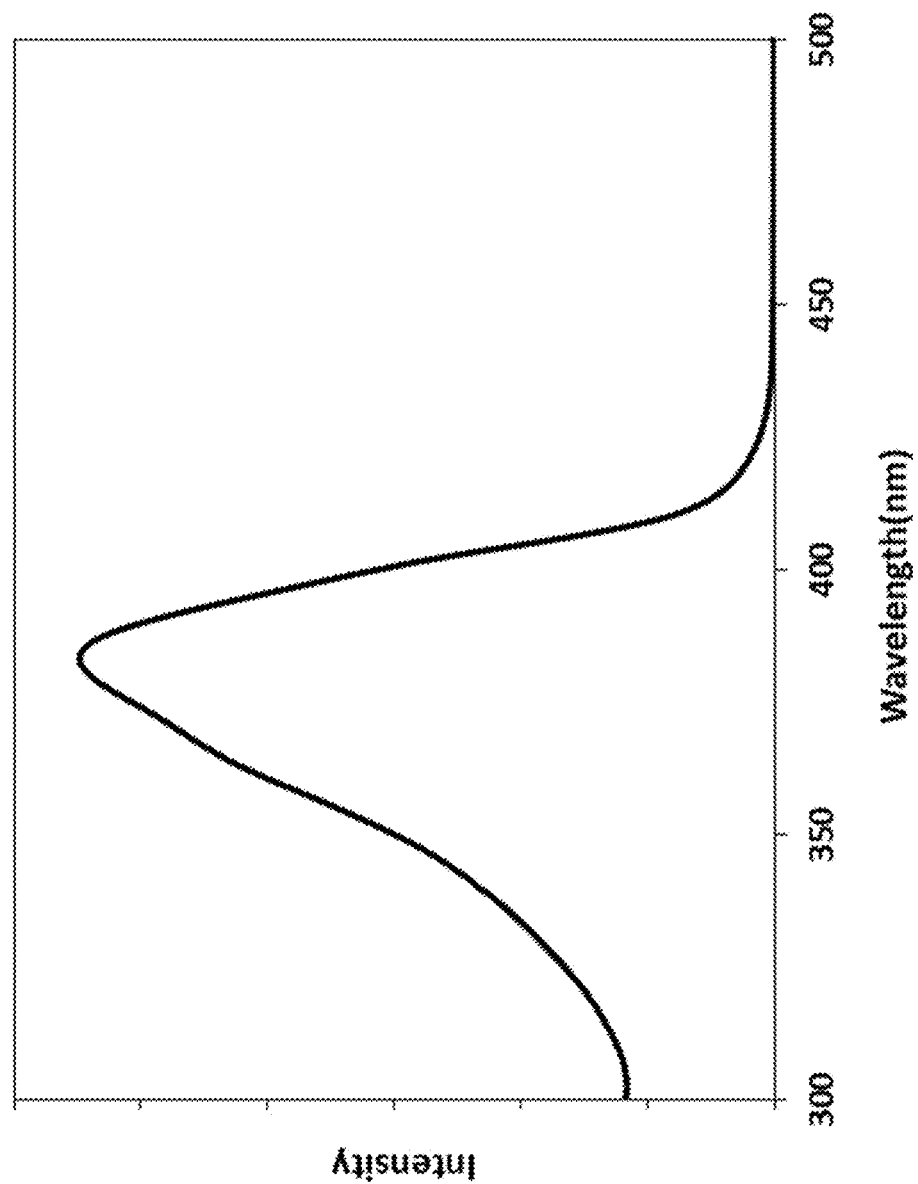
FIG. 8. The normalized absorption spectra of CPCP 140 in PBS buffer (pH=7.4).
Figure 9:
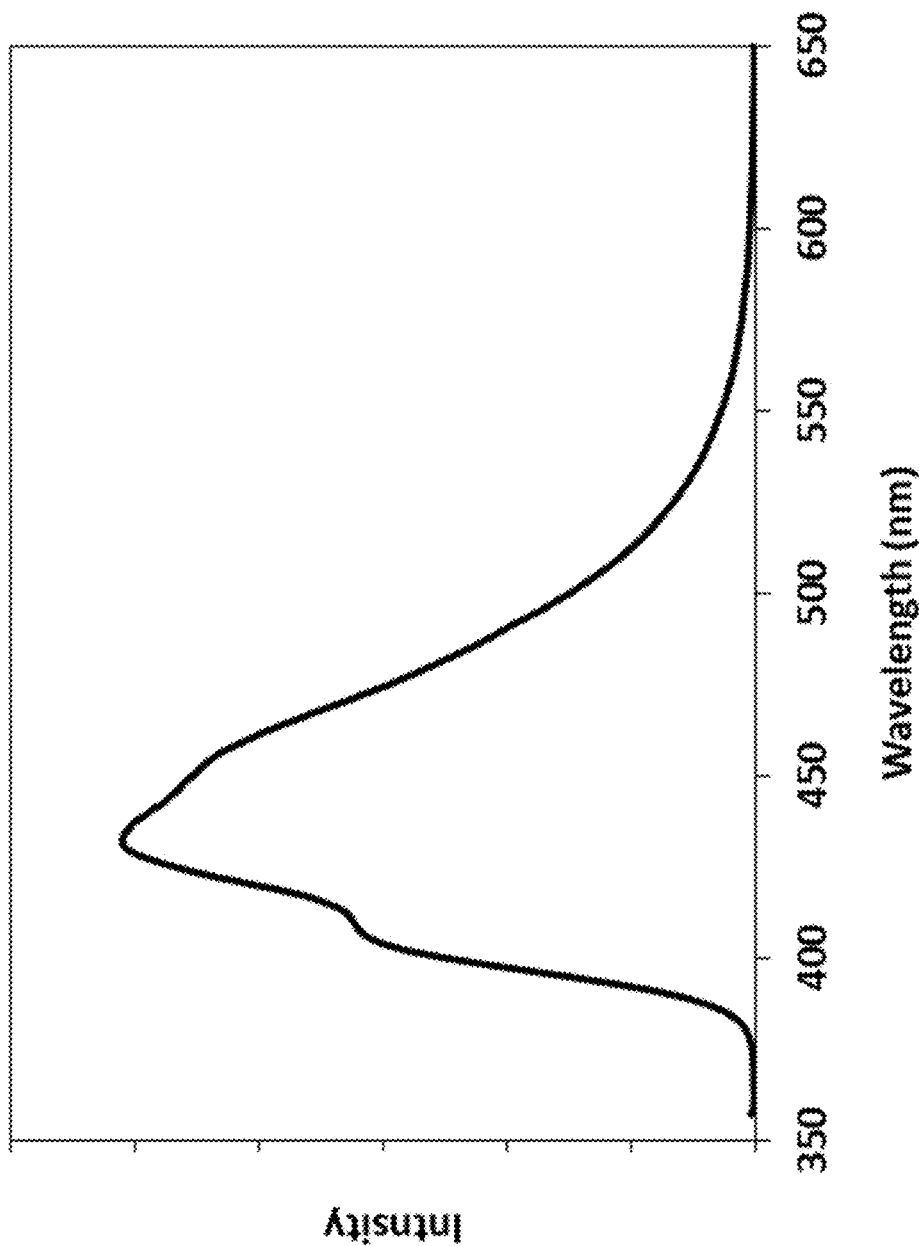
FIG. 9. The normalized fluorescence spectra of CPCP 140 in PBS buffer (pH=7.4).
Figure 10:
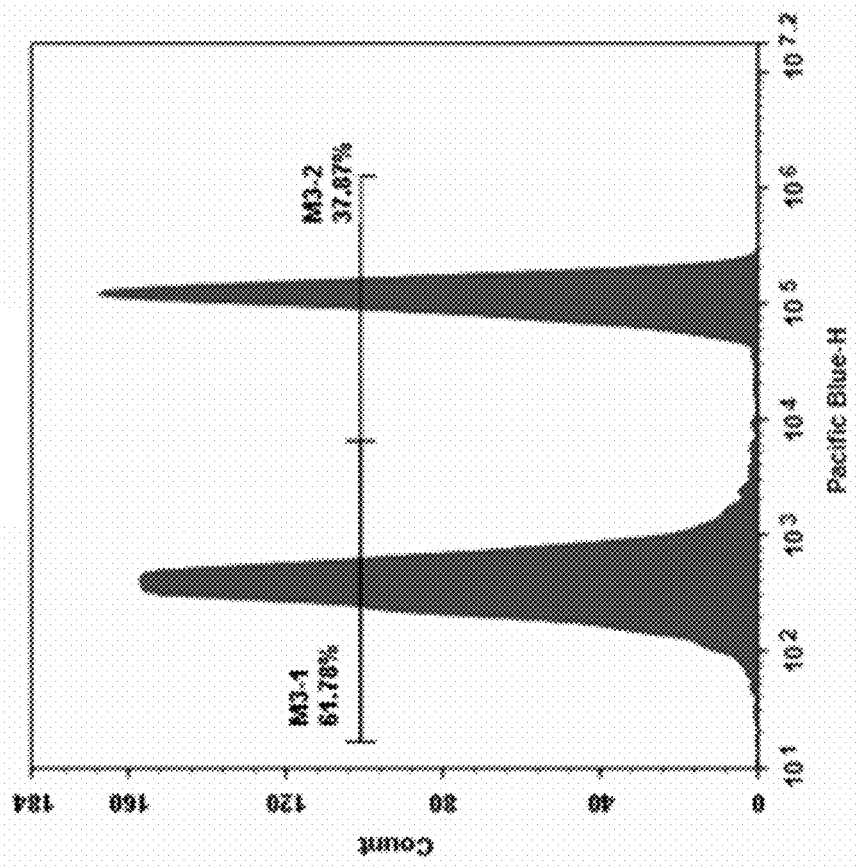
FIG. 10. The Human peripheral blood lymphocytes were stained with CPCP 140-labeled anti-Human CD4 (clone SK3, mouse IgG1, κ). The fluorescence signal is monitored using NovoCyte flow cytometer using Pacific Blue Channel. The CPCP 140-labeled anti-Human CD4 conjugate (CPCP 165) is prepared from CPCP 140 succinimidyl ester (CPCP 150) as described in Example 43.
Figure 10:
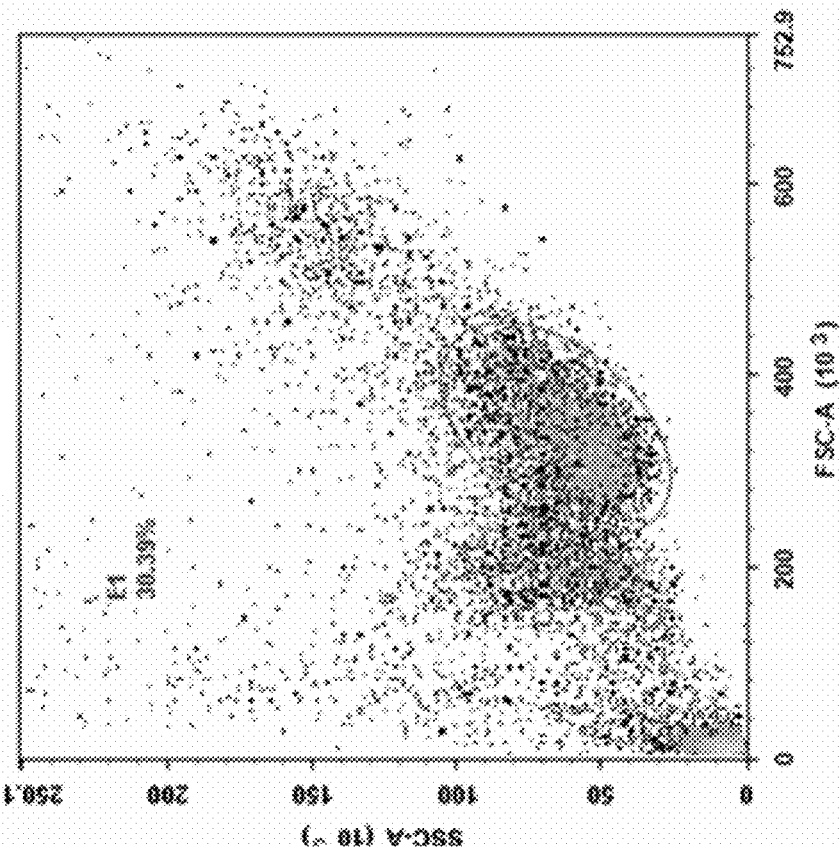

Synthesis of the reactive polymers of the invention depends on initial preparation of certain key intermediates as illustrated in FIG. 3. For simplicity, all but a few of the possible substituents are shown as hydrogen. These basic structures are optionally further substituted, during or after synthesis, to give the corresponding polymer conjugate substituents as defined above. It is recognized that there are many possible variations that may yield equivalent results.

The methods for the synthesis of polymers that contain a variety of reactive functional groups such as those described in Table 3 are well documented in the art. Particularly useful are amine-reactive polymer conjugates such as "activated esters" of carboxylic acids, which are typically synthesized by coupling a carboxylic acid to a relatively acidic "leaving group". Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isocyanates or isothiocyanates, which are prepared from amines and phosgene or thiophosgene, respectively. Polymers containing azide, alkyne and tetrazine are particularly useful for conjugation to click group-modified substrates such as the antibodies modified by a click group-containing activated esters.

Polymers containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods.

In one aspect of the invention, the polymer conjugates of the invention are used to directly stain or label a sample so that the sample can be identified or quantitated. For instance, such polymer conjugates may be added as part of an assay for a biological target analyte, as a detectable tracer element in a biological or non-biological fluid; or for such purposes as photodynamic therapy of tumors, in which a polymer conjugated sample is irradiated to selectively destroy tumor cells and tissues; or to photoablate arterial plaque or cells, usually through the photosensitized production of singlet oxygen. In one preferred embodiment, polymer conjugate is used to stain a sample that comprises a ligand for which the conjugated biological substrate is a complementary member of a specific binding pair (e.g. Table 4).

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

TABLE 4

Representative specific binding pairs

| Antigen | Antibody |
|---|---|
| Biotin | Anti-biotin or avidin or streptavidin or neutravidin |
| IgG* | Protein A or protein G or anti-IgG antibody |
| Drug | Drug receptor |
| Toxin | Toxin receptor |
| Carbohydrate | Lectin or carbohydrate receptor |
| Peptide | Peptide receptor |
| Nucleotide | Complimentary nucleotide |
| Protein | Protein receptor |
| Enzyme substrate | Enzyme |
| DNA (RNA) | aDNA (aRNA)** |
| Hormone | Hormone receptor |
| Psoralen | Nucleic acid |
| Target molecule | RNA or DNA aptamer |
| Ion | Ion chelator |

*IgG is an immunoglobulin;
**aDNA and aRNA are the antisense (complementary) strands used for hybridization Example 1. The Preparation of Compound 2

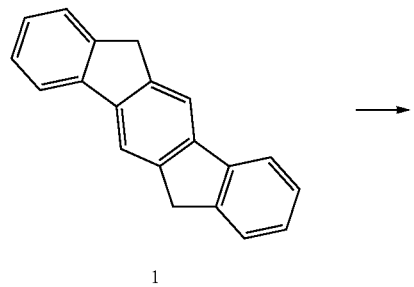

1

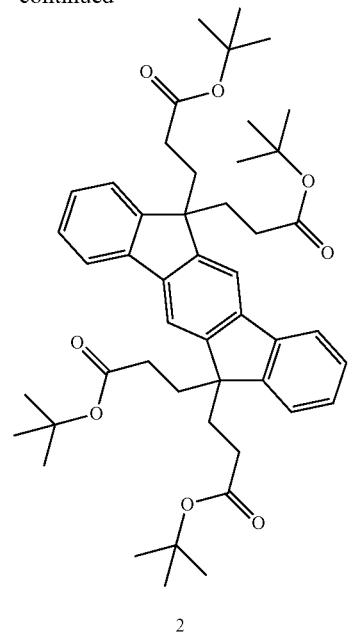

2

Compound 1 is prepared as described by Hsiao, Chien-Chi et al, Advanced Synthesis & Catalysis, 2010, 352(18), 3267-3274. To the solution of Compound 1 (3.97 g) and TBAB (1.00 g) in toluene (80 mL) is added t-butyl acrylate (11.4 mL) in ice bath under Ar protection, followed by the addition of 50% NaOH (80 mL). The mixture is stirred at room temperature for 2.5 hours and ice-water is added. The reaction mixture is extracted by dichloromethane twice, dried with sodium sulfate, filtered and concentrated. The residue is purified by flash chromatography (hexane-chloroform, 0-10%) to give Compound 2 as a white solid.

Example 2. The Preparation of Compound 3

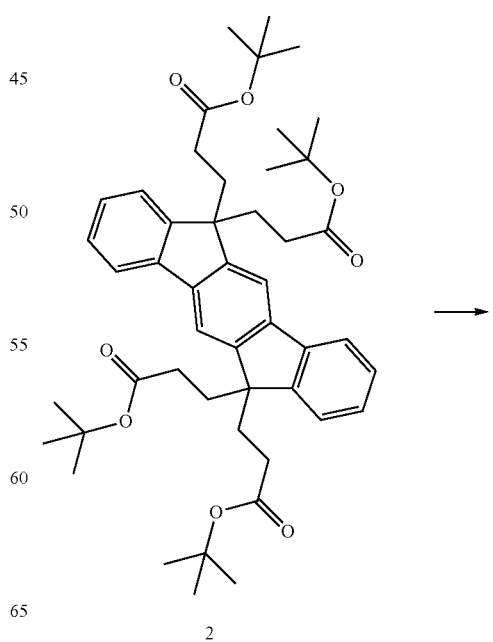

2

-continued

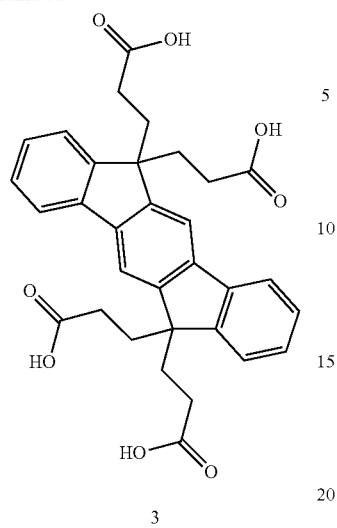

3

-continued

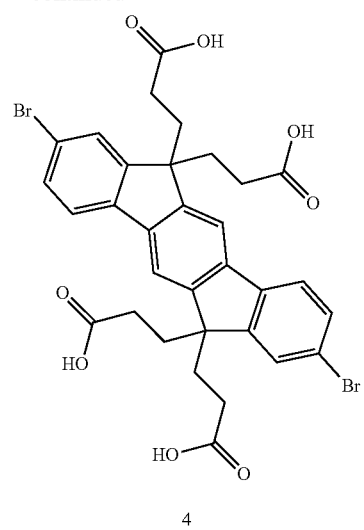

4

To the solution of Compound 2 (8.33 g) and anisole (9.4 mL) in dichloromethane (80 mL) are added trifluoroacetic acid (40 mL). The reaction mixture is stirred at room temperature for 5 hours and then concentrated, azeotroped with dichloromethane twice. The residue is triturated with ether (100 mL), filtered and dried to give compound 3 as a white solid.

Compound 3 (1.03 g) is sonicated in DMF (30 mL). To the DMF solution, bromine (0.2 mL) is added in ice bath and the reaction mixture is stirred at room temperature. More bromine (0.2 mL each, four times) is added until complete conversion to the desired product. The mixture is poured into a sodium sulfite solution (7.5 g in 500 mL water) with stirring. The white precipitate is collected, washed with 0.1% trifluoroacetic acid solution and lyophilized to give compound 4 as a white solid.

Example 3. The Preparation of Compound 4

Example 4. The Preparation of Compound 5

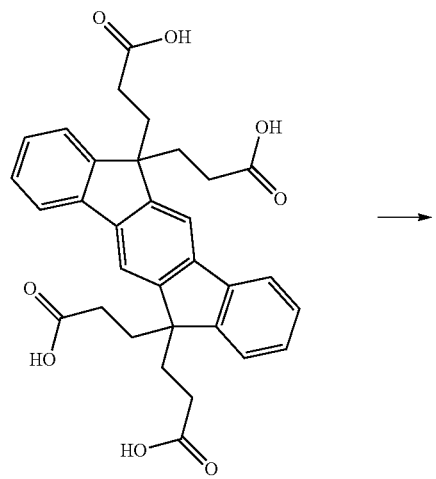

3

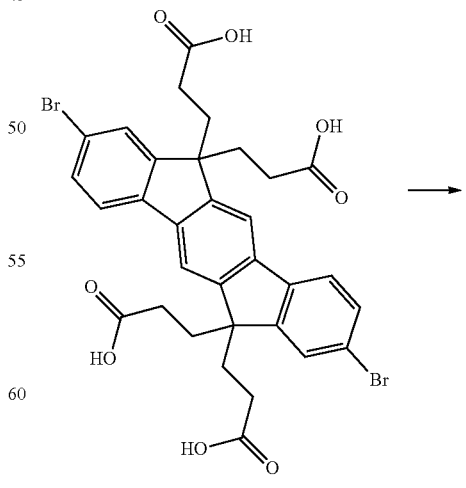

4

49

-continued

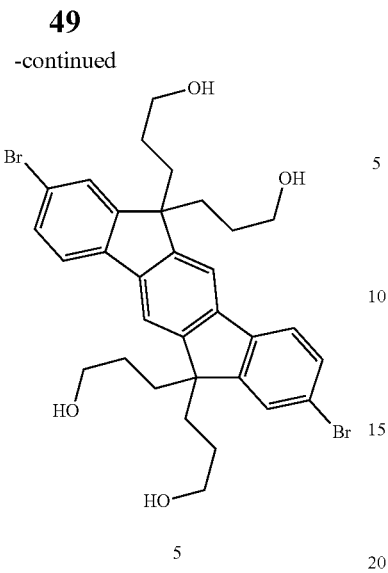

5

To the solution of Compound 4 (2.43 g) in tetrahydrofuran (80 mL) is added Et$_3$N (5.82 mL), then ethyl chloroformate (2 mL) in ice bath. The reaction mixture is stirred at room temperature for 1 hour and filtered. The filtrate is concentrated and dissolved in tetrahydrofuran (90 mL). To the tetrahydrofuran solution NaBH$_4$ (1.05 g) is added in ice bath, followed by water (7.5 mL) dropwise. The tetrahydrofuran solution is stirred for 30 minutes, and the mixture is concentrated and diluted with water. The white precipitate is collected, washed with water and lyophilized to give compound 5 as a white solid.

Example 5. The Preparation of Compound 6

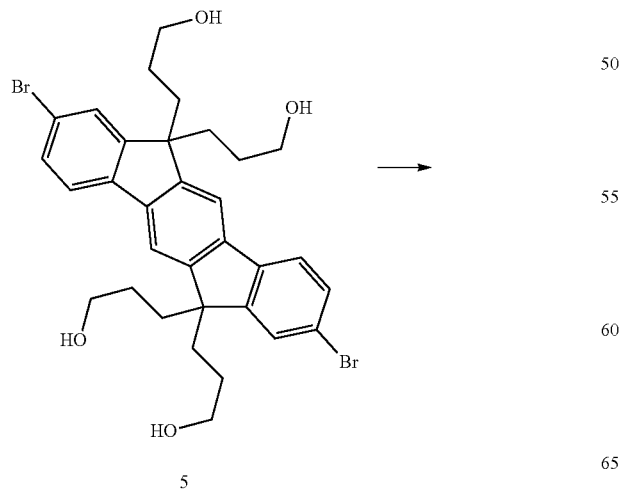

5

50

-continued

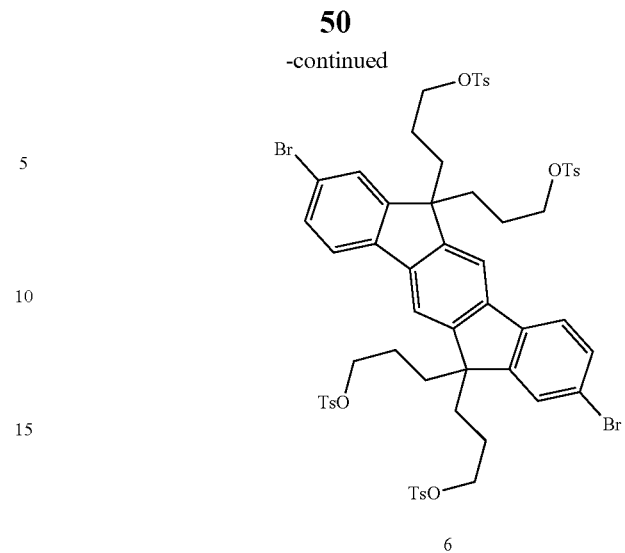

6

Compound 5 (0.646 g) is mixed with TsCl (1.16 g), Et$_3$N (1.7 mL) and DABCO (0.23 g) in tetrahydrofuran (24 mL) and dichloromethane (50 mL). The mixture is stirred at room temperature for 24 hours and concentrated. The residue is dissolved in dichloromethane, washed with saturated sodium bicarbonate solution and brine, dried with sodium sulfate, filtered and concentrated. The residue is purified by flash chromatography (hexane-dichloromethane, 50-100%) to give Compound 6 as a white solid.

Example 6. The Preparation of Compound 7

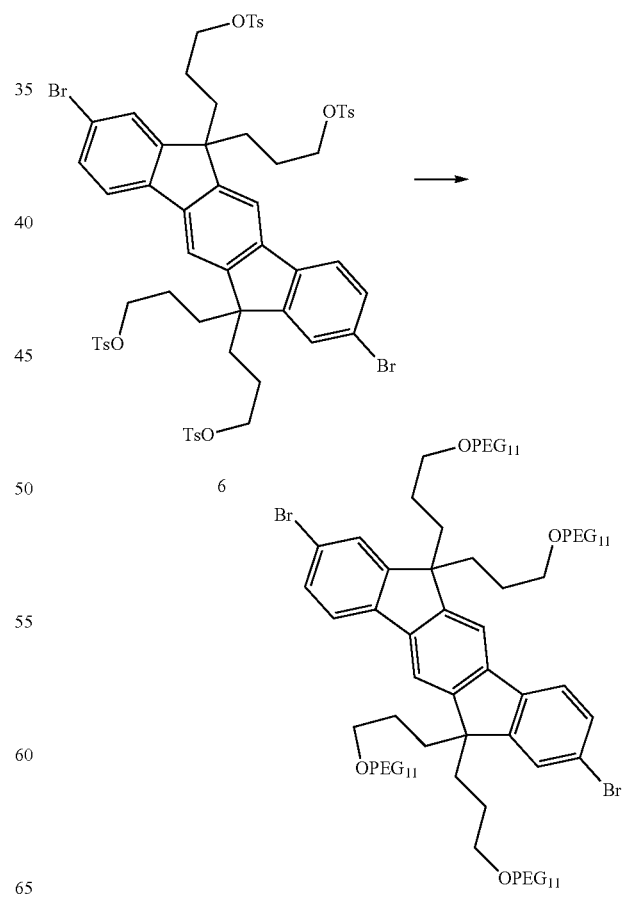

PEG$_{11}$-OH (1.638 g) is added NaH (0.127 g) in tetrahydrofuran (12 mL) in ice bath, and the reaction mixture is stirred for 15 minutes. To the tetrahydrofuran solution is added Compound 6 (0.666 g) in tetrahydrofuran (12 mL), and the reaction mixture is stirred at room temperature for 24 hours. The mixture is concentrated, and mixed with water. The suspension is extracted with EtOAc for four times, dried with sodium sulfate, filtered and concentrated. The residue is purified by flash chromatography (dichloromethane-MeOH, 0-10%) to give compound 7 as pale yellow oil.

Example 7. The Preparation of Compound 8

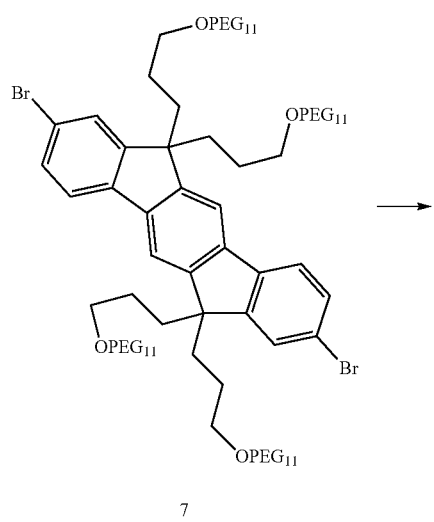

7

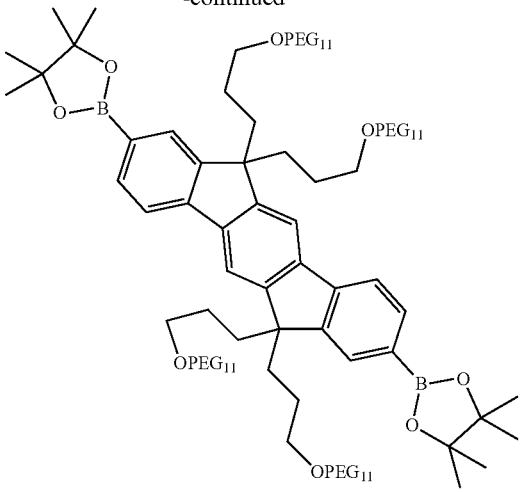

8

To the solution of Compound 7 (0.8 g) in DMF (5 mL) is added bis(pinacolato)diboron (0.338 g), KOAc (0.26 g), followed with Pd(dppf)Cl2 (0.025 g). The reaction mixture is bubbled with Argon for 10 minutes and then heated at 80° C. for 2 hours. The mixture is concentrated, and mixed with water. The suspension is extracted with EtOAc for four times, dried with sodium sulfate, filtered and concentrated. The residue is purified by flash chromatography (dichloromethane-MeOH, 0-10%) to give Compound 8 as pale yellow oil.

Example 8. The Preparation of Compound 10

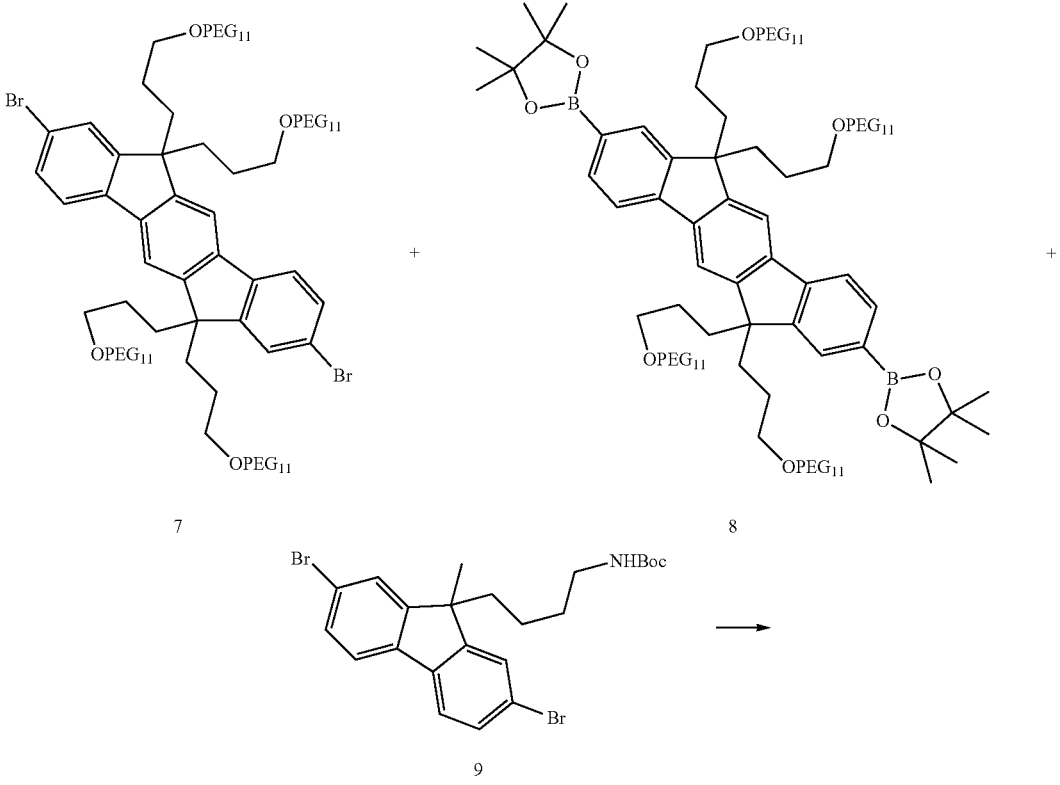

-continued

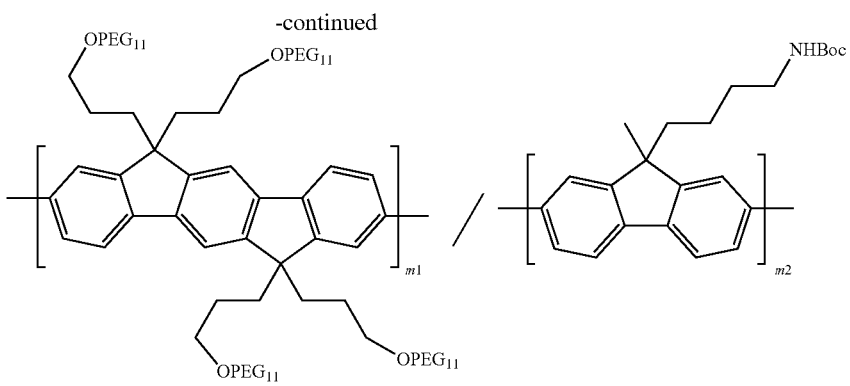

Under the argon, to the solution of Compound 7 (0.4 g), Compound 8 (0.58 g) and Compound 9 (0.021 g) in DMF (6 mL) in a Schlenk flask, K2CO3 in water (2 M, 4 mL) is added, followed with palladium tetrakis(triphenylphosphine) (0.018 g). The mixture is degassed via three freeze-pump-thaw cycles, and heated to 80° C. for 24 hours. At room temperature, to the reaction Mixture, phenylboronic acid pinacol ester (0.053 g) is added under the argon, and heated to 80° C. for 2 hours. At room temperature, to the reaction mixture, EDTA (0.1 g) in 20% EtOH/H2O (20 mL) is added and stirred at room temperature for 2 hours. The resulting mixture is filtered through a 0.45 μm cup filter. The filtered solution is diluted to the concentration of 2 mg/mL using 20% EtOH/H2O. The resulting dilution is dialyzed into 20% EtOH/H2O using a tangential flow filtration system with 30 kD and 750 kD molecular weight cutoff membrane until there is less than 0.1 mg/mL of polymer in the elutant. The solution is concentrated and lyophilized to give Compound 10 as a yellow solid.

Example 9. The Preparation of Compound 11 (CPCP11)

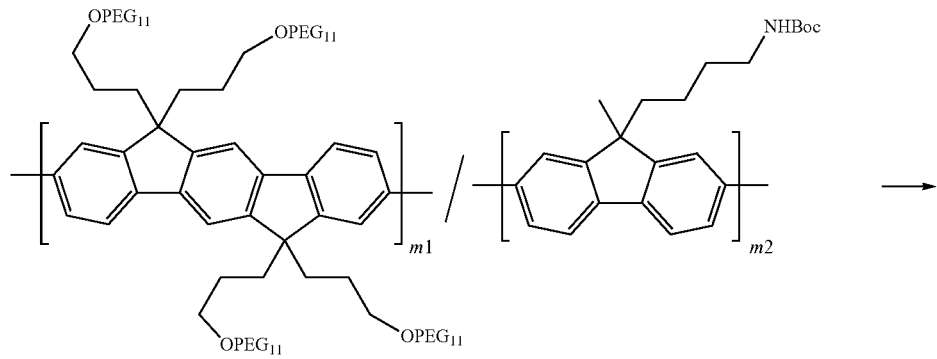

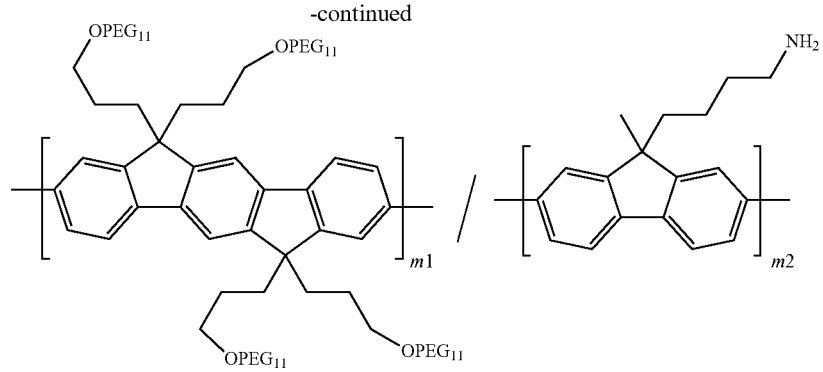
11
At room temperature, to the solution of Compound 10 (500 mg) in dichloromethane (8 ml), trifluoroacetic acid (4 mL) is added, followed by anisole (0.05 mL). The reaction mixture is stirred at room temperature for 2-3 hours. The solvent is removed and dried under high vacuum overnight to give Compound 11 as pale yellow oil.
Example 10. The Preparation of Compound 22
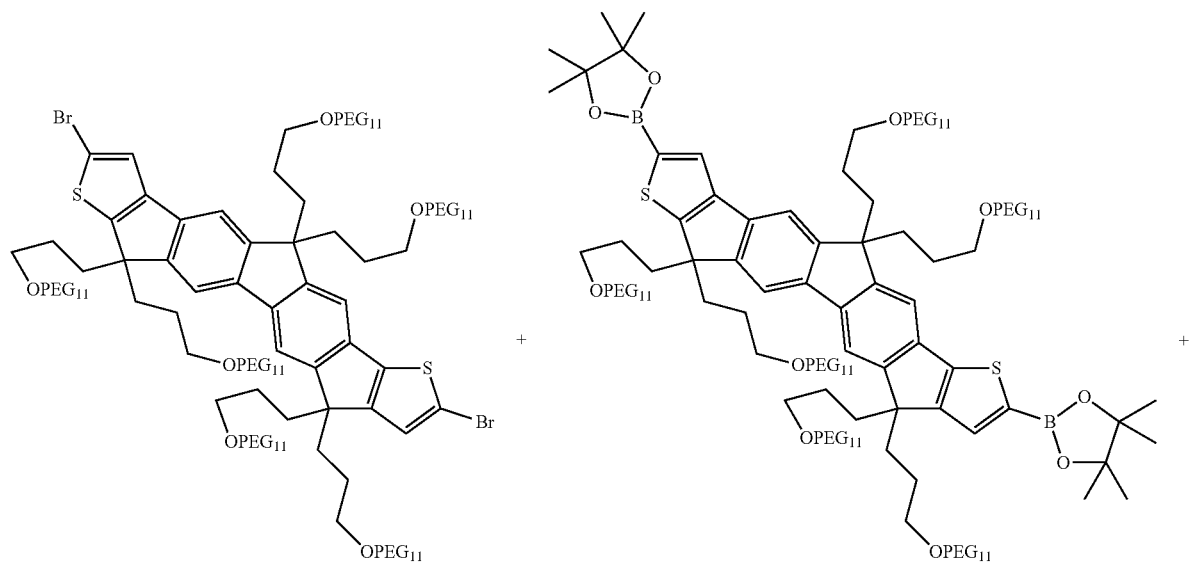
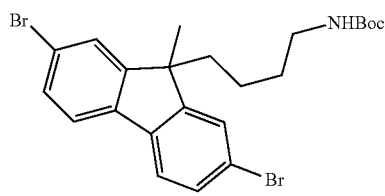

-continued
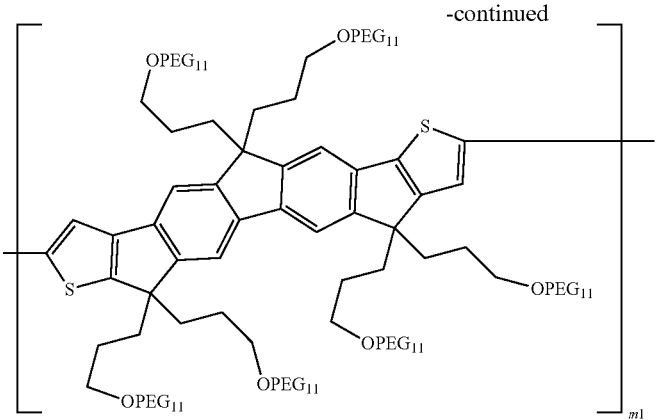
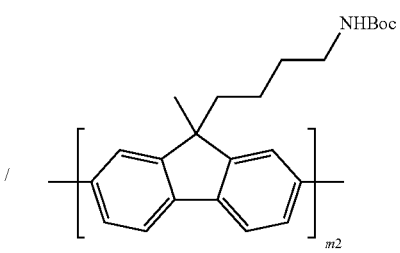
22
Monomers 20 and 21 are analogously prepared using methods described by e.g., H. Feng et al. (Chemistry of Materials 2017, 29(18), 7908-7917), and polymerized with Monomer 9 as described in the procedure of Compound 10 (See Example 8).
Example 11. The Preparation of Compound 23 (CPCP23)
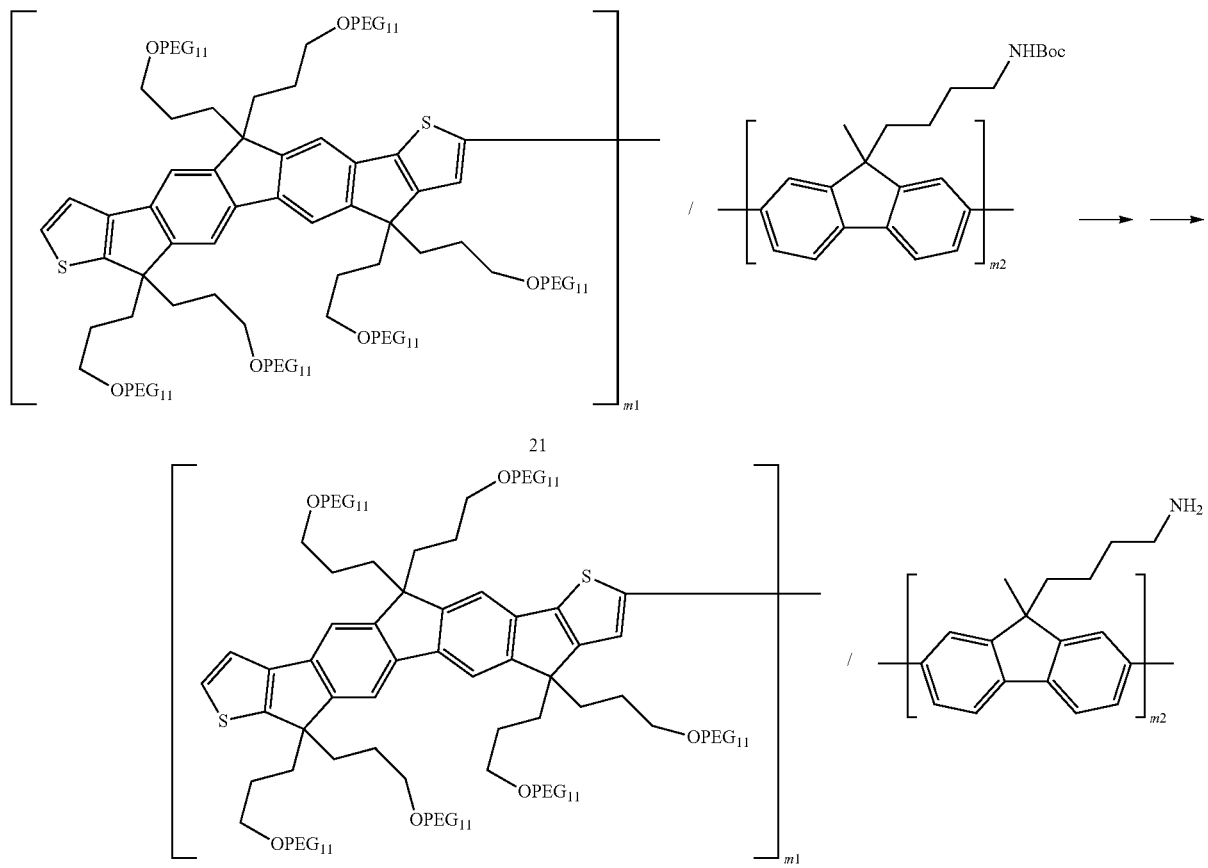

Polymer 22 is analogously converted Polymer 23 as described in the procedure of Compound 9 (See Example 9).

Example 12. The Preparation of CPCP Succinimidyl Ester (CPCP30)

To the solution of Compound 11 (100 mg) in DMF (10 ml) is added 0.1 ml DMF solution of di(N-succinimidyl) glutarate (1 mg, AAT Bioquest) and 10 µl triethylamine. The reaction mixture is stirred at room temperature for 2 hours, and concentrated under high vacuum to remove DMF. The residue is washed with ether for multiple times until most of the unreacted di(N-succinimidyl) glutarate is removed. The residue is quickly dissolved in cold acidic water (pH=5), and extracted with ether for three times. The aqueous solution is frozen and dried to give the desired CPCP succinimidyl ester.

Example 13. The Preparation of CPCP Maleimide (CPCP31)

To the solution of Compound 11 (100 mg) in DMF (10 ml) is added 0.1 ml DMF solution of 3-maleimidopropionic acid N-hydroxysuccinimide ester (1 mg, AAT Bioquest) and 10 µl triethylamine. The reaction mixture is stirred at room temperature for 2 hours, and concentrated under high vacuum to remove DMF. The residue is dissolved in acidic water (pH=5), and extracted with ethyl acetate for three times. The aqueous solution is frozen and dried to give the desired CPCP maleimide.

Example 14. The Preparation of CPCP Dichlorotriazine (CPCP32)

To the solution of Compound 11 (100 mg) in DMF (10 ml) is added 0.1 ml DMF solution of cyanuric chloride (1 mg, Sigma) and 10 µl triethylamine. The reaction mixture is stirred at room temperature for 3 hours, and concentrated under high vacuum to remove DMF. The residue is washed with ethyl acetate for multiple times until most of the unreacted cyanuric chloride is removed. The residue is quickly dissolved in cold water (pH=6), and extracted with ethyl acetate for three times. The aqueous solution is frozen and dried to give the desired CPCP dichlorotriazine.

Example 15. The Preparation of CPCP-DBCO (CPCP33)

To the solution of Compound 11 (100 mg) in DMF (10 ml) is added 0.1 ml DMF solution of DBCO-PEG4 succinimidyl ester (1 mg, AAT Bioquest) and 10 µl triethylamine. The reaction mixture is stirred at room temperature for 3 hours, and concentrated under high vacuum to remove DMF. The residue is washed with ethyl acetate for multiple times until most of the unreacted DBCO-PEG4 succinimidyl ester is removed. The residue is dissolved in water, and extracted with ethyl acetate for three times. The aqueous solution is frozen and dried to give the desired CPCP DBCO.

Example 16. The Preparation of CPCP TCO (CPCP34)

To the solution of Compound 11 (100 mg) in DMF (10 ml) is added 0.1 ml DMF solution of TCO-PEG4 succinimidyl ester (1 mg, AAT Bioquest) and 10 µl triethylamine. The reaction mixture is stirred at room temperature for 3 hours, and concentrated under high vacuum to remove DMF. The residue is washed with ethyl acetate for multiple times until most of the unreacted TCO-PEG4 succinimidyl ester is removed. The residue is dissolved in water, and extracted with ethyl acetate for three times. The aqueous solution is frozen and dried to give the desired CPCP TCO.

Example 17. The Preparation of CPCP Methyltetrazine (CPCP35)

To the solution of Compound 11 (100 mg) in DMF (10 ml) is added 0.1 ml DMF solution of methyltetrazine-PEG4 succinimidyl ester (1 mg, AAT Bioquest) and 10 µl triethylamine. The reaction mixture is stirred at room temperature for 3 hours, and concentrated under high vacuum to remove DMF. The residue is washed with ethyl acetate for multiple times until most of the unreacted methyltetrazine-PEG4 succinimidyl ester is removed. The residue is dissolved in water, and extracted with ethyl acetate for three times. The aqueous solution is frozen and dried to give the desired CPCP methyltetrazine.

Example 18. The Preparation of CPCP Azide (CPCP36)

To the solution of Compound 11 (100 mg) in DMF (10 ml) is added 0.1 ml DMF solution of azido-PEG4 succinimidyl ester (1 mg, AAT Bioquest) and 10 µl triethylamine. The reaction mixture is stirred at room temperature for 3 hours, and concentrated under high vacuum to remove DMF. The residue is washed with ethyl acetate for multiple times until most of the unreacted azido-PEG4 succinimidyl ester is removed. The residue is dissolved in water, and extracted with ethyl acetate for three times. The aqueous solution is frozen and dried to give the desired CPCP azide.

Example 19. The Preparation of CPCP Alkyne (CPCP37)

To the solution of Compound 11 (100 mg) in DMF (10 ml) is added 0.1 ml DMF solution of alkynyl-PEG4 succinimidyl ester (1 mg, AAT Bioquest) and 10 µl triethylamine. The reaction mixture is stirred at room temperature for 3 hours, and concentrated under high vacuum to remove DMF. The residue is washed with ethyl acetate for multiple times until most of the unreacted alkynyl-PEG4 succinimidyl ester is removed. The residue is dissolved in water, and extracted with ethyl acetate for three times. The aqueous solution is frozen and dried to give the desired CPCP alkyne.

CPCP32 can be analogously converted to thiophene-containing CPCP succinimidyl ester (CPCP38), CPCP maleimide (CPCP39), CPCP dichlorotriazine (CPCP40), CPCP-DBCO conjugate (CPCP41), CPCP-TCO conjugate (CPCP42), CPCP azide (CPCP43) and CPCP alkyne (CPCP44) respectively according to the procedures of Examples 12 to 19.

Example 20. The Preparation of iFluor 594-Labeled and TCO-Functionalized CPCP (CPCP50)

To the solution of Compound 11 (100 mg) in DMF (10 ml) is added 0.1 ml DMF solution of 4:1 iFluor 594 succinimidyl ester and iFluor 594 TCO-PEG4 succinimidyl ester (1 mg, AAT Bioquest) and 10 µl triethylamine. The reaction mixture is stirred at room temperature for 3 hours, and concentrated under high vacuum to remove DMF. The residue is dissolved in water, and dialyzed to remove the unreacted iFluor dyes. The aqueous solution is frozen and dried to give the desired iFluor 594-labeled and TCO-functionalized CPCP. Other fluorescent dye-labeled and functionalized CCP polymers can be analogously prepared as previously reported (See U.S. Pat. No. 9,896,538 to Diwu et al; U.S. Pat. Nos. 8,455,613; 8,354,239; 8,362,193; and 8,575,303 to Gaylord, et al.; also WO 2013/101902 to Chiu et al).

The above examples of some synthetic strategies for the selected polymers of the invention, as well as their characterization, synthetic precursors, conjugates and methods of use are provided in the examples for illustration. Their further modifications and permutations are obvious to one skilled in the art. For example, the second fluorophores conjugated to the polymers of the invention can be readily selected from a large number of the commercial dyes as listed in Table 2 to make the polymers have the different desired spectral properties. In addition, the polymers of the invention can be further functionalized with a different reactive functional group pairs as listed in Table 3. The well-known clickable groups can also be added to the polymers of the invention for the biorthogonal chemistry-based conjugations (see P. Agarwal and R. Bertozzi, Bioconjugate Chem., 2015, 26, 176-192; K. Lang and J. Chin, Chem. Reviews, 2014, 114, 4764-4806; M. D. Best, Biochemistry, 2009, 48, 6571-6584). Some other alternative methods for polymer functionalization are well described in the literature (see U.S. Pat. Nos. 8,158,444; 8,455,613; 8,354,239; 8,362,193; and 8,575,303 to Gaylord, et al.; also WO 2013/101902 to Chiu et al).

Example 21. Preparation of CPCP-Labeled Goat Anti-Mouse IgG Conjugate (CPCP51)

Goat Anti-Mouse IgG (GAM) is dissolved in 10 mM $NaHCO_3$ (pH 8.2) buffer to make a 5 mg/mL solution. To the aqueous GAM protein solution is added the DMF solution of CPCP30 (20 equivalents). The solution is rotated at room temperature for 3 hours and the reaction mixture is transferred to an Amicon Ultra filter (MWCO=10 kDa) to remove DMF. The protein is recovered into the initial volume with PBS buffer.

Cation exchange chromatography is used to remove free polymer. Conjugation mixture is loaded to UNOsphere™ S resin (Bio-Rad) in low salt buffer [50 mM MES Buffer (pH=5.0)], and incubated at room temperature for 10 minutes, repeatedly loading the sample for 3 times to get the maximum binding. After loading, the medium is washed with low salt buffer to the baseline (until the absorbance at 414 nm is lower than 0.01) to remove all free polymer. The retained conjugated polymer dye-GAM conjugate on the cation exchange resin is released by elevating both the pH and ionic strength with high salt phosphate buffer [10 mM phosphate buffer (pH=7.4)+1.0M NaCl buffer/methanol, 90/10]. Protein A and Protein G affinity resins can also be used to remove free polymer with comparable results. A HiTrap Protein G HP 1 mL column (GE Lifesciences) is pre-equilibrated with 10 mM Phosphate buffer, pH 7.4, and the SEC-purified product is slowly injected at <1 mg/mL and allowed to incubate for 30 minutes to bind. The column is washed with >10 column volumes of 10 mM Phosphate buffer to wash unbound polymer material off while monitoring absorption of the eluate at 280 nm and 414 nm to ensure all excess material is removed. The conjugate is eluted by washing the column with 4 column volumes of 0.1 M Glycine pH 2.3. The eluted fractions are combined and pH-adjusted back to neutral using 1 M Tris pH 8. After free polymer is removed, the conjugate solution is concentrated with Amicon Ultra Filter (MWCO=30 kD) and loaded to a size exclusion column (Superdex 200, GE life sciences) to separate conjugate and unconjugated antibody. The column is equilibrated with PBS buffer, and the conjugated polymer-antibody conjugate is eluted before free antibodies. For effective labeling, the degree of substitution should fall between 1-3 moles of conjugated polymer dye to one mole of antibody for most antibodies. As is well known in the art, the optima DOS depends on the properties of antibody to be labeled. The optimal labeling DOS is determined empirically by preparing a series of dye-conjugates over a range of DOS and comparing the desired signal/background. In some cases, a higher DOS may provide bright signal while in other cases higher DOS could reduce the affinity of the antibody to be labeled. Other CPCP-labeled antibody conjugates (e.g., CPCP30-labeled CD45 conjugate, CPCP55) can be analogously prepared.

Example 22. CPCP-Labeled Anti-CD Antibody Conjugates for Use in Flow Cytometry

Analyte-specific antibodies conjugated to a conjugated polymer dye of the present invention (i.e, labeled antibodies) are useful for the analysis of blood cells (for example, in whole blood samples) by flow cytometry. The labeled-antibodies are prepared as previously described (e.g., U.S. Pat. Nos. 9,719,998; 9,758,625; 8,158,444; 8,455,613; 8,354,239; 8,362,193; and 8,575,303 to Gaylord, et al.; U.S. Pat. No. 9,896,538 to Diwu et al.; WO 2013/101902 to Chiu et al.). These CPCP-labeled antibodies can be used to stain cellular proteins, and the labeled cells are detected using a flow cytometer. CPCP bioconjugates are evaluated by Stain Index, as defined by BD Biosciences on a flow cytometer. See, e.g., H. Maeker and J. Trotter, BD Biosciences Application Note: "Selecting Reagents for Multicolour Flow Cytometry", September 2009. The stain index reports a measure of the polymer's brightness, nonspecific binding. Flow cytometry provides a method through which to measure cells of a specific phenotype or analytes of interest on specific microspheres. This can be done with direct labeling of a primary antibody or, if signal amplification is desired, through a secondary antibody or the avidin-biotin complexation with avidin-polymer conjugates. Cells of interest are taken up in sufficient quantity, spun down, washed in DPBS+0.2% BSA and 0.05% $NaN_3$, then resuspended in staining buffer of conjugated polymer conjugates.

Example 22. Preparation of CPCP-Labeled Phalloidin Conjugate (CPCP60)

To aminophalloidin (1 mg, AAT Bioquest) and CPCP 30 (10 mg) in DMF (0.5 mL) is added N,N-diisopropylethyl-amine (25 µL). The mixture is stirred at room temperature for 3 hours. To this solution is added 5 mL of EtOAc. The solid is collected by centrifugation. The crude product is purified on SEPHADEX LH-20, eluting with water, followed by preparative Superdex 200 SEC column purification to give the pure phalloidin conjugate.

Example 23. The Staining of F-Actin Filaments with CPCP-Labeled Phalloidin Conjugates Actin is a globular, roughly 42-kDa protein found in almost all eukaryotic cells. It is also one of the most highly conserved proteins, differing by no more than 20% in species as diverse as algae and humans. CPCP30-labeled Phalloidin conjugate (CPCP60) selectively binds to F-actins.

Used at nanomolar concentrations, CPCP60 can be used for labeling, identifying and quantitating F-actins in formaldehyde-fixed and permeabilized tissue sections, cell cultures or cell-free experiments. Cells are fixed with formaldehyde and incubated after the addition of DMSO stock solution of CPCP conjugate. The cells are gently rinsed with PBS for 2 to 3 times to remove excess phalloidin conjugate. The cells are plated, sealed and imaged with a fluorescence microscope. Other CPCP conjugates can be analogously used to stain of F-actin filaments with different fluorescence colors.

Example 24. The Preparation of Compound 52

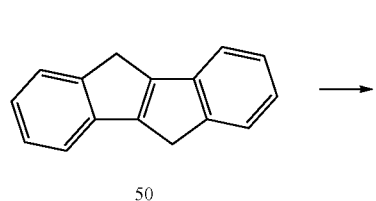

50

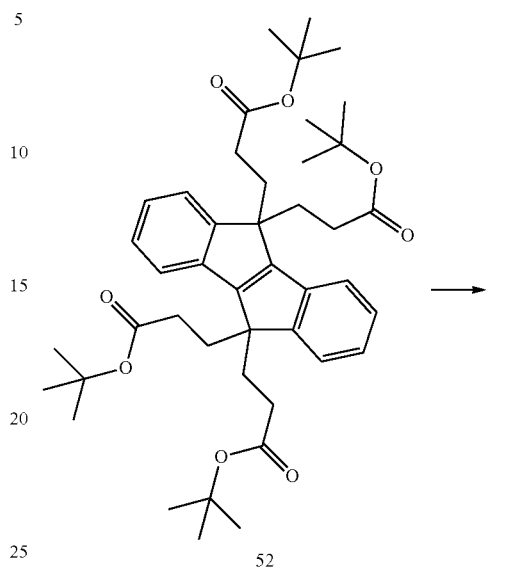

52

Example 25. The Preparation of Compound 53

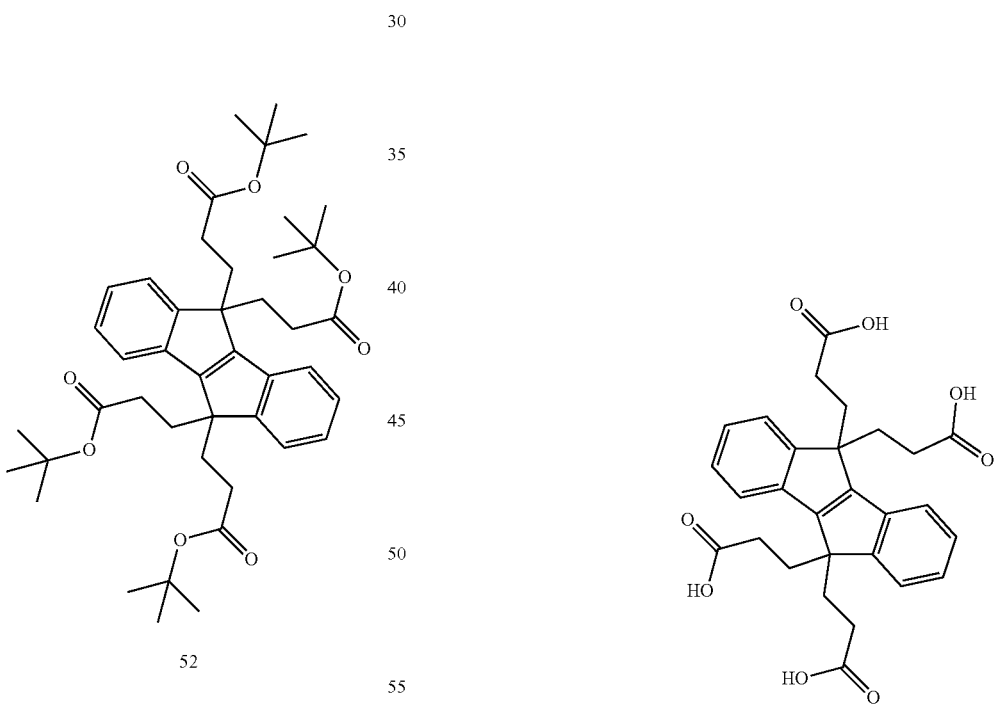

Compound 50 is prepared as described by B. Y, Kim et al, (See KR2013084952). To the solution of Compound 50 (3.19 g) and TBAB (1.00 g) in toluene (80 mL) is added t-butyl acrylate (11.4 mL) in ice bath under Ar protection, followed by the addition of 50% NaOH (80 mL). The mixture is stirred at room temperature for 2.5 hours and ice-water is added. The reaction mixture is extracted by dichloromethane twice, dried with sodium sulfate, filtered and concentrated. The residue is purified by flash chromatography (hexane-chloroform, 0-10%) to give compound 52 as a white solid.

To the solution of Compound 52 (8.33 g) and anisole (9.4 mL) in dichloromethane (40 mL) are added trifluoroacetic acid (20 mL). The reaction mixture is stirred at room temperature for 5 hours and then concentrated, azeotroped with dichloromethane twice. The residue is triturated with ether (100 mL), filtered and dried to give compound 53 as a white solid.

Example 26. The Preparation of Compound 54

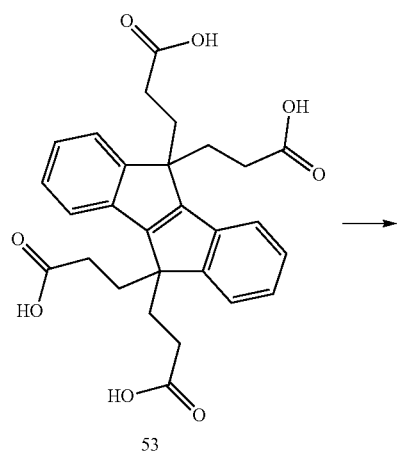
53

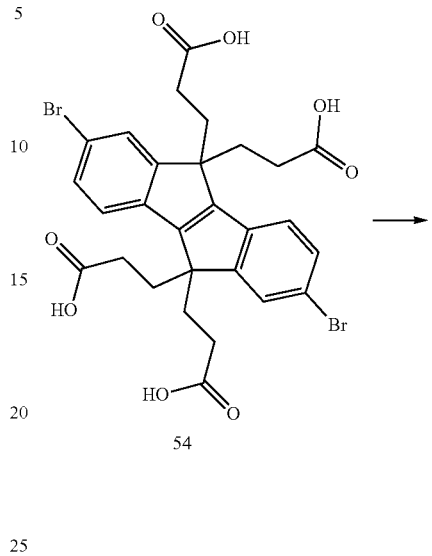
54

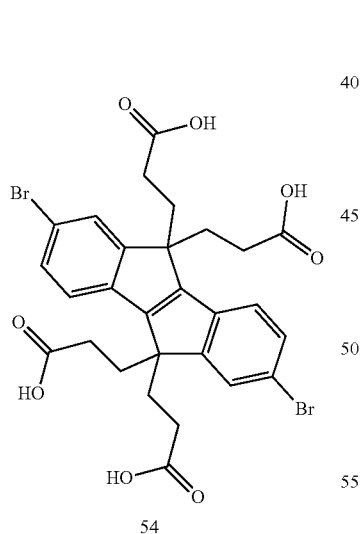
54

Compound 53 (0.93 g) is sonicated in DMF (25 mL). To the DMF solution, bromine (0.4 mL) is added in ice bath and the reaction mixture is stirred at room temperature until complete conversion to Compound 54. The mixture is poured into a sodium sulfite solution (7.5 g in 500 mL water) with stirring. The white precipitate is collected, washed with 0.1% trifluoroacetic acid solution and lyophilized to give compound 54 as a white solid.

Example 27. The Preparation of Compound 55

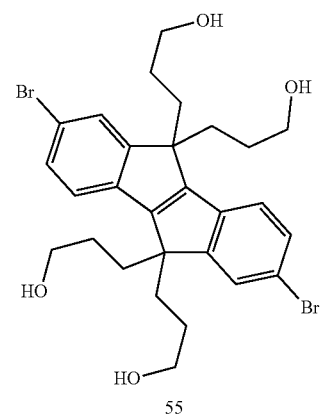
55

To the solution of Compound 54 (2.19 g) in tetrahydrofuran (80 mL) is added Et$_3$N (5.82 mL), then ethyl chloroformate (2 mL) in ice bath. The reaction mixture is stirred at room temperature for 1 hour and filtered. The filtrate is concentrated and dissolved in tetrahydrofuran (90 mL). To the tetrahydrofuran solution NaBH$_4$ (1.05 g) is added in ice bath, followed by the dropwise addition of water (7.5 mL). The reaction solution is stirred for 30 minutes, and concentrated and diluted with water. The resulted precipitate is collected, washed with water and lyophilized to give compound 55 as a white solid.

Example 28. The Preparation of Compound 56

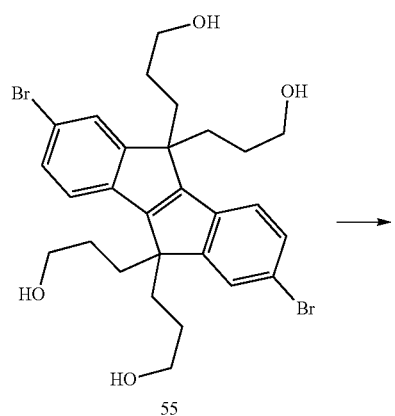

55

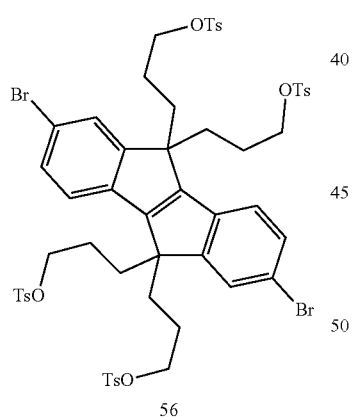

56

Compound 55 (0.58 g) is mixed with TsCl (1.16 g) and Et₃N (1.7 mL) in tetrahydrofuran (24 mL) and dichloromethane (50 mL). The mixture is stirred at room temperature for 24 hours and concentrated. The residue is dissolved in dichloromethane, washed with saturated sodium bicarbonate solution and brine, dried with sodium sulfate, filtered and concentrated. The residue is purified by flash chromatography (hexane-dichloromethane, 50-100%) to give Compound 56 as a white solid.

Example 29. The Preparation of Compound 57

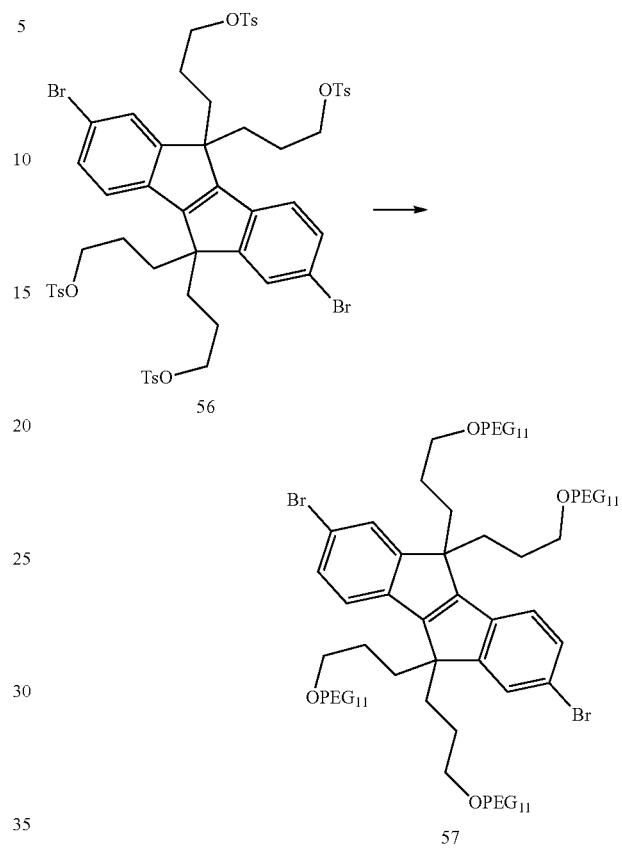

PEG$_{11}$-OH (1.64 g) is added NaH (0.13 g) in tetrahydrofuran (12 mL) in ice bath, and the reaction mixture is stirred for 15 minutes. To the tetrahydrofuran solution is added Compound 56 (0.60 g) in tetrahydrofuran (12 mL), and the reaction mixture is stirred at room temperature for 24 hours. The mixture is concentrated, and mixed with water. The suspension is extracted with EtOAc for four times, dried with sodium sulfate, filtered and concentrated. The residue is purified by flash chromatography (dichloromethane-MeOH, 0-10%) to give Compound 57 as pale yellow oil.

Example 30. The Preparation of Compound 58

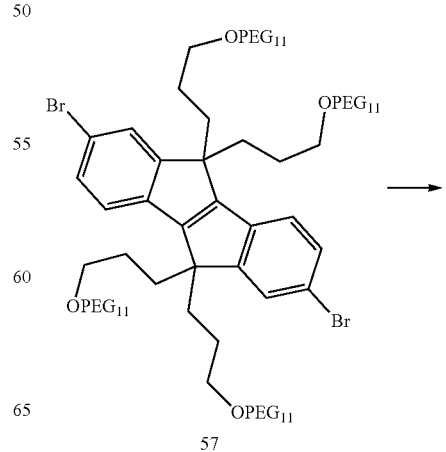

57

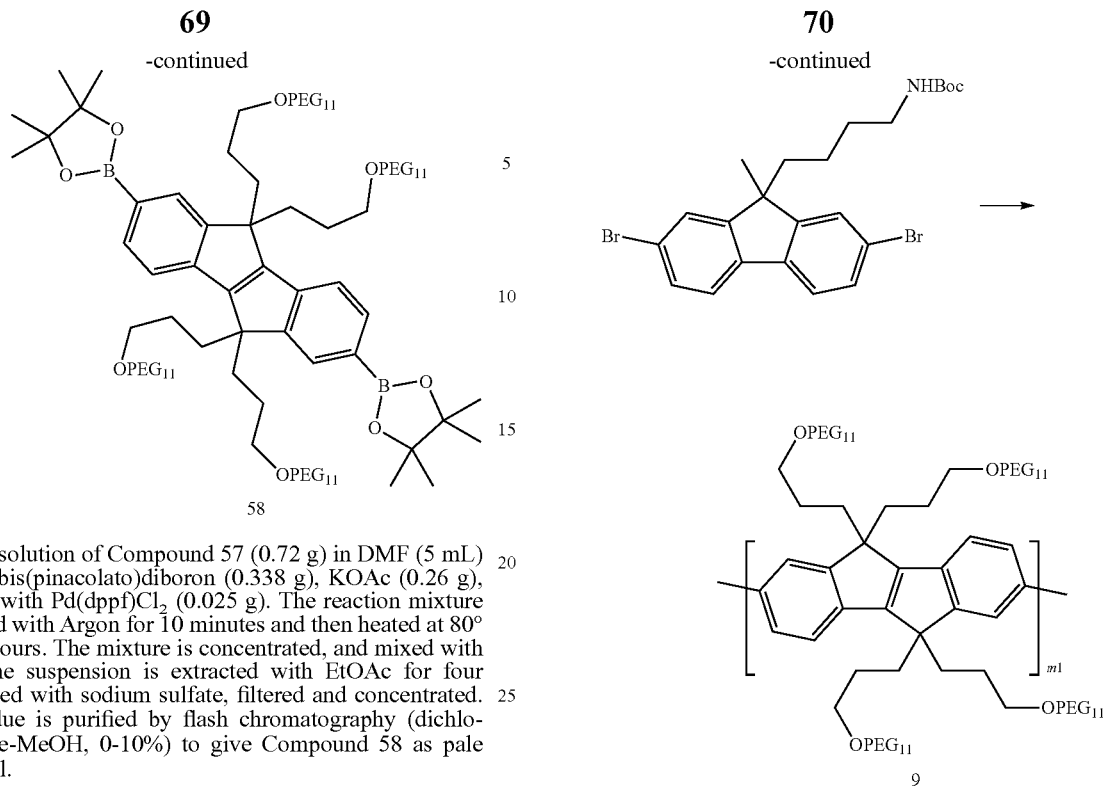

To the solution of Compound 57 (0.72 g) in DMF (5 mL) is added bis(pinacolato)diboron (0.338 g), KOAc (0.26 g), followed with Pd(dppf)Cl$_2$ (0.025 g). The reaction mixture is bubbled with Argon for 10 minutes and then heated at 80° C. for 2 hours. The mixture is concentrated, and mixed with water. The suspension is extracted with EtOAc for four times, dried with sodium sulfate, filtered and concentrated. The residue is purified by flash chromatography (dichloromethane-MeOH, 0-10%) to give Compound 58 as pale yellow oil.

Example 31. The Preparation of Compound 60

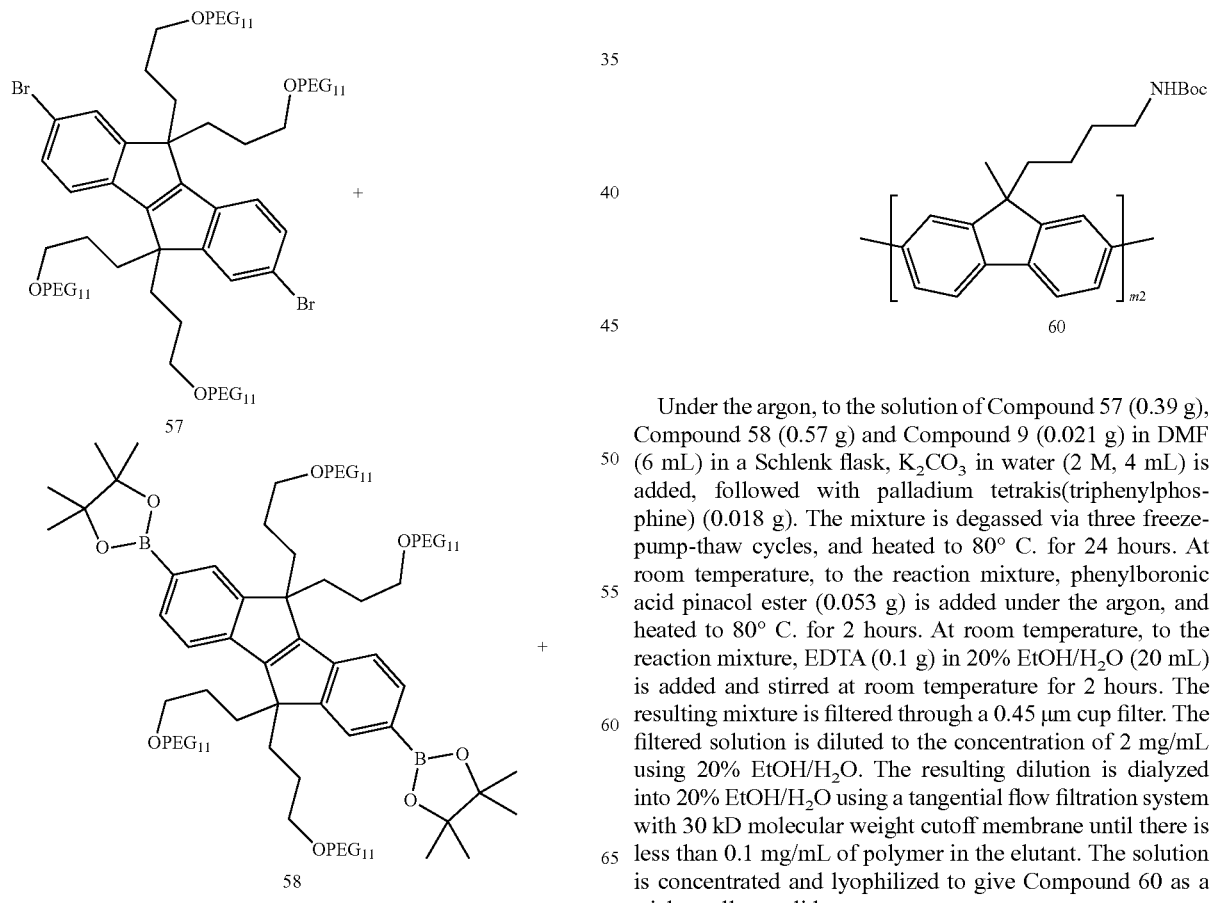

Under the argon, to the solution of Compound 57 (0.39 g), Compound 58 (0.57 g) and Compound 9 (0.021 g) in DMF (6 mL) in a Schlenk flask, K$_2$CO$_3$ in water (2 M, 4 mL) is added, followed with palladium tetrakis(triphenylphosphine) (0.018 g). The mixture is degassed via three freeze-pump-thaw cycles, and heated to 80° C. for 24 hours. At room temperature, to the reaction mixture, phenylboronic acid pinacol ester (0.053 g) is added under the argon, and heated to 80° C. for 2 hours. At room temperature, to the reaction mixture, EDTA (0.1 g) in 20% EtOH/H$_2$O (20 mL) is added and stirred at room temperature for 2 hours. The resulting mixture is filtered through a 0.45 μm cup filter. The filtered solution is diluted to the concentration of 2 mg/mL using 20% EtOH/H$_2$O. The resulting dilution is dialyzed into 20% EtOH/H$_2$O using a tangential flow filtration system with 30 kD molecular weight cutoff membrane until there is less than 0.1 mg/mL of polymer in the elutant. The solution is concentrated and lyophilized to give Compound 60 as a sticky yellow solid.

Example 32. The Preparation of Compound 61 (CPCP 100)

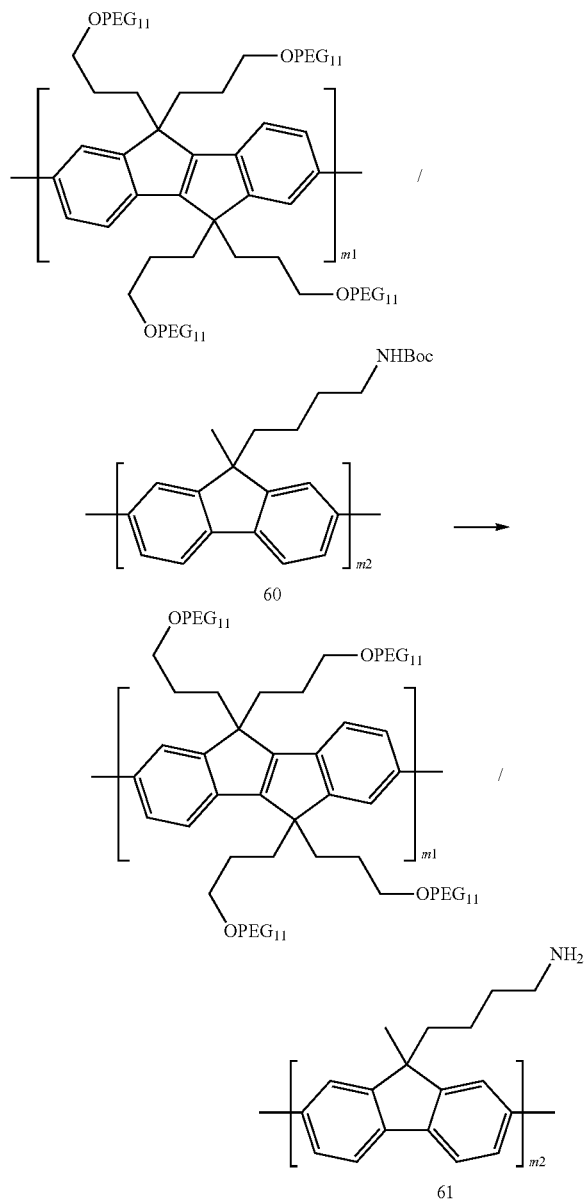

At room temperature, to the solution of Compound 60 (500 mg) in dichloromethane (8 ml), trifluoroacetic acid (4 mL) is added, followed by anisole (0.05 mL). The reaction mixture is stirred at room temperature for 2-3 hours. The solvent is removed and dried under high vacuum overnight to give Compound 61 as pale yellow oil.

Example 33. The Functionalization of CPCP 100

CPCP100 is converted to a variety of reactive CPCP 100 derivatives analogously as described in the procedures of Examples 12 to 20 to respectively give CPCP 100 succinimidyl ester (CPCP 110), CPCP 100 maleimide (CPCP 111), CPCP 100 dichlorotriazine (CPCP 112), CPCP100-DBCO (CPCP 113), CPCP 100 TCO (CPCP114), CPCP 100 methyltetrazine (CPCP115), CPCP 100 azide (CPCP 116), CPCP 100 alkyne (CPCP117) and iFluor 594-labeled and TCO-functionalized CPCP100 (CPCP118).

Example 34. The Preparation of CPCP100 Bioconjugates from the Functionalized Reactive CPCP100 Derivatives CPCP 100 succinimidyl ester (CPCP 110) is analogously converted to CPCP 100-labeled Goat Anti-Mouse IgG Conjugate (CPCP120), CPCP 100-Labeled anti-CD antibodies and CPCP 100-Labeled Phalloidin Conjugate (CPCP 130) as described in the procedures of Examples 21 to 23.

Example 35. The Preparation of Compound 72

The solution of 70 (1.52 g) and 71 (1.37 mg) in EtOH (60 mL) is refluxed for 15 minutes. EtOH is removed in vacuum. After 1 h under the high vacuum, the residue is dissolved in 2-propanol (60 mL) followed by adding concentrated $H_2SO_4$ (0.75 mL). The mixture is refluxed for 13 hours. After cooling to room temperature, the pH of solution is adjusted to 10 with 1M NaOH (50 mL) that is extracted with dichloromethane (3×80 mL). The combined dichloromethane solution is washed with brine and dried over anhydrous $Na_2SO_4$. Dichloromethane is removed in vacuum and the residue is purified by column (10% EtOAc in Hexanes) to give Compound 72 as white solid.

Example 36. The Preparation of Compound 76

-continued

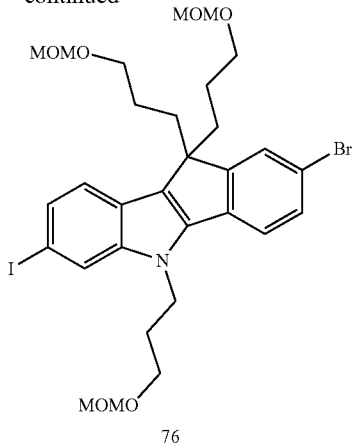
76

To the solution of 72 (1.11 g) in tetrahydrofuran (10 mL) is added t-BuOK (0.96 g) at room temperature under argon, followed by Compound 73 (1.65 g). The mixture is stirred at room temperature overnight. Water (50 mL) is added to quench reaction. Tetrahydrofuran is removed in vacuum. The residue is dissolved in dichloromethane, washed with brine, dried with sodium sulfate, filtered and concentrated. The residue is purified by column (70% EtOAc in Hexane) to give Compound 76 as white solid.

Example 37. The Preparation of Compound 77

To the solution of 76 (0.54 g) in MeOH (30 mL), concentrated HCl (0.5 mL) is added. The mixture is refluxed for 1 hour. After removing MeOH, water (50 mL) is added. The mixture is extracted with EtOAc, washed with brine, dried with sodium sulfate, filtered and concentrated. The residue is dissolved in dichloromethane (24 mL), then TEA (1.64 mL, 11.76 mmol) and TsCl (1121 mg, 5.88 mmol) were added at room temperature. The mixture is stirred at room temperature overnight. The mixture is washed with brine (3×20 mL). The dichloromethane layer is dried with sodium sulfate, filtered and concentrated. The residue is purified by column (50% EtOAc in Hexane) to give Compound 77 as white solid.

Example 38. The Preparation of Compound 79

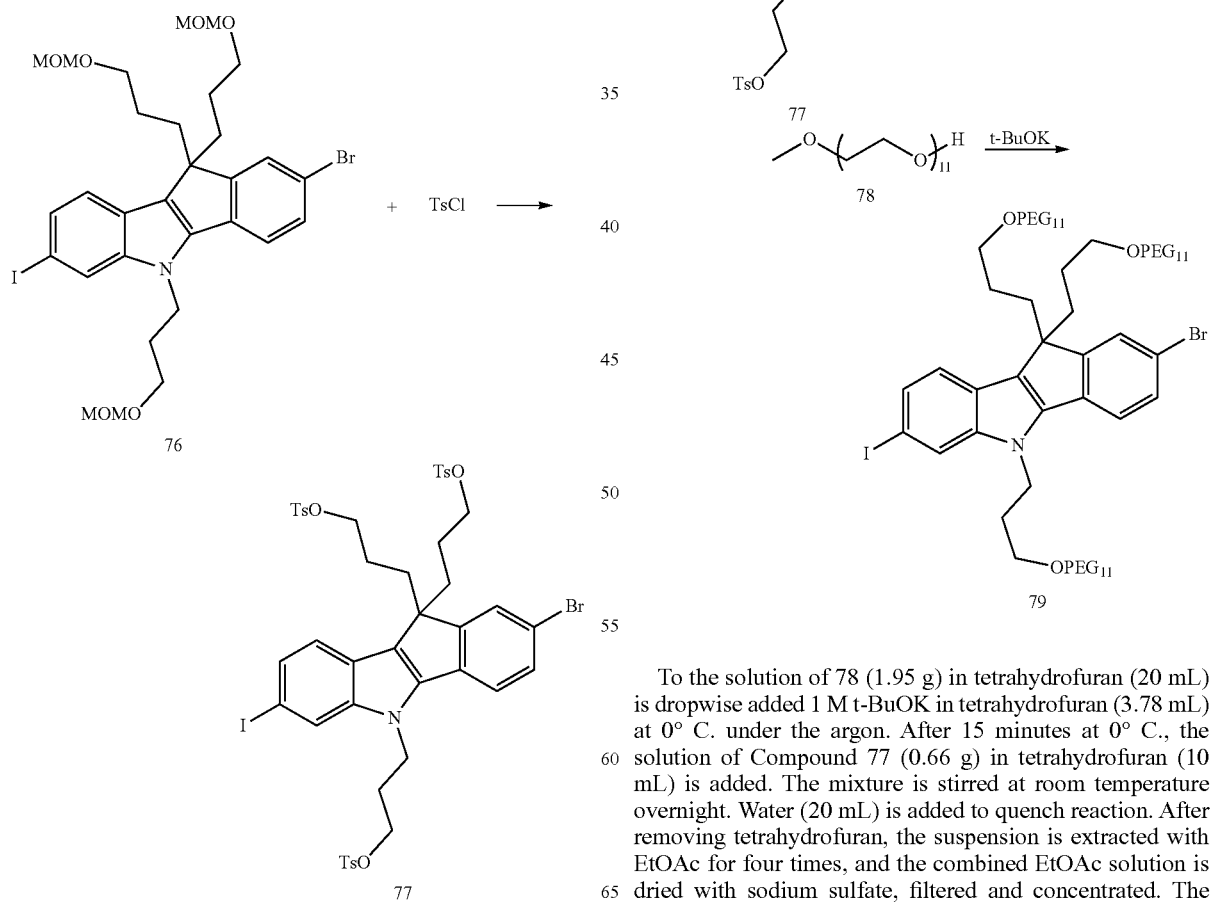

To the solution of 78 (1.95 g) in tetrahydrofuran (20 mL) is dropwise added 1 M t-BuOK in tetrahydrofuran (3.78 mL) at 0° C. under the argon. After 15 minutes at 0° C., the solution of Compound 77 (0.66 g) in tetrahydrofuran (10 mL) is added. The mixture is stirred at room temperature overnight. Water (20 mL) is added to quench reaction. After removing tetrahydrofuran, the suspension is extracted with EtOAc for four times, and the combined EtOAc solution is dried with sodium sulfate, filtered and concentrated. The residue is purified by flash chromatography (dichloromethane-MeOH, 0-10%) to give Compound 79 as colorless oil.

Example 39. The Preparation of Compound 80

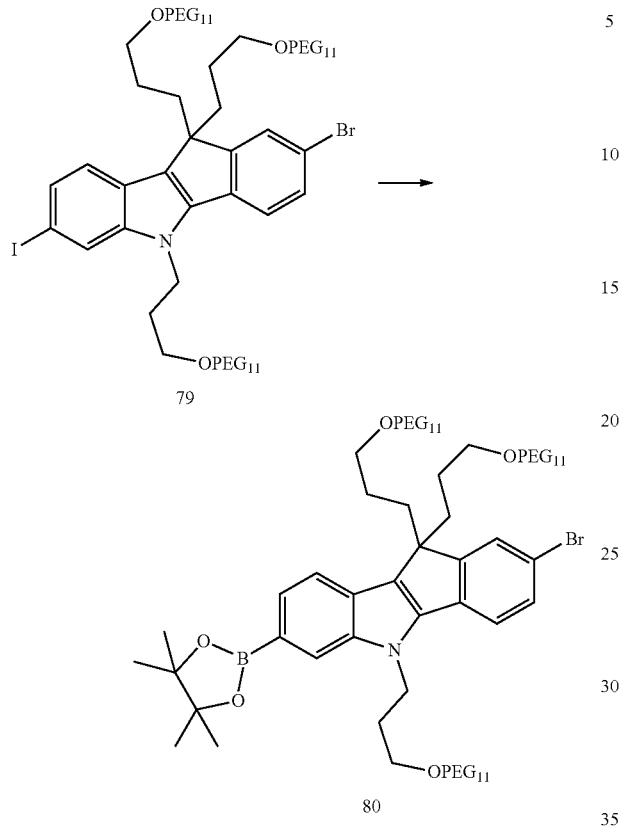

To the solution of Compound 79 (0.5 g) in DMF (3 mL) is added bis(pinacolato)diboron (0.085 g), KOAc (0.12 g), followed with Pd(dppf)Cl$_2$ (0.018 g). The reaction mixture is bubbled with argon for 10 minutes and then heated at 80° C. for 2 hours. The mixture is concentrated, and mixed with water. The suspension is extracted with EtOAc for four times, and the combined EtOAc solution is dried with sodium sulfate, filtered and concentrated. The residue is purified by flash chromatography (dichloromethane-MeOH, 0-10%) to give Compound 80 as pale yellow oil.

Example 40. The Preparation of Compound 82

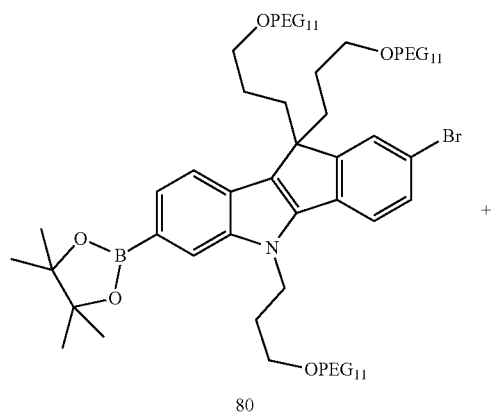

80

+

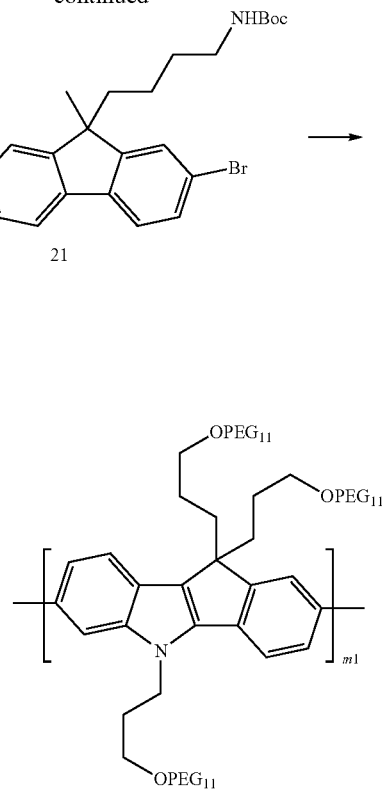

Under the argon, to the solution of Compound 80 (0.2 g) and Compound 21 (0.05 g) in DMF (3 mL) in a Schlenk flask, K$_2$CO$_3$ in water (2 M, 2 mL) is added, followed with palladium tetrakis(triphenylphosphine) (0.01 g). The mixture is degassed via three freeze-pump-thaw cycles, and heated to 80° C. for 24 hours. At room temperature, to the reaction mixture, phenylboronic acid pinacol ester (0.03 g) is added under the argon, and heated to 80° C. for 2 hours. At room temperature, to the reaction mixture, EDTA (0.1 g) in 20% EtOH/H$_2$O (20 mL) is added and stirred at room temperature for 2 hours. The resulting mixture is filtered through a 0.45 μm cup filter. The filtered solution is diluted to the concentration of 2 mg/mL using 20% EtOH/H$_2$O. The resulting dilution is dialyzed into 20% EtOH/H$_2$O using a tangential flow filtration system with 30 kD molecular weight cutoff membrane until there is less than 0.1 mg/mL of polymer in the elutant. The solution is concentrated and lyophilized to give Compound 82 as a sticky yellow solid.

Example 41. The Preparation of Compound 83 (CPCP 140)

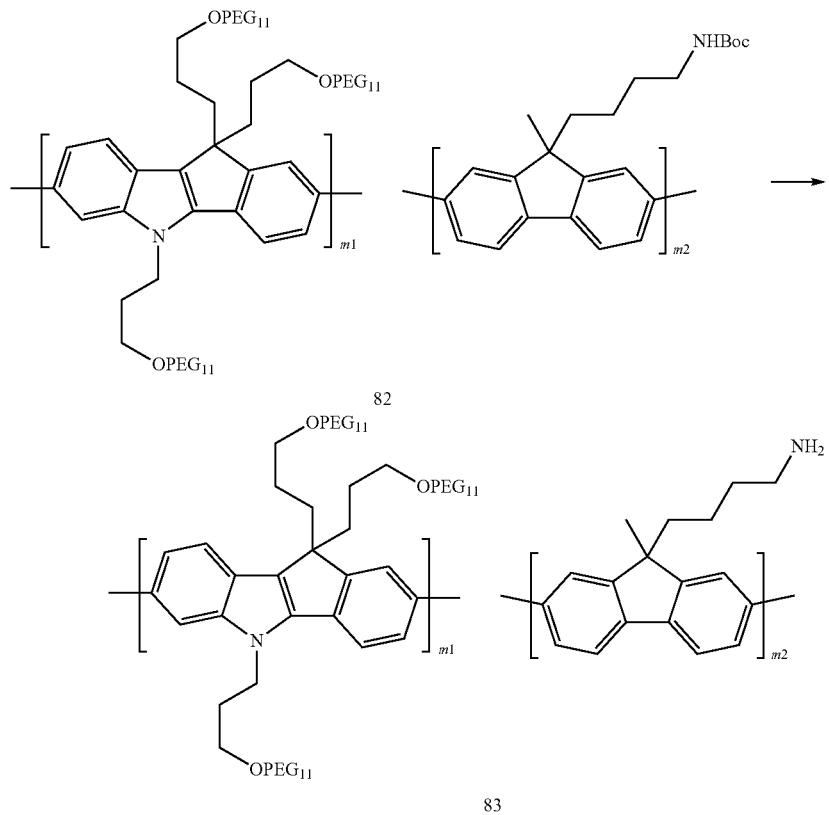

At room temperature, to the solution of Compound 82 (200 mg) in dichloromethane (4 ml), trifluoroacetic acid (2 mL) is added, followed by anisole (0.05 mL). The reaction mixture is stirred at room temperature for 2-3 hours. The solvent is removed and dried under high vacuum overnight to give Compound 83 as pale yellow oil.

Example 42. The Functionalization of CPCP 140

CPCP200 is converted to a variety of reactive CPCP 200 derivatives analogously as described in the procedures of Examples 12 to 17 to respectively give CPCP 200 succinimidyl ester (CPCP 150), CPCP 200 maleimide (CPCP 151), CPCP 200 dichlorotriazine (CPCP 152), CPCP200-DBCO (CPCP 153), CPCP 200 TCO (CPCP154), CPCP 200 methyltetrazine (CPCP155), CPCP 200 azide (CPCP 156), CPCP 200 alkyne (CPCP157) and iFluor 594-labeled and TCO-functionalized CPCP200 (CPCP158).

Example 43. The Preparation of CPCP200 Bioconjugates from the Functionalized Reactive CPCP200 Derivatives CPCP 200 succinimidyl ester (CPCP 150) is analogously converted to CPCP 200-labeled goat anti-mouse igg conjugate (CPCP160), CPCP 100-labeled anti-CD antibodies and CPCP 200-Labeled Phalloidin Conjugate (CPCP 170) as described in the procedures of Examples 18 to 21.

For primary incubation, cells are incubated with a primary conjugate specific to an antigen of interest, negative cells served as a negative non-specific binding reference. A control population or an established commercial conjugate is used as a positive control. Primary antibody-polymer conjugates are incubated at various concentrations with volume dilutions typically from 10 nM-500 uM for 30 minutes.

For secondary antibody labeling, an unlabeled primary antibody to the antigen of interest is incubated at 1-50 μg/ml, or other titrated amount. Following primary incubation, cells are rinsed with 5 volumes staining buffer and spun down for 3-5 minutes. Species reactive secondary conjugated polymer conjugates are incubated at concentrations with volume dilutions from 10-500 nM for 30-60 minutes. Following secondary incubation, cells are rinsed with 3-5 volumes staining buffer and spun down for 3-5 minutes. Cells are resuspended for testing in DPBS+0.2% BSA, 0.05% sodium azide.

For streptavidin-polymer conjugate labeling, cells are incubated with a biotinylated primary antibody to the marker of interest, as detailed above for the secondary antibody labeling, instead of an unlabeled primary. Following the primary washing, cells are resuspended and incubated with streptavidin-polymer conjugates at 1-100 nM volume dilutions for 30 minutes. Following secondary incubation, cells are rinsed with 5 volumes staining buffer and spun down for 3-5 minutes. Cells are resuspended for testing. If further signal amplification is desired, cells could be incubated with an unlabeled primary antibody and then subsequently followed with a species reactive biotinylated secondary antibody prior to incubation with streptavidin conjugates.

It will be understood that the particular antibody conjugate used and the specific reaction components and particular reaction conditions used can have an effect on the results obtained. Routine experimentation should be carried out to determine preferred reaction components, such as buffers or lyse solutions, and reaction conditions, including staining times and temperatures. Such routine optimization of assay conditions is standard practice in the field of immunostaining-based assays.

What is claimed is:

1. A conjugated polymer of Formula 1 comprising a conjugated segment composed of x distinct comonomer units (Mr-1 to Mr-x) that are randomly distributed along the conjugated polymer backbone:

$$[[\text{Mr-1}]_{m1}[\text{Mr-2}]_{m2} \ldots [\text{Mr-x}]_{mx}] \quad \text{Formula 1}$$

wherein:

Mr-1 is of formula:

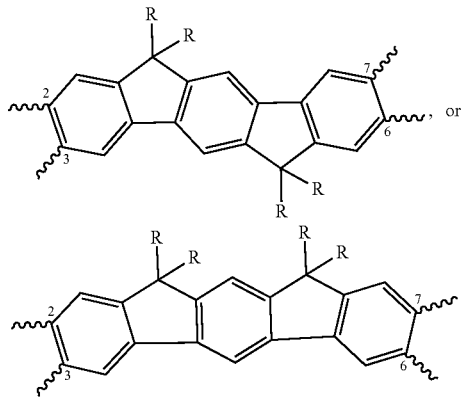

wherein:
- the Mr-1 comonomer units are connected to adjacent comonomers of the conjugated polymer backbone through any two positions of C2, C3, C6 and C7 of the Mr-1 comonomer;
- each R is independently selected from hydrogen, alkyl, substituted alkyl, a water solubilizing group (WSG), a linker, a linked WSG (L-WSG), a linked functional group (L-FG) and a linked biological substrate (L-BS);
- Mr-2 to Mr-x are distinct comonomer units each independently selected from ethenylene, acetylene, an aryl, a heteroaryl, and a fluorescent dye (FD);
- m1 is an integer greater than or equal to 5; and
- m2 to mx are each independently an integer from 0 to 200;

wherein:
(1) the sum of m1 through mx is ≥10; and
(2) at least one comonomer of Mr-1 comprises a water soluble group (WSG); and
(3) at least one comonomer of Mr-2 is represented by the following structure:

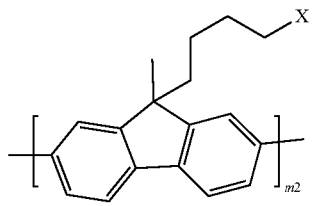

wherein:
X is FG or L-BS; and
m2 is an integer from 1 to 200.

2. The conjugated polymer of claim 1, wherein at least one of the Mr-1 to Mr-x co-monomers is a fluorescent dye (FD) or comprises a linked FD configured in energy receiving proximity to the conjugated polymer.

3. The conjugated polymer of claim 1, wherein the terminal comonomers of the conjugated polymer backbone are optionally and independently capped with phenyl, aryl, heteroaryl or a substituted version thereof that is substituted with bromo, iodo, boronyl, a FG or L-BS.

4. The conjugated polymer of claim 1, wherein the linker (L) comprises one or more groups selected from an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamide, a sulfonate ester, a 1,2,3-triazole, a pyradazine, a thiazolidine, a 2-diphenylphosphonyl-benzoamide, an isoxazole and a succinimide group.

5. The conjugated polymer of claim 1, wherein one or more of the WSG comprises a PEG group selected from PEG6 to PEG18.

6. The conjugated polymer of claim 1, wherein at least one of the Mr-1 to Mr-x co-monomers is a fluorescent dye (FD) or comprises a linked FD, wherein the FD is a fluorescein, a rhodamine, a rhodol, a cyanine, a bodipy, a squaraine, a coumarin, a perylenediimide, a diketopyrrolopyrrole, a porphyrin or a phthalocyanine.

7. A method of detecting an analyte in a sample, comprising
a) contacting said sample with a detection reagent comprising a conjugated polymer according to claim 1 under conditions in which said detection reagent binds said analyte, if present, to produce a detection reagent-bound analyte; and
b) detecting whether the detection reagent-bound analyte is present using fluorescence of the conjugated polymer.

8. The method of claim 7, wherein:
the detection reagent comprises an antibody;
the detection reagent comprises an anti-digoxigenin antibody;
the detection reagent comprises a goat anti-mouse IgG antibody, goat anti-rabbit IgG antibody, goat anti-human IgG antibody, donkey anti-mouse IgG antibody, donkey anti-rabbit IgG antibody, donkey anti-human IgG antibody, chicken anti-mouse IgG antibody, chicken anti-rabbit IgG antibody, or chicken anti-human IgG antibody; or
the detection reagent comprises an avidin, streptavidin, neutravidin, avidinDN, or avidinD moiety.

9. The method according to claim 7, wherein the analyte is a target protein expressed on a cell surface.

10. The conjugated polymer of claim 4, wherein the linker comprises an alkyl or a PEG group.

11. The conjugated polymer of claim 1, wherein at least one comonomer of Mr-1 to Mr-x comprises a linked biological substrate (L-BS), wherein:
L is an alkyl chain or a PEG chain; and
BS is an antibody, a peptide, a protein, an oligonucleotide, a nucleic acid or a carbohydrate.

12. The conjugated polymer of claim 11, wherein BS is an antibody.

13. The conjugated polymer of claim 1, wherein each R is a linked WSG (L-WSG), wherein:
L is an alkyl chain; and
WSG is a PEG group.

14. The conjugated polymer of claim 13, wherein the PEG group is selected from PEG6 to PEG18.

15. The conjugated polymer of claim 1, wherein Mr-1 is represented by the following structure:

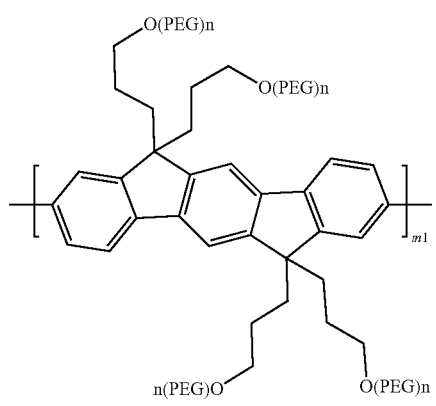

wherein:
n is an integer from 6 to 18.

16. The conjugated polymer of claim 1, wherein Mr-1 comonomer units are connected to adjacent comonomers of the conjugated polymer backbone through C2 and/or C7 positions of the Mr-1 comonomer.

17. The conjugated polymer of claim 1, wherein Mr-1 comonomer units are connected to adjacent comonomers of the conjugated polymer backbone through C3 and/or C6 positions of the Mr-1 comonomer.

18. The conjugated polymer of claim 11, wherein X is FG.

19. The conjugated polymer of claim 11, wherein X is L-BS, wherein L comprises an alkyl or a PEG group.

20. The conjugated polymer of claim 19, wherein L is an alkyl linker.

21. The conjugated polymer of claim 19, wherein L comprises a PEG group.

22. The conjugated polymer of claim 19, wherein BS is an antibody.

23. The conjugated polymer of claim 19, wherein BS is avidin, streptavidin, or neutravidin.

24. The conjugated polymer of claim 1, wherein the sum of m1 through mx is 10 up to 10,000.

25. The conjugated polymer of claim 24, wherein the sum of m1 through mx is 10 up to 2,000.

26. The conjugated polymer of claim 25, wherein the sum of m1 through mx is 10 up to 1,000.

27. The conjugated polymer of claim 1, wherein each R is WSG or L-WSG, wherein WSG is a PEG, a carboxyalkyl, a sulfonylalkyl, a phosphonylalkyl, a hydroxyalkyl, an aminoalkyl or an ammoniumylalkyl.

* * * * *